United States Patent
Iida et al.

(10) Patent No.: US 8,252,432 B2
(45) Date of Patent: Aug. 28, 2012

(54) COMPOSITION FOR CHARGE-TRANSPORTING FILM AND ION COMPOUND, CHARGE-TRANSPORTING FILM AND ORGANIC ELECTROLUMINESCENT DEVICE USING SAME, AND METHOD FOR MANUFACTURING ORGANIC ELECTROLUMINESCENT DEVICE AND METHOD FOR PRODUCING CHARGE-TRANSPORTING FILM

(75) Inventors: Koichiro Iida, Kanagawa (JP); Tomoyuki Ogata, Kanagawa (JP); Asato Tanaka, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 12/882,502

(22) Filed: Sep. 15, 2010

(65) Prior Publication Data

US 2011/0001134 A1    Jan. 6, 2011

Related U.S. Application Data

(62) Division of application No. 10/591,972, filed as application No. PCT/JP2005/003920 on Mar. 7, 2005, now Pat. No. 7,879,461.

(30) Foreign Application Priority Data

Mar. 11, 2004 (JP) ................. 2004-068958
Jan. 28, 2005 (JP) ................. 2005-021983

(51) Int. Cl.
*H01J 1/63* (2006.01)
(52) U.S. Cl. ........ 428/690; 428/917; 313/504; 313/506
(58) Field of Classification Search ............. 428/690; 313/504, 506; 257/79; 556/1, 7, 27; 568/1, 568/6
See application file for complete search history.

(56) References Cited

U.S. PATENT DOCUMENTS

| | | | |
|---|---|---|---|
| 4,338,222 A | 7/1982 | Limburg et al. | |
| 5,541,349 A | 7/1996 | Wilson et al. | |
| 5,587,224 A | 12/1996 | Hsieh et al. | |
| 5,853,906 A | 12/1998 | Hsieh | |
| 5,968,674 A | 10/1999 | Hsieh et al. | |
| 5,998,045 A * | 12/1999 | Chen et al. | 428/690 |
| 6,340,528 B1 | 1/2002 | Hsieh et al. | |
| 6,459,199 B1 | 10/2002 | Kido et al. | |
| 2007/0020479 A1 * | 1/2007 | Uetani et al. | 428/690 |

FOREIGN PATENT DOCUMENTS

| | | |
|---|---|---|
| EP | 0 493 054 A1 | 7/1992 |
| EP | 0 910 099 A1 | 4/1999 |
| EP | 0 910 100 A2 | 4/1999 |
| JP | 10-92581 | 4/1998 |
| JP | 10-168446 | 6/1998 |
| JP | 11 251067 | 9/1999 |
| JP | 11 283750 | 10/1999 |
| JP | 2000036390 A | 2/2000 |
| JP | 2000 229931 | 8/2000 |
| JP | 2001-68272 | 3/2001 |
| JP | 2001 131185 | 5/2001 |
| JP | 2001-244079 | 9/2001 |
| JP | 2001 266963 | 9/2001 |
| JP | 2002056973 A | 2/2002 |
| JP | 2002 80433 | 3/2002 |
| JP | 2003 31365 | 1/2003 |
| JP | 2003 81924 | 3/2003 |
| JP | 2003 197942 | 7/2003 |
| JP | 2004002740 A | 1/2004 |
| JP | 2008135741 A | 6/2008 |
| WO | WO 97/43874 | 11/1997 |
| WO | WO 00/60612 A1 | 10/2000 |
| WO | WO 2005/089024 A1 | 9/2005 |

OTHER PUBLICATIONS

Office Action issued Feb. 22, 2011 in Japan Application No. 2007-297942 (With English Translation).
Extended Search Report issued Apr. 21, 2011 in Europe Application No. 11155558.7.
Mathew K. Mathai, et al., "Controlled Injection of Holes into $ALQ_3$ Based Oleds by Means of an Oxidized Transport Layer", Mat. Res. Soc. Symp. Proc., vol. 708, 2002, pp. BB3.27.1-BB3.27.6.

* cited by examiner

*Primary Examiner* — David W Wu
*Assistant Examiner* — Vu A Nguyen

(74) *Attorney, Agent, or Firm* — Oblon, Spivak, McClelland, Maier & Neustadt, L.L.P.

(57) ABSTRACT

A composition for preparing a charge-transport film is provided. The composition comprises, at least: a charge-transporting compound having an ionization potential of between 4.5 and 5.5 ev; and an ionic compound selected from the group consisting of the compounds of formulae (1)-(3),

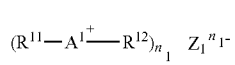 (1)

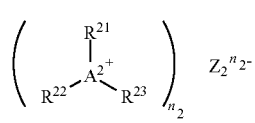

(2)

-continued

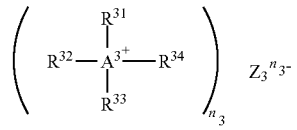 (3)

wherein $R^{11}$, $R^{21}$ and $R^{31}$ are each independently an organic group bound to $A^1$-$A^3$, via a carbon atom; $R^{12}$, $R^{22}$, $R^{23}$ and $R^{32}$-$R^{34}$ are each independently an arbitrary group. Two or more neighboring groups of $R^{11}$-$R^{34}$ may combine to form a ring. $A^1$-$A^3$ are each an element of the third and subsequent periods in the periodic table. $A^1$ is an element of group 17 of the long form periodic table; $A^2$ is an element of group 16 and $A^3$ is an element of group 15. $Z_1^{n1-}$-$Z_3^{n3-}$ are counter anions and n1-n3 are an ionic valency of the counter anion.

18 Claims, 2 Drawing Sheets

COMPOSITION FOR CHARGE-TRANSPORTING FILM AND ION COMPOUND, CHARGE-TRANSPORTING FILM AND ORGANIC ELECTROLUMINESCENT DEVICE USING SAME, AND METHOD FOR MANUFACTURING ORGANIC ELECTROLUMINESCENT DEVICE AND METHOD FOR PRODUCING CHARGE-TRANSPORTING FILM

CROSS REFERENCE TO RELATED APPLICATIONS

This application is a divisional application of prior U.S. patent application Ser. No. 10/591,972, filed Sep. 8, 2006, the disclosure of which is incorporated herein by reference in its entirety. The parent application is the National Stage of PCT/JP05/03920, filed Mar. 7, 2005, the disclosure of which is incorporated herein by reference in its entirety. The parent application claims priority to Japanese Application No. 2004-068958, filed Mar. 11, 2004, and to Japanese Application No. 2005-021983, filed Jan. 28, 2005, the disclosures of which are incorporated herein by reference in their entireties.

TECHNICAL FIELD

The present invention relates to a composition for a charge-transport film and an ionic compound, a charge-transport film and organic electroluminescence device using them, and production methods of the organic electroluminescence device and the charge-transport film. Specifically, the present invention relates to an excellent composition for a charge-transport film and an ionic compound which can be used to produce an organic electroluminescence device having excellent heat-resistant property and capable of functioning at a low voltage, a charge-transport film using either the composition or the compound, and their production methods, as well as an organic electroluminescence device using either the composition or the compound and its production method.

BACKGROUND ART

Recently, an electroluminescence (EL) device using organic materials (organic electroluminescence device), in place of inorganic materials such as ZnS, has been developed. One of the important issues with an organic electroluminescence device is how to achieve high luminous efficiency. In this respect, a great progress has been made by use of a hole-transport layer containing aromatic amines and an emitting layer containing 8-hydroxyquinoline aluminum complex.

An important problem that has to be overcome to expand the demand for an organic electroluminescence device is how to lower its driving voltage. For example, it is required that display devices of portable instruments can operate at a low driving voltage from a battery. For its general use also, apart from portable instruments, the cost of driving IC depends on driving voltage, and the cost becomes lower as the driving voltage is lowered. Gradual increase in driving voltage on continuous use also presents a serious problem in maintaining stability in performance of display devices.

In order to solve these problems, attempts are being made to mix an electron-accepting compound with a hole-transporting compound.

For example, in Patent Document 1, it is indicated that, by mixing tris(4-bromophenyl aminiumhexachloroantimonate) (TBPAH) as an electron-accepting compound with a hole-transporting macromolecule compound, it is possible to obtain an organic electroluminescence device capable of functioning at a low voltage.

In Patent Document 2, a method is described, wherein an electron-accepting compound ferric chloride (III) ($FeCl_3$) is mixed with a hole-transporting compound by means of vacuum vapor deposition.

In Patent Document 3, a method is described, wherein an electron-accepting compound tris(pentafluorophenyl)borane (PPB) is mixed with a hole-transporting macromolecule compound by means of a wet coating method to form a hole-injection layer.

When a hole-transporting compound is mixed with an electron-accepting compound, electrons are transferred from the hole-transporting compound to the electron-accepting compound, and an ionic compound is formed which consists of a cation radical of the hole-transporting compound and a counter anion originating from the electron-accepting compound.

When TBPAH described in Patent Document 1 is used as an electron-accepting compound, the counter anion is $SbCl_6^-$. When $FeCl_3$ described in Patent Document 2 is used as an electron-accepting compound, the counter anion is $Cl^-$ (or $FeCl_4^-$). When PPB described in Patent Document 3 is used as an electron-accepting compound, the counter anion is an anion radical shown below.

[Chemical Formula 1]

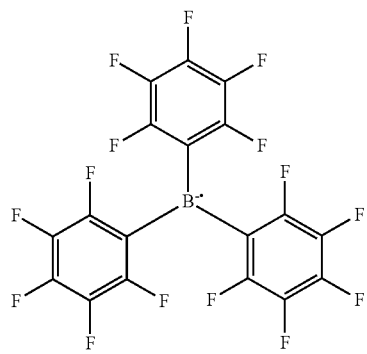

(An anion radical means a chemical species having unpaired electrons and negative charge. The negative charge is thought to be spread over the entire molecule. However, in the above chemical formula, the resonance structure thought to have the greatest possible contribution is shown.)

In Patent Document 4, an ionic compound consisting of an aminium cation radical and $SbF_6^-$ or $BF_4^-$ is indicated as a component of a charge-transport film of a photovoltanic instrument (organic solar battery).

Patent Document 5 suggests the use of an ionic compound consisting of an aminium cation radical and a counter anion as a component of an electro-conductive coating film (charge-transport film). As counter anions are exemplified halide ion such as $I^-$, polyhalide ion such as $Br_3^-$, oxonic acid ion such as $ClO_4^-$ and $PO_3^-$, ion consisting of center ion and halogen such as $BF_4^-$, $FeCl_4^-$, $SiF_6^{2-}$ and $RuCl_6^{2-}$, carboxylate ion such as $CF_3COO^-$, sulfonate ion such as $CF_3SO_2O^-$, ate complex originating from sulfonate ion such as $(CF_3SO_3)_4Al^-$, $C_{60}^-$, $C_{60}^{2-}$, and $B_{12}H_{12}^{2-}$.

Ionic compounds consisting of an aminium cation radical and a counter anion have an absorption band in the near infrared region and in Patent Document 6, an indication is given to use these compounds as infrared cut filter. Tetraphenylborate ion is exemplified as a counter anion.

[Patent Document 1] Japanese Patent Laid-Open Application No. HE 11-283750
[Patent Document 2] Japanese Patent Laid-Open Application No. HE 11-251067
[Patent Document 3] Japanese Patent Laid-Open Application No. 2003-31365
[Patent Document 4] Japanese Patent Laid-Open Application No. 2003-197942
[Patent Document 5] U.S. Pat. No. 5,853,906
[Patent Document 6] Japanese Patent Laid-Open Application No. 2000-229931

DISCLOSURE OF THE INVENTION

Problem to be Solved by the Invention

However, TBPAH described in Patent Document 1 is poor in its heat stability and is decomposed by heat during vapor deposition, making it unsuitable for use for the formation of a hole-injection layer by means of co-deposition. This compound, therefore, is usually mixed with a hole-transporting compound by a wet coating method. However, because of its poor solubility, it is not suitable for the wet coating method, either. Furthermore, electron-accepting property of TBPAH is weak and, even when mixed with a hole-transporting compound, there is a limit below which the driving voltage of a device cannot be lowered. Another problem is that antimony atom contained in TBPAH shows strong toxicity and is not desirable from this point of view.

$FeCl_3$ described in Patent Document 2 is corrosive in nature and damages a vacuum vapor deposition instrument, making it unsuitable to be used with this instrument. On the other hand, ITO (indium tin oxide), which is routinely used as anode of an organic electroluminescence device, has some extent of roughness on its surface (approx. 10 nm), is rich in locally located projections in many cases, and is liable to short circuit arising from this property. It is preferable, therefore, to form a hole-injection layer on a anode by a wet coating method. In this context, the solubility of $FeCl_3$ in solvents is extremely poor and, because of this, $FeCl_3$ is not suitable for the wet coating method, either.

When TBPAH or $FeCl_3$, mentioned above, is used as electron-accepting compound, a counter anion of an ionic compound formed is $SbCl_6^-$ or $Cl^-$ (or $FeCl_4^-$). Because negative charge is localized in these anions, they interact strongly with a radical cation of a hole-transporting compound, and transfer of positive charge is difficult to occur, as the result of which driving voltage is not sufficiently low.

When an ionic compound, which is described in Patent Document 4 or 5 and which comprises an aminium cation radical and a counter anion selected from the group consisting of halide ion such as $I^-$, polyhalide ion such as $Br_3^-$, oxonic acid ion such as $ClO_4^-$, $PO_3^-$, ions consisting of center element like $BF_4^-$, $FeCl_4^-$, $SiF_6^{2-}$, $RuCl_6^{2-}$ and halogen, carboxylate counter anion such as $CF_3COO^-$, sulfonate ion such as $CF_3SO_2O^-$, is used as a component of a hole-injection layer of an organic electroluminescence device, the anion interacts strongly with the aminium cation radical because negative charge is localized in the anion, and transfer of positive charge is difficult to occur, as the result of which driving voltage is not sufficiently low.

PPB described in Patent Document 3 is poor in its heat stability and, therefore, an organic electroluminescence device containing PPB is also poor in heat stability, making it unsuitable for practical use. Furthermore, PPB sublimes very easily and, when heating/drying is conducted at a temperature of 120° C. or higher at the time of the formation of a hole-injection layer containing PPB by the method of wet coating, the compound is lost by sublimation and the driving voltage of an organic electroluminescence device is higher than when heating/drying is conducted at a temperature lower than 120° C. In the production of an organic electroluminescence device, it is preferable to use a hole-injection layer which can be heated/dried at a higher temperature, for example 200° C. or higher, in order to simplify the production process and to realize the stable device characteristics. PPB is not preferable from these points of view, either. In addition, the control of the concentration of PPB is difficult at the time of co-deposition because of its very easy sublimation, and it is also unsuitable for use for the formation of a hole-injection layer by co-deposition with hole-transporting materials.

Furthermore, when PPB described in Patent Document 3 is used as electron-accepting compound, a counter anion formed in an ionic compound is an anion radical described previously, and does not satisfy the octet rule. It is therefore unstable thermodynamically and electrochemically, and this presents a stability problem including thermostability of a coating solution (composition) and thermostability of devices.

When an ionic compound disclosed in Patent Document 5, which comprises an aminium cation radical and a counter anion, selected from the group consisting of carboxylate ion such as $CF_3COO^-$, sulfonate ion such as $CF_3SO_2O^-$, ate complex originating from sulfonate ion such as $(CF_3SO_3)_4 Al^-$, $C_{60}^-$, $C_{60}^{2-}$, and $B_{12}H_{12}^{2-}$, is used as a component of a hole-injection layer of an organic electroluminescence device, the ionic compound is unstable thermodynamically and electrochemically due to the structure of the counter anion, and the stability of the device, including the heat stability of the coating solution (composition) and heat stability of the device characteristics, is considered inadequate.

The present invention has been made in order to solve these problems. The purpose of the present invention is: to provide excellent composition for a charge-transport film and ionic compound which can be used to obtain an organic electroluminescence device which has excellent heat stability, has high hole-injection/transport capability, is capable of functioning at a low driving voltage and has excellent driving stability including heat stability; to provide, using the above, an organic electroluminescence device which can be operated at a low voltage and has excellent driving stability including heat stability, and the method of producing the same; to provide charge-transport film using the above and the method of producing the same.

Means for Solving the Problem

The present inventors have carried out an intensive investigation and found that it is possible to obtain a composition for a charge-transport film having excellent heat stability and high hole-injection/transport capability by mixing with a charge-transporting compound an ionic compound in which an element belonging to groups 15-17 of the periodic table has at least one organic group bonded to it via carbon. It was also found that, by using the above composition, it is possible to obtain an organic electroluminescence device capable of functioning at a low voltage. These findings led us to the effective solution of the above-mentioned problems.

Further, an intensive investigation was carried out on an ionic compound consisting of a charge-transporting cation radical and a counter anion, wherein the ionic compound is formed when an electron-accepting compound is mixed with a charge-transporting compound. As a result, it was possible to obtain a composition for a charge-transport film having excellent heat stability and high hole-injection/transport capability, by using an ionic compound comprising a charge-transporting cation radical and a counter anion, which anion has an element belonging to group 13 of the periodic table and four aromatic substituents bonded to the element. Furthermore, by using this composition, it was possible to obtain an organic electroluminescence device capable of functioning at a low voltage. Thus, we have found the way to solve effectively the problems presented above and the present invention has been completed.

According to an aspect of the present invention, there is provided a composition for a charge-transport film, comprising at least: a charge-transporting compound; and an ionic compound (hereinafter, a cation radical of this charge-transporting compound is called an "electron-accepting ionic compound" so as to be distinguished from an ionic compound comprising a counter anion, represented by below-described general formula (7), as a matter of convenience) selected from the group consisting of the compounds expressed by the following general formulae (1)-(3),

[Chemical Formula 2]

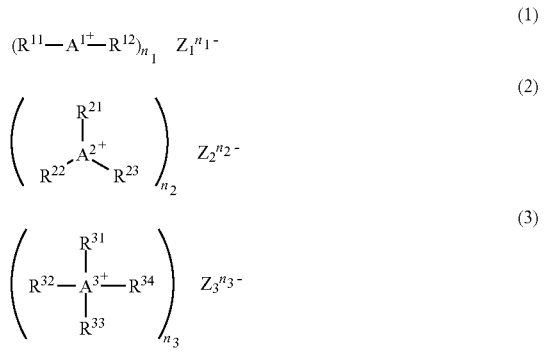

wherein in general formulae (1)-(3): $R^{11}$, $R^{21}$ and $R^{31}$ represent, independently of each other, an organic group bound to $A^1$-$A^3$, respectively, via a carbon atom; $R^{12}$, $R^{22}$, $R^{23}$ and $R^{32}$-$R^{34}$ represent, independently of each other, an arbitrary group; two or more neighboring groups of $R^{11}$-$R^{34}$ may combine together to form a ring; $A^1$-$A^3$ each represent an element belonging to the third and subsequent periods in the periodic table; $A^1$ represents an element belonging to group 17 of the long form periodic table; $A^2$ represents an element belonging to group 16 of the long form periodic table; $A^3$ represents an element belonging to group 15 of the long form periodic table; $Z_1^{n1-}$-$Z_3^{n3-}$ represent, independently of each other, a counter anion; and n1-n3 represent, independently of each other, an ionic valency of the counter anion.

According to another aspect of the present invention, there is provided an organic electroluminescence device, comprising: a substrate; an anode and cathode formed on said substrate; an emitting layer disposed between said anode and said cathode; and a layer formed between said anode and said emitting layer using a composition for a charge-transport film as defined above.

According to still another aspect of the invention, there is provided an organic electroluminescence device, comprising: a substrate; an anode and a cathode formed on said substrate; an emitting layer disposed between said anode and said cathode; a layer, disposed between said anode and said cathode, that contains at least one electron-accepting ionic compound selected from the group consisting of the compounds expressed by the above described general formulae (1)-(3)

According to still another aspect of the invention, there is provided a method of producing an organic electroluminescence device as defined above, comprising the step of drying said composition for a charge-transport film by heating at a higher temperature than the glass transition temperature of said charge-transporting compound.

According to still another aspect of the invention, there is provided a method of producing a charge-transport film by wet coating method using a composition for a charge-transport film as defined above, comprising the step of drying said composition for a charge-transport film by heating at a higher temperature than the glass transition temperature of said charge-transporting compound.

According to still another aspect of the invention, there is provided a ionic compound (hereinafter called an "ion radical compound", if necessary, so as to be distinguished from an ionic compound selected from a group of compounds represented by above-described general formulae (1)-(3), as a matter of convenience) composed of a cation radical of a charge-transporting compound and a counter anion, wherein said counter anion is expressed by the following general formula (7)

[Chemical Formula 3]

wherein in the general formula (7): $E^4$ represents an element belonging to group 13 of the long form periodic table; and $Ar^{71}$-$Ar^{74}$ represent, independently of each other, an aromatic hydrocarbon group that may have substituents or an aromatic heterocyclic group that may have substituents.

According to still another aspect of the invention, there is provided a composition for a charge-transport film, comprising at least an ion radical compound as defined before.

According to still another aspect of the invention, there is provided a charge-transport film, comprising at least an ion radical compound as defined before.

According to still another aspect of the invention, there is provided an organic electroluminescence device, comprising a layer comprising at least an ion radical compound as defined before.

According to still another aspect of the invention, there is provided an electron-accepting compound to be contained in a charge-transport film together with a charge-transporting compound, wherein a resistivity $RR_1$ [Ωcm] of a charge-transport film 1, which is composed of said electron-accepting compound and a charge-transporting compound, and resistivity $RR_0$ [Ωcm] of a charge-transport film 2, which is composed of a charge-transporting compound, meet the following relation $$RR_1/RR_0 8 \times 10^{-2}$$

on the conditions: that a same compound is used as the charge-transporting compounds contained in the charge-transport film 1 and the charge-transport film 2; and that the resistivity is the value of {field intensity [V/cm]/current density [A/cm²]} where the {field intensity [V/cm]/current density [A/cm²]} is obtained from a field intensity to be applied when a charge-transport film having a film thickness of between 100-200 nm and a current-carrying area of 0.04 cm² carries an electric current corresponding to a current density of between 4-6 mA/cm² while being sandwiched between an anode and a cathode.

According to still another aspect of the invention, there are provided a composition for a charge-transport film and charge-transport film, comprising above described electron-accepting compound and charge-transporting compound, and is provided an organic electroluminescence device comprising said charge-transport film.

Advantageous Effects of the Invention

The composition for a charge-transport film of the present invention comprises an above-mentioned electron-accepting ionic compound in addition to a charge-transporting compound. As a result, a charge-transport film formed has an excellent heat-resistant property and shows high hole-injection/transport capability.

An organic electroluminescence device of the present invention comprises the above-mentioned electron-accepting ionic compound in a layer present between a cathode and an anode or emitting layer. As a result, the device shows an excellent heat-resistant property and is capable of functioning at a low voltage leading to stability in driving.

Furthermore, according to the production methods of an organic electroluminescence device and a charge-transport film of the present invention, it is possible to include a heating/drying process at a high temperature when a layer or a film is formed by a wet coating method using the above-mentioned composition for a charge-transport film. The production method is, therefore, expected to be made simple, and device characteristics or film characteristics are expected to be improved regarding stability.

The ionic compounds (ion radical compounds) of the present invention consist of a cation radical of a charge-transporting compound and a counter anion expressed by the general formula (7). A counter anion expressed by the general formula (7) is stable both thermodynamically and electrochemically. Therefore, the ionic compounds of the present invention (ion radical compounds) are superior in both heat resistance and electrochemical durability. Furthermore, in a counter anion expressed by the general formula (7), negative charge is diffused and not localized, and because of this, its interaction with a cation is weak, presenting little obstacle in charge-transport.

The composition for a charge transport film of the present invention comprises an above-mentioned ion radical compound. As a result, the charge transport film formed has an excellent heat-resistant property, excellent electrochemical durability and shows high hole-injection/transport capability.

The charge-transport film of the present invention comprises the above-mentioned ion radical compounds. As a result, it has an excellent heat-resistant property and excellent electrochemical durability, and shows high hole-injection/transport capability.

Furthermore, an organic electroluminescence device of the present invention comprises a layer containing, at least, ion radical compounds described above. As a result, the device has an excellent heat-resistant property, is capable of functioning at a low voltage, and is excellent in driving stability.

EXPLANATION FOR SYMBOLS

Figure 1A:
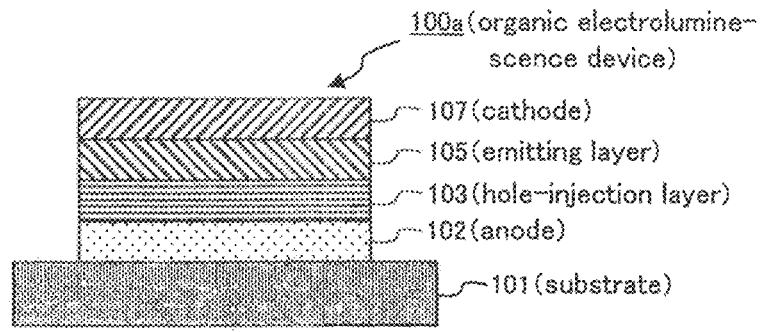
FIGS. 1(a) to 1(c) are schematic cross-sectional views illustrating examples of the structure of organic electroluminescence devices of one embodiment of the present invention.

100a, 100b, 100c: organic electroluminescence device
101: substrate
102: anode
103: hole-injection layer
104: hole-transport layer
105: emitting layer
106: electron transport layer
107: cathode

BEST MODE FOR CARRYING OUT THE INVENTION

The present invention will be explained in detail below referring to one embodiment. However, it is to be understood that the following explanation about constituent features is presented as a representative example of an embodiment of the present invention, and the present invention is not limited to these constituent features.

[I. Ionic Compound (Ion Radical Compound)]

The ionic compound of the present invention comprises a cation radical of a charge-transporting compound, and a counter anion represented by the general formula (7) shown below. In the explanation which follows, this ionic compound is called "ion radical compound" for the sake of convenience. Incidentally, in the present invention, a charge-transporting compound is usually a hole-transporting compound. Therefore, in this description, explanation will be given on the assumption that a charge-transporting compound is a hole-transporting compound, unless otherwise mentioned.

[I-1. Counter Anion]

A counter anion, which is an anion of an ion radical compound of the present invention, is a chemical species represented by the following general formula (7).

[Chemical Formula 4]

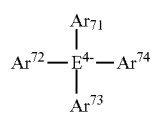

(7)

(In the general formula (7), $E^4$ represents an element belonging to the group 13 of the long form periodic table and $Ar^{71}$-$Ar^{74}$ represent, independently of each other, an aromatic hydrocarbon group that may have substituents or an aromatic heterocyclic group that may have substituents.)

In the general formula (7), $E^4$ represents, independently of each other, an element which belongs to group 13 of the long form periodic table. Preferable is a boron atom, aluminum atom or gallium atom. Particularly preferable is a boron atom, because the compound is then chemically stable, easy to synthesize and easy to purify.

In the general formula (7), $Ar^{71}$-$Ar^{74}$ represent, independently of each other, an aromatic hydrocarbon group or an aromatic heterocyclic group.

As aromatic hydrocarbon group is preferred a univalent group derived from a 5- or 6-membered monocyclic ring or from a compound having 2 to 5 condensed rings. Examples of the ring structures include benzene, naphthalene, anthracene, phenanthrene, perylene, tetracene, pyrene, benzpyrene, chrysene, triphenylene, acenaphthene and fluorine. Of these ring structures, particularly preferable are univalent groups originating from benzene, naphthalene, phenanthrene, pyrene and fluorene, because they are chemically stable and heat-resistant.

As aromatic heterocyclic group is preferred a univalent group derived from 5- or 6-membered monocyclic ring or from a compound having 2 to 4 condensed rings. Examples of the ring structures include furan, benzofuran, thiophen, benzothiophen, pyrrole, pyrazole, triazole, imidazole, oxadiazole, indole, carbazole, pyrroloimidazole, pyrrolopyrazole, pyrrolopyrrole, thienopyrrole, thienothiophen, furopyrrole, furofuran, thienofuran, benzoisoxazole, benzoisothiazole, benzoimidazole, pyridine, pyrazine, pyridazine, pyrimidine, triazine, quinoline, isoquinoline, cinnoline, quinoxaline, phenanthridine, benzoimidazole, perimidine, quinazoline and azulene. Of these ring structures, particularly preferable are univalent groups originating from pyridine, pyrazine, pyrimidine, triazine, quinoline, isoquinoline, quinoxaline and phenanthridine, because they are chemically stable, heat-resistant and capable of delocalizing negative charge efficiently.

Aromatic hydrocarbon group and aromatic heterocyclic group, exemplified as $Ar^{71}$-$Ar^{74}$, may carry substituents insofar as they do not depart from the scope of the present invention. There is no special limitation on the kind of the substituent and any substituent is possible. However, it is preferable that it is an electron-accepting group.

An electron-accepting group preferable as substituent of $Ar^{71}$-$Ar^{74}$ includes following examples: halogen atom such as fluorine atom, chlorine atom and bromine atom; cyano group; thiocyano group; nitro group; alkylsulfonyl group such as mesyl group; arylsulfonyl group such as tosyl group; acyl group having usually one or more carbon atoms and usually 12 or less, preferably 6 or less carbon atoms such as formyl group, acetyl group and benzoyl group; alkoxycarbonyl group having usually 2 or more carbon atoms and usually 10 or less, preferably 7 or less carbon atoms such as methoxycarbonyl group and ethoxycarbonyl group; aryloxycarbonyl group containing aromatic hydrocarbon group or aromatic heterocyclic group having usually 3 or more, preferably 4 or more carbon atoms and usually 25 or less, preferably 15 or less carbon atoms, such as phenoxycarbonyl group and pyridyloxycarbonyl group; aminocarbonyl group; aminosulfonyl group; haloalkyl group with straight chain, branched chain or cyclic alkyl group having usually one or more, usually 10 or less, preferably 6 or less carbon atoms and having halogen substituent like fluorine or chlorine, such as trifluoromethyl group and pentafluoroethyl group.

In particular, it is preferable that at least one group of $Ar^{71}$-$Ar^{74}$ has one or more fluorine or chlorine atoms as substituent. It is most preferable that all the hydrogen atoms of $Ar^1$-$Ar^4$ are replaced with fluorine atoms giving perfluoroaryl group, from the standpoint of efficient delocalization of negative charge and suitable sublimation property. As examples of perfluoroaryl group can be cited pentafluorophenyl group, heptafluoro-2-naphtyl group and tetrafluoro-4-pyridyl group.

Furthermore, it is preferable that $Ar^{71}$-$Ar^{74}$ have a substituent represented by the formula (7') below.

[Chemical Formula 5]

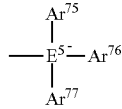

(7')

(In the formula (7'), $E^5$ represents an element which belongs to group 13 of the long form periodic table and $Ar^{75}$-$Ar^{77}$ represent, independently of each other, an aromatic hydrocarbon group that may have substituents or an aromatic heterocyclic group that may have substituents.)

In the formula (7'), $E^5$ represents, independently of each other, an element which belongs to group 13 of the long form periodic table. Preferable is a boron atom, aluminum atom or gallium atom. Particularly preferable is a boron atom, because the compound is then chemically stable, easy to synthesize and easy to purify.

In the formula (7'), $Ar^{75}$-$Ar^{77}$ represent, independently of each other, an aromatic hydrocarbon group that may have substituents or an aromatic heterocyclic group that may have substituents. Concrete examples, preferable examples, examples of substituents and preferable examples of substituents are the same as those described above for $Ar^{71}$-$Ar^{74}$.

It is preferable that a counter anion represented by the formula (7) has, in its structure, two or more partial structures represented by the formula (7'). When it possesses two or more such partial structures, they may be either two different structures or the same structure. Preferably, they are of the same structure.

The molecular weight of $Ar^{71}$-$Ar^{74}$, including their substituents, is usually within the range of 1000 or smaller, preferably 500 or smaller, more preferably 300 or smaller.

The molecular weight of a counter anion is usually 100 or larger, preferably 200 or larger, more preferably 300 or larger. It is usually 4000 or smaller, preferably 2000 or smaller, more preferably 1000 or smaller. If the molecular weight of a counter anion is too small, delocalization of negative charge is insufficient and interaction with a cation is too strong, leading to lower charge transporting capacity. If the molecular weight of a counter anion is too large, the counter anion itself may hinder charge transport.

In the present invention, the expression "may have substituents" means "may have at least one substituent".

A counter anion, which is an anion of an ion radical compound of the present invention, will be exemplified below. It is to be understood that they are cited as examples and by no means restrictive.

[Chemical Formula 6]
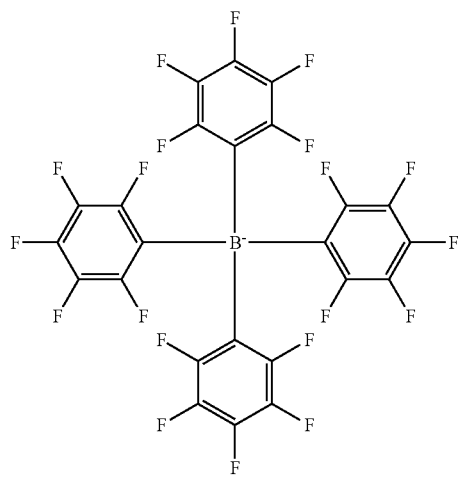
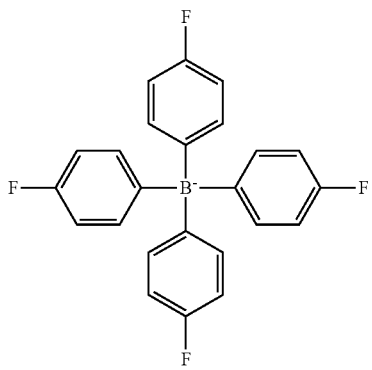
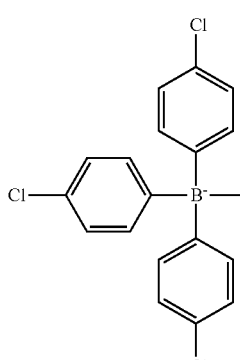
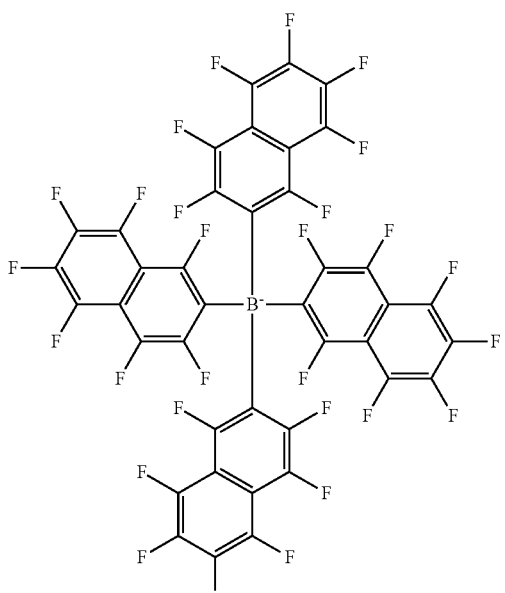
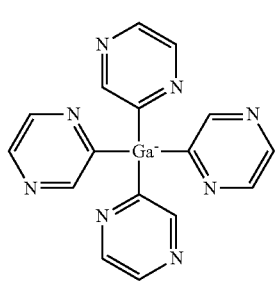

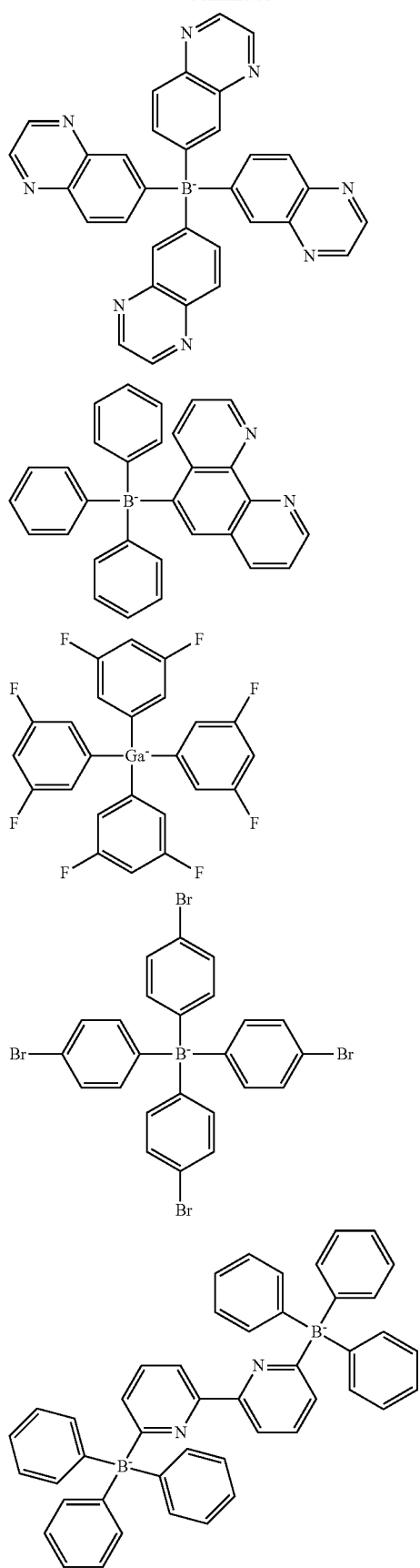
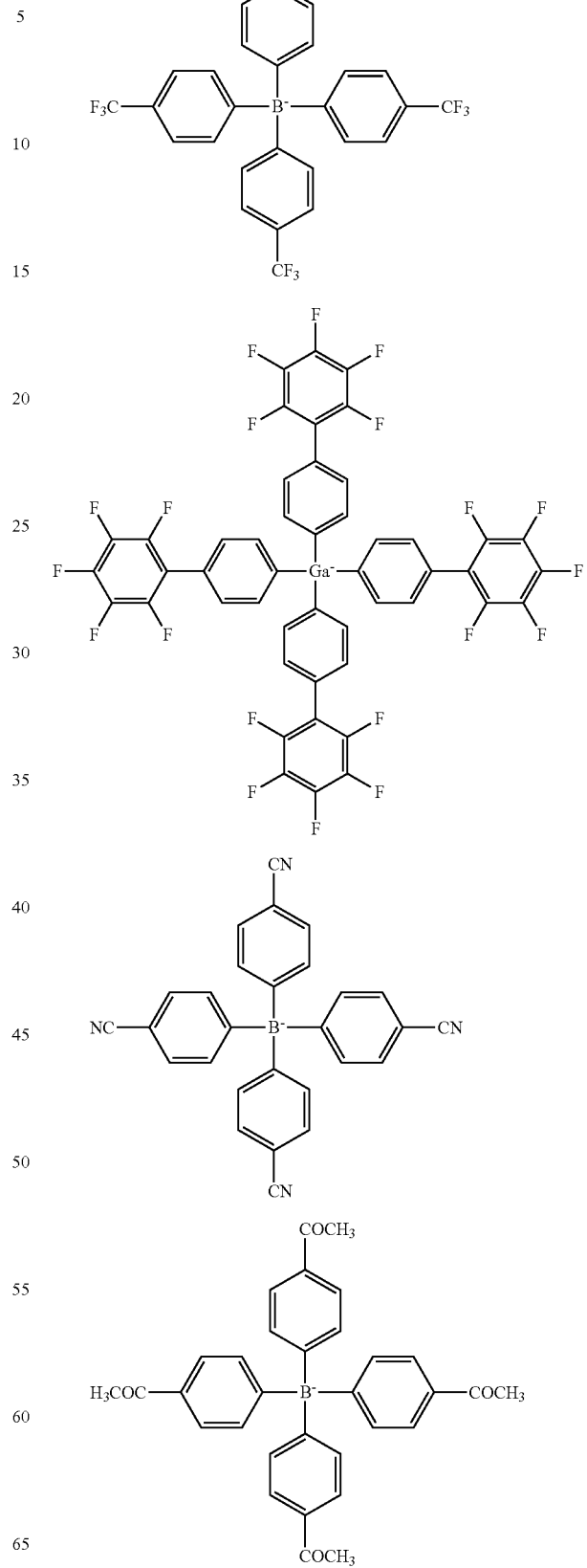

-continued

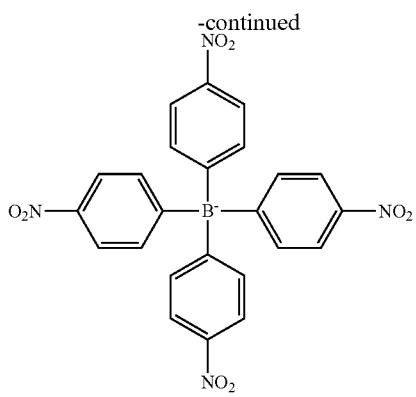

[I-2. Cation Radical of a Hole-Transporting Compound]

The cation radical of a hole-transporting compound, which is a cation of an ion radical compound of the present invention, is a chemical species wherein one electron is removed from an electrically neutral compound shown later in [II-2. hole-transporting compound]. In the case where a hole-transporting compound is a macromolecule compound, it is a chemical species wherein one electron is removed from its repetitive unit. Its examples and preferable examples are the same as those described later for a hole-transporting compound.

In particular, it is preferable that a cation radical of a hole-transporting compound has a structure represented by the following general formula (10), because the cation radical then has an appropriate oxidation-reduction potential and is chemically stable.

[Chemical Formula 7]

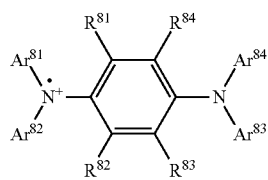

(10)

(In the general formula (10), $Ar^{81}$-$Ar^{84}$ represent, independently of each other, an aromatic hydrocarbon group that may have substituents or an aromatic heterocyclic group that may have substituents, and $R^{81}$-$R^{84}$ represent, independently of each other, an arbitrary group.)

Concrete examples and preferable examples of $Ar^{81}$-$Ar^{84}$, examples of substituents which can be introduced and examples of preferable substituents are the same as those described later for $Ar^{21}$ and $Ar^{22}$. Preferable as $R^{81}$-$R^{84}$ is a hydrogen atom or substituents described later for [substituent groups W]. More preferable are a hydrogen atom, alkyl group, alkoxy group, amino group, aromatic hydrocarbon group and aromatic hydrocarbon group.

Furthermore, it is preferable, from the standpoint of heat stability and ease of film formation, that the cation radical of a hole-transporting compound is a chemical species wherein one electron is removed from a repetitive unit of a macromolecular aromatic tertiary amine compound whose weight-average molecular weight is 1000 or higher and 1000000 or lower. As the corresponding macromolecular aromatic tertiary amine compound can be cited those compounds described later in [II-2. hole-transporting compound]. Its preferable examples are also the same as described later.

[I-3. Others]

An ion radical compound of the present invention can be synthesized by mixing an ionic compound, which contains an anion shown in [I-1. counter anion] as a counter anion ("electron-accepting ionic compound" described later), with a hole-transporting compound described later in [II-2. hole-transporting compound]. It dissolves easily in various solvents.

The molecular weight of an ion radical compound of the present invention, except when the cation radical is derived from a macromolecular compound, is usually 300 or higher, preferably 500 or higher, more preferably 700 or higher, and is usually 9000 or lower, preferably 5000 or lower, more preferably 3000 or lower.

[II. Composition for a Charge-Transport Film]

A composition for a charge-transport film of the present invention is either one of the following:

(A) A composition comprising, at least, one or more ionic compound selected from the group consisting of the compounds expressed by the general formulae (1)-(3) described later and a charge-transporting compound (hole-transporting compound) (hereinafter referred to as composition for a charge-transport film (A) of the present invention, as appropriate);

(B) A composition comprising, at least, a cation radical of a hole-transporting compound and an ionic compound consisting of a counter anion expressed by the general formula (7) described previously (ion radical compound) (hereinafter referred to as composition for a charge-transport film (B) of the present invention, as appropriate).

A composition for a charge-transport film (A) and a composition for a charge-transport film (B) of the present invention are compositions which can be used widely as charge transport materials (composition for charge transport material). As these materials are usually made into a film and used as charge transport material film, namely as "charge-transport film", they will be referred to as a composition for a charge-transport film in this description.

A charge-transporting compound contained in a composition for a charge-transport film (B) of the present invention is also a hole-transporting compound usually. In this description, therefore, explanation will be given on the assumption that a charge-transporting compound is a hole-transporting compound, unless otherwise indicated.

[II-1. Ionic Compound]

An ionic compound contained in a composition for a charge-transport film of the present invention is a compound represented by the following general formulae (1)-(3). This ionic compound is, hereinafter, referred to as "electron-accepting ionic compound" for the sake of convenience.

[Chemical Formula 8]

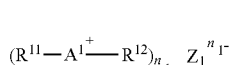

(1)

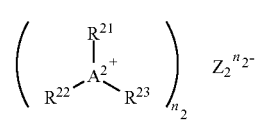

(2)

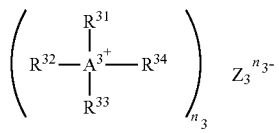

$$\left( R^{32} - \underset{R^{33}}{\overset{R^{31}}{A^{3+}}} - R^{34} \right)_{n_3} Z_3^{n_3-} \quad (3)$$

$R^{11}$, $R^{21}$ and $R^{31}$ in the general formulae (1)-(3) represent, independently of each other, an organic group bound to $A^1$-$A^3$, respectively, via a carbon atom. $R^{12}$, $R^{22}$, $R^{23}$ and $R^{32}$-$R^{34}$ represent, independently of each other, an arbitrary group; two or more neighboring groups of $R^{11}$-$R^{34}$ may combine together to form a ring.

Within the scope of the present invention, there is no special limitation on the kind of $R^{11}$, $R^{21}$ and $R^{31}$, on condition that they possess a carbon atom to bind them to $A^1$-$A^3$. The molecular weight of $R^{11}$, $R^{21}$ and $R^{31}$, including their substituents, is usually in the range of 1000 or lower, preferably 500 or lower. As preferable examples of $R^{11}$, $R^{21}$ and $R^{31}$ can be cited an alkyl group, alkenyl group, alkinyl group, aromatic hydrocarbon group and aromatic heterocyclic group, from the standpoint of delocalization of positive charge. Particularly preferable is an aromatic hydrocarbon group or an aromatic heterocyclic group from the standpoint of delocalization of positive charge and heat stability.

As aromatic hydrocarbon group is cited a univalent group derived from a 5- or 6-membered monocyclic ring or from a compound having 2 to 5 condensed rings, capable of delocalizing positive charge on the group. Examples include a univalent group derived from benzene, naphthalene, anthracene, phenanthrene, perylene, tetracene, pyrene, benzpyrene, chrysene, triphenylene, acenaphthene, and fluorene.

As aromatic heterocyclic group is cited a univalent group derived from a 5- or 6-membered monocyclic ring or from a compound having 2 to 5 condensed rings, capable of delocalizing positive charge on the group. As example of the ring structure can be cited a univalent group derived from furan, benzofuran, thiophen, benzothiophen, pyrrole, pyrazole, triazole, imidazole, oxadiazole, indole, carbazole, pyrroloimidazole, pyrrolopyrazole, pyrrolopyrole, thienopyrrole, thienothiophen, furopyrrole, furofuran, thienofuran, benzoisoxazole, benzoisothiazole, benzoimidazole, pyridine, pyrazine, pyridazine, pyrimidine, triazine, quinoline, isoquinoline, cinnoline, quinoxaline, phenanthridine, benzoimidazole, perimidine, quinazoline, quinazolinone, and azulene.

As alkyl group can be cited a straight chain, branched chain or cyclic alkyl group whose carbon number is usually one or more, and usually 12 or less, preferably 6 or less. Examples include methyl group, ethyl group, n-propyl group, 2-propyl group, n-butyl group, isobutyl group, tert-butyl group, and cyclohexyl group.

As alkenyl group can be cited a group whose carbon number is usually 2 or more, and usually 12 or less, preferably 6 or less. Examples include vinyl group, allyl group, and 1-butenyl group.

As alkinyl group can be cited a group whose carbon number is usually 2 or more, and usually 12 or less, preferably 6 or less. Examples include ethynyl group and propargyl group.

There is no special limitation on the kind of $R^{12}$, $R^{22}$, $R^{23}$ and $R^{32}$-$R^{34}$ insofar as it does not depart from the scope of the present invention. The molecular weight of $R^{12}$, $R^{22}$, $R^{23}$ and $R^{32}$-$R^{34}$, including its substituents, is usually in the range of 1000 or lower and preferably 500 or lower. Examples of $R^{12}$, $R^{22}$, $R^{23}$ and $R^{32}$-$R^{34}$ include alkyl, alkenyl, alkinyl, aromatic hydrocarbon, aromatic heterocyclic, amino, alkoxy, aryloxy, acyl, alkoxycarbonyl, aryloxycarbonyl, alkylcarbonyloxy, alkylthio, arylthio, sulfonyl, alkylsulfonyl, arylsulfonyl, cyano, hydroxyl, thiol, and silyl groups. Of these, organic groups having a carbon atom which binds them to $A^1$-$A^3$ is preferable because of their strong electron-accepting property similarly to the case of $R^{11}$, $R^{21}$ and $R^{31}$. Preferable examples of them include alkyl group, alkenyl group, alkinyul group, aromatic hydrocarbon group and aromatic heterocyclic group. Particularly preferable is an aromatic hydrocarbon group or aromatic heterocyclic group because of their heat stability in addition to its strong electron-accepting property.

As alkyl group, alkenyl group, alkinyl group, aromatic hydrocarbon group and aromatic heterocyclic group can be cited the same group as descried previously for $R^{11}$, $R^{21}$ and $R^{31}$.

Examples of amino group include alkylamino group, arylamino group and acylamino group.

As alkylamino group can be cited an alkylamino group having one or more alkyl groups whose carbon number is usually one or more, usually 12 or less and preferably 6 or less. Examples include methylamino, dimethylamino, diethylamino and benzylamino groups.

As arylamino group can be cited an arylamino group having one or more aromatic hydrocarbon groups or aromatic heterocyclic groups whose carbon number is usually 3 or more, preferably 4 or more and usually 25 or less, preferably 15 or less. Examples include phenylamino, diphenylamino, tolylamino, pyridylamino and thienylamino groups.

As acylamino group can be cited an acylamino group having one or more acyl groups whose carbon number is usually 2 or more and usually 25 or less, preferably 15 or less. Examples include acetylamino and benzoylamino groups.

As alkoxy group can be cited an alkoxy group whose carbon atoms are usually one or more and usually 12 or less, preferably 6 or less. Examples include methoxy, ethoxy, and butoxy groups.

As aryloxy group can be cited an aryloxy group having an aromatic hydrocarbon group or aromatic heterocyclic group whose carbon atoms are usually 3 or more, preferably 4 or more and 25 or less, preferably 15 or less. Examples include phenyloxy, naphthyloxy, pyridyloxy, and thienyloxy groups.

As acyl group can be cited an acyl group having usually one or more carbon atoms and usually 25 or less, preferably 15 or less carbon atoms. Examples include formyl, acetyl, and benzoyl groups.

As alkoxycarboyl group can be cited an alkoxycarbonyl group having usually 2 or more carbon atoms and usually 10 or less, preferably 7 or less carbon atoms. Examples include methoxycarbonyl and ethoxycarbonyl groups.

As aryloxycarbonyl group can be cited an aryloxycarbonyl group having an aromatic hydrocarbon group or aromatic heterocyclic group whose carbon atom is usually 3 or more, preferably 4 or more and usually 25 or less, preferably 15 or less. Examples include phenoxycarbonyl and pyridyloxycarbonyl groups.

As alkyloxycarbonyl group can be cited an alkyloxycarbonyl group having usually 2 or more carbon atoms and usually 10 or less, preferably 7 or less carbon atoms. Examples include acetoxy and trifluoroacetoxy groups.

As alkylthio group can be cited an alkylthio group having usually one or more carbon atoms and usually 12 or less, preferably 6 or less carbon atoms. Examples include methylthio and ethylthio groups.

As arylthio group can be cited an arylthio group having usually 3 or more, preferably 4 or more carbon atoms and usually 25 or less, preferably 14 or less carbon atoms. Examples include phenylthio, naphthylthio, and pyridylthio groups.

Examples of alkylsulfonyl and arylosulfonyl groups include mesyl and tosyl groups.

Examples of sulfonyloxy group include mesyloxy and tosyloxy groups.

Examples of silyl group include trimethylsilyl and triphenylsilyl groups.

Groups exemplified above as $R^{11}$, $R^{21}$, $R^{31}$ and $R^{12}$, $R^{22}$, $R^{23}$, $R^{32}$-$R^{34}$ may have additional substituents on them unless they depart from the scope of the present invention. There is no special limitation on the kind of the substituent. Examples include halogen atom, cyano group, thiocyano group, and nitro group, in addition to those exemplified above for $R^{11}$, $R^{21}$, $R^{31}$ and $R^{12}$, $R^{22}$, $R^{23}$, $R^{32}$-$R^{34}$. Preferable groups include alkyl group, alkenyl group, alkinyl group, alkoxy group, aryloxy group, aromatic hydrocarbon group and aromatic heterocyclic group because they do not hinder heat stability and electron-accepting property of ionic compounds (electron-accepting ionic compounds).

In the general formulae (1)-(3), $A^1$-$A^3$ represent an element belonging to the third and subsequent periods in the periodic table (3rd to 6th period). $A^1$ represents an element belonging to group 17 of the long form periodic table. $A^2$ represents an element belonging to group 16 of the long form periodic table. $A^3$ represents an element belonging to group 15 of the long form periodic table.

Of these, preferable is an element belonging to the fifth period or its preceding period of the periodic table (3rd to 5th period) from the standpoint of electron-accepting property and ease of availability. The preferable element for $A^1$ is one of iodine atom, bromine atom and chlorine atom. The preferable element for $A^2$ is one of tellurium atom, selenium atom and sulfur atom. The preferable element for $A^3$ is one of antimony atom, arsenic atom and phosphorus atom.

From the standpoint of electron-accepting property and chemical stability, preferable is an ionic compound in which $A^1$ in general formula (1) is a bromine atom or an iodine atom, and $A^2$ in general formula (2) is a selenium atom or a sulfur atom. Most preferable is an ionic compound in which $A^1$ in general formula (1) is an iodine atom.

In the general formulae (1)-(3), $Z_1^{n1-}$-$Z_3^{n3-}$ represent, independently of each other, a counter anion. There is no special limitation on the kind of the counter anion. It may be a single atom ion or a complex ion. However, a complex ion is more preferable than a single atom, because, as the size of a counter ion increases, negative charge is more delocalized and positive charge is delocalized accordingly, leading to greater electron-accepting property.

Also, n1-n3 represent, independently of each other, a positive integer corresponding to the valency of a counter anion $Z_1^{n1-}$-$Z_3^{n3}$. There is no special limitation on the value of n1-n3. However, the value of 1 or 2 is preferable for all of them and the value of 1 is most preferable.

Examples of $Z_1^{n1-}$-$Z_3^{n3-}$ include hydroxide ion, fluoride ion, chloride ion, bromide ion, iodide ion, cyanide ion, nitrate ion, nitrite ion, sulfate ion, sulfite ion, perchlorate ion, perbromate ion, periodate ion, chlorate ion, chlorite ion, hypochlorite ion, phosphate ion, phosphite ion, hypophosphite ion, borate ion, isocyanate ion, hydrosulfide ion, tetrafluoroborate ion, hexafluorophosphate ion, hexachloroantimonate ion; carboxylate ion such as acetate ion, trifluoroacetate ion and benzoate ion; sulfonate ion such as methane sulfonate ion and trifluoromethane sulfonate ion; and alkoxy ion such as methoxy ion and t-butoxy ion.

As counter anion $Z_1^{n1-}$-$Z_3^{n3-}$, a complex ion, expressed by the general formulae (4)-(6), is preferable, from the standpoint of chemical stability and solubility in solvents. A complex ion expressed by the general formula (6) is particularly preferable because it is large in size and, therefore, negative charge, and subsequently positive charge also, is delocalized, leading to large electron-accepting capacity.

[Chemical Formula 9]

(4)

(5)

(6)

$E^1$ and $E^3$ in the general formulae (4) and (6) represent, independently of each other, an element belonging to group 13 of the long form periodic table. Of those elements, boron atom, aluminum atom and gallium atom are preferable. Particularly preferable is a boron atom from the standpoint of chemical stability and ease of synthesis and purification.

$E^2$ in the general formula (5) represents an element belonging to group 15 of the long form periodic table. Of those elements, phosphorus atom, arsenic atom and antimony atom are preferable. Particularly preferable is a phosphorus atom from the standpoint of chemical stability, ease of synthesis and purification, and toxicity.

X in the general formulae (4) and (5) represents a halogen atom such as fluorine atom, chlorine atom and bromine atom. Fluorine atom and chlorine atom are preferable from the standpoint of chemical stability and ease of synthesis and purification. Most preferable is a fluorine atom.

$Ar^1$-$Ar^4$ in the general formula (6) represent, independently of each other, an aromatic hydrocarbon group or aromatic heterocyclic group. As examples of an aromatic hydrocarbon group and aromatic heterocyclic group can be cited a univalent group derived from a 5- or 6-membered monocyclic ring or from a compound having 2 to 4 condensed rings as the same examples cited previously for $R^{11}$, $R^{21}$, and $R^{31}$. Preferable among them, from the standpoint of chemical stability and heat stability, is a univalent group derived from a ring structure of benzene, naphthalene, pyridine, pyrazine, pyridazine, pyrimidine, triazine, quinoline, or isoquinoline.

Aromatic hydrocarbon group and aromatic heterocyclic group, exemplified as $Ar^1$-$Ar^4$, may carry additional substituent unless they depart from the scope of the present invention. There is no special limitation on the kind of the substituent and any substituent is possible. However, it is preferably an electron-accepting group.

An electron-accepting group preferable as substituent of $Ar^1$-$Ar^4$ includes: halogen atom such as fluorine atom, chlorine atom and bromine atom; cyano group; thiocyano group; nitro group; alkylsulfonyl group such as mesyl group; arylsulfonyl group such as tosyl group; acyl group containing usually one or more carbon atoms and usually 12 or less, preferably 6 or less carbon atoms such as formyl group, acetyl group and benzoyl group; alkoxycarbonyl group containing usually 2 or more carbon atoms and usually 10 or less, preferably 7 or less carbon atoms such as methoxycarbonyl group and ethoxycarbonyl group; aryloxycarbonyl group containing aromatic hydrocarbon group or aromatic heterocyclic group having usually 3 or more, preferably 4 or more carbon atoms and usually 25 or less, preferably 15 or less carbon atoms, such as phenoxycarbonyl group and pyridyloxycarbonyl group; aminocarbonyl group; aminosulfonyl group; haloalkyl group with straight chain, branched chain or cyclic alkyl group containing usually one or more, usually 10 or less, preferably 6 or less carbon atoms and having halogen substituents such as fluorine or chlorine atoms, examples of which haloalkyl group include trifluoromethyl group and pentafluoroethyl group.

In particular, it is preferable that at least one group of $Ar^1$-$Ar^4$ has one or more fluorine or chlorine atoms as substituent. It is most preferable that all the hydrogen atoms of $Ar^1$-$Ar^4$ are replaced with fluorine atoms giving a perfluoroaryl group, from the standpoint of efficient delocalization of negative charge and suitable sublimation property. Examples of perfluoroaryl group include pentafluorophenyl group, heptafluoro-2-naphtyl group, and tetrafluoro-4-pyridyl group.

The molecular weight of an electron-accepting ionic compound of the present invention is usually 100 or larger, preferably 300 or larger, and more preferably 400 or larger. It is usually 5000 or smaller, preferably 3000 or smaller, and more preferably 2000 or smaller. If the molecular weight of an electron-accepting ionic compound is too small, delocalization of negative and positive charge is insufficient, leading to lower electron-accepting capacity. If the molecular weight of an electron-accepting ionic compound is too large, an electron-accepting ionic compound itself may hinder charge transport.

Examples of electron-accepting ionic compounds, which are used in the present invention, will be cited below. It is to be understood that they are cited as examples and by no means restrictive.

TABLE 1

$$(R^{11}-A^{1+}-R^{12})_{n_1} Z_1^{n_1-} \quad (1)$$

| Number | $A^1$ | $-R^{11}$ | $-R^{12}$ | $Z^{n-}$ |
|---|---|---|---|---|
| A-1 | I | 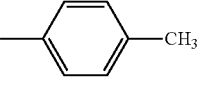 | 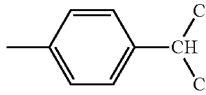 | 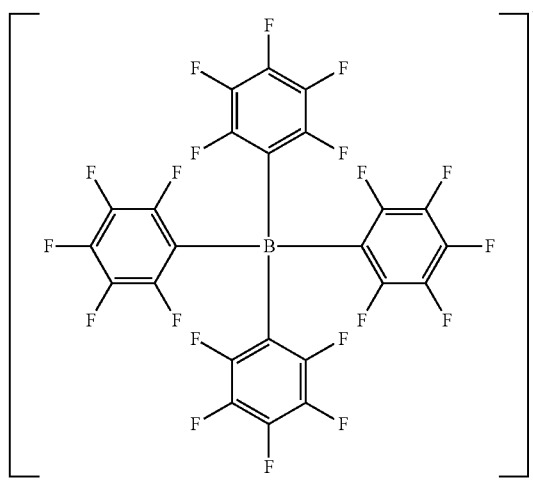 |
| A-2 | I | 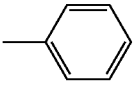 | 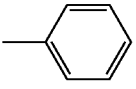 | 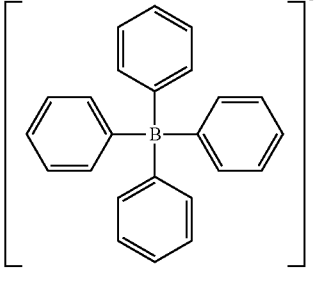 |
| A-3 | I | 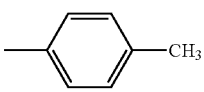 | 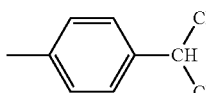 | 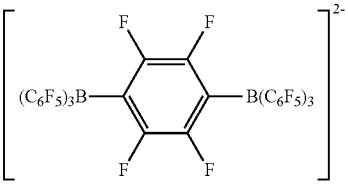 |

TABLE 1-continued $$(R^{11}-A^{1+}-R^{12})_{n_1} Z_1^{n_1-} \quad (1)$$

| Number | $A^1$ | $-R^{11}$ | $-R^{12}$ | $Z^{n-}$ |
|---|---|---|---|---|
| A-4 | I | –C$_6$H$_4$–CH$_3$ (p-tolyl) | –C$_6$H$_4$–CH(CH$_3$)$_2$ (p-cumyl) | [Ga(C$_6$F$_5$)$_4$]$^-$ |
| A-5 | I | –C$_6$H$_5$ | –C$_6$H$_5$ | PF$_6^-$ |
| A-6 | I | –C$_6$H$_5$ | –C$_6$H$_5$ | SbF$_6^-$ |
| A-7 | I | –C$_6$H$_4$–CH(CH$_3$)$_2$ | –C$_6$H$_4$–CH(CH$_3$)$_2$ | BF$_4^-$ |
| A-8 | I | –C$_6$H$_4$–CH$_3$ | –1-naphthyl | ClO$_4^-$ |
| A-9 | I | –C$_6$H$_5$ | –C$_6$H$_5$ | I$^-$ |
| A-10 | I | –C$_6$H$_5$ | –C$_6$H$_5$ | CF$_3$SO$_3^-$ |
| A-11 | I | –C$_6$H$_4$–CH$_2$CH$_3$ | –C$_6$H$_4$–CH$_2$CH$_3$ | CH$_3$CO$_2^-$ |
| A-12 | I | –2-naphthyl | –C$_6$H$_5$ | AsF$_6^-$ |

TABLE 1-continued
$$(R^{11}-A^{1+}-R^{12})_{n_1} Z_1^{n_1-} \tag{1}$$
| Number | $A^1$ | $-R^{11}$ | $-R^{12}$ | $Z^{n-}$ |
|---|---|---|---|---|
| A-13 | I | 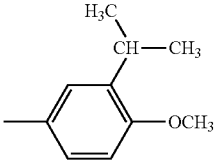 | 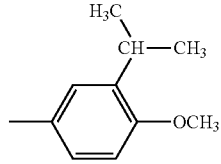 | $BF_4^-$ |
| A-14 | I | 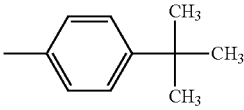 | 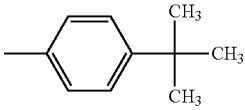 | 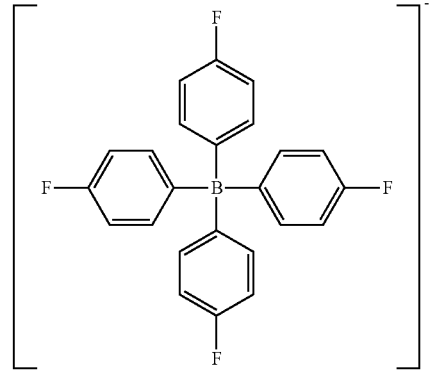 |
TABLE 2
| Number | $A^1$ | $-R^{11}$ | $-R^{12}$ | $Z^{n-}$ |
|---|---|---|---|---|
| A-15 | I | 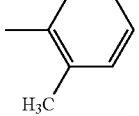 | 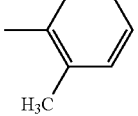 | $NO_3^-$ |
| A-16 | I | 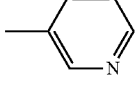 | 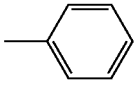 | 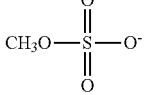 |
| A-17 | I | 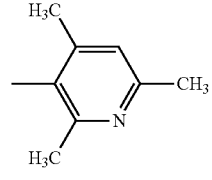 | 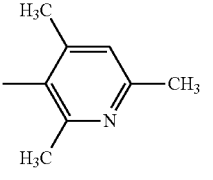 | $PF_6^-$ |
| A-18 | I | 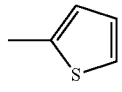 | 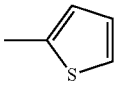 | 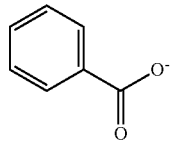 |

TABLE 2-continued

| Number | A¹ | —R¹¹ | —R¹² | $Z^{n-}$ |
|---|---|---|---|---|
| A-19 | I | –C₆H₄–OCH₃ (para) | –C₆H₄–OCH₃ (para) | [B(C₆F₅)₄]⁻ (tetrakis(pentafluorophenyl)borate) |
| A-20 | I | –C₆H₄–Cl (para) | –C₆H₄–Cl (para) | $GaF_4^-$ |
| A-21 | I | –C₆H₅ | –C₆H₄–F (para) | $IO_3^-$ |
| A-22 | I | –C₆H₅ | 2-quinolinyl | $Cl^-$ |
| A-23 | I | –C₆H₄–CH₃ (meta) | –C₆H₄–NO₂ (para) | $Br^-$ |
| A-24 | I | 2-naphthyl | 2-naphthyl | $PF_6^-$ |
| A-25 | I | –C₆H₄–OCH₃ (meta) | –C₆H₅ | $CF_3CO_2^-$ |
| A-26 | I | –C₆H₄–C(=O)CH₃ (para) | –C₆H₅ | $F^-$ |
| A-27 | I | –C₆H₄–C(CH₃)₂–C₆H₅ (para) | –C₆H₄–C(CH₃)₂–C₆H₅ (para) | $SO_4^{2-}$ |
| A-28 | I | 4-pyridyl | 4-pyridyl | $NO_3^-$ |

TABLE 2-continued

| Number | A¹ | —R¹¹ | —R¹² | $Z^{n-}$ |
|---|---|---|---|---|
| A-29 | I | 1,3-dimethyl-2-(bicyclopentyl)phenyl group | phenyl | $BF_4^-$ |
| A-30 | I | 4-bromo-2-methylthiophen-5-yl | 4-bromo-2-methylthiophen-5-yl | $ClO_4^-$ |
| A-31 | I | phenanthren-9-yl | 4-methylphenyl | [Ga(C₆F₅)₄]⁻ |

TABLE 3

| Number | A¹ | —R¹¹ | —R¹² | $Z^{n-}$ |
|---|---|---|---|---|
| A-32 | I | 4-isopropylphenyl | 4-isopropylphenyl | $NO_3^-$ |
| A-33 | I | phenyl | pentafluorophenyl | $PF_6^-$ |
| A-34 | I | 4-methylphenyl | 4-methylphenyl | $Cl^-$ |
| A-35 | I | 4-(trimethylsilyl)phenyl | 4-(trimethylsilyl)phenyl | $CF_3CF_2SO_3^-$ |
| A-36 | I | biphenyl-4-yl | biphenyl-4-yl | benzenesulfonate |

TABLE 3-continued
| Number | A¹ | —R¹¹ | —R¹² | Z$^{n-}$ |
|---|---|---|---|---|
| A-37 | I | —CH₃ | 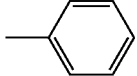 | 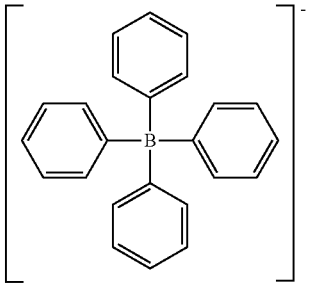 |
| A-38 | I | 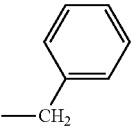 | 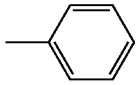 | NO₃⁻ |
| A-39 | I | 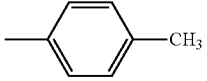 | —CH=CH₂ | ClO₄⁻ |
| A-40 | I |  | —CH₂—C≡CH | 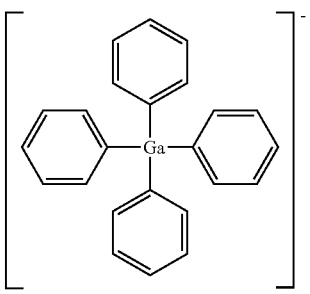 |
| A-41 | I | 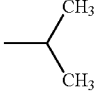 | 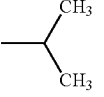 | PF₆⁻ |
| A-42 | I | —CF₂CF₃ | 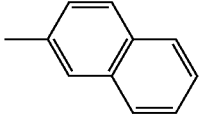 | 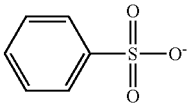 |
| A-43 | I | 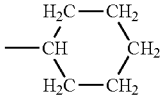 | 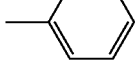 | I⁻ |
| A-44 | I | —CF₃ | 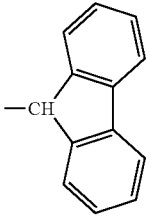 | BF₄⁻ |
| A-45 | I | 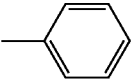 | —CF₂CF₂CF₃ | CF₃SO₃⁻ |

TABLE 3-continued
| Number | A$^1$ | —R$^{11}$ | —R$^{12}$ | Z$^{n-}$ |
|---|---|---|---|---|
| A-46 | I | 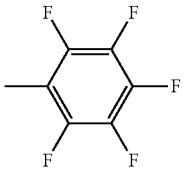 | —CF$_3$ | GaF$_4^-$ |
| A-47 | I | 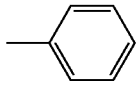 | —CF$_2$CF$_2$CF$_2$CF$_2$CF$_2$CF$_3$ | 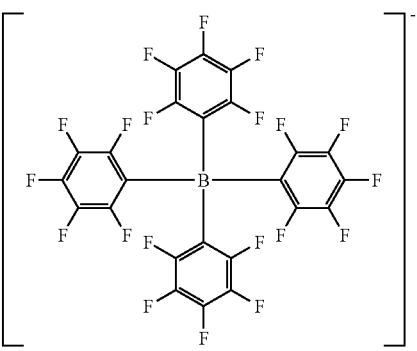 |
| A-48 | I | 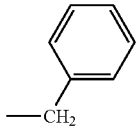 | —CH$_3$ | Br– |
TABLE 4
| Number | A$^1$ | —R$^{11}$ | —R$^{12}$ | Z$^{n-}$ |
|---|---|---|---|---|
| A-49 | I | 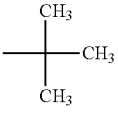 | 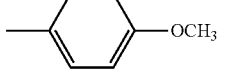 | BrO$_4^-$ |
| A-50 | I | —CH$_2$CH$_3$ | 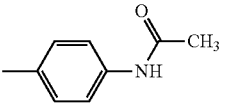 | NO$_2^-$ |
| A-51 | I | 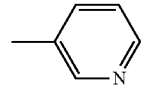 | 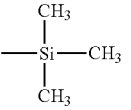 | CF$_3$SO$_3^-$ |
| A-52 | I | —CH$_2$—CH=CH$_2$ | 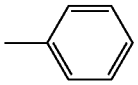 | PO$_4^{3-}$ |
| A-53 | I | —CH$_2$—O—CH$_3$ | 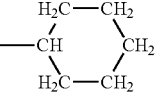 | OH$^-$ |
| A-54 | I | 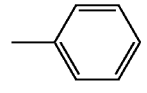 | 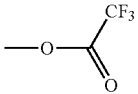 | CF$_3$CO$_2^-$ |

TABLE 4-continued

| Number | A¹ | —R¹¹ | —R¹² | Z$^{n-}$ |
|---|---|---|---|---|
| A-55 | I | phenyl | —O-C(=O)-CH₃ | CH₃CO₂⁻ |
| A-56 | I | phenyl | —OH | 4-methylbenzenesulfonate (tosylate) |
| A-57 | I | —OCH₂CH₃ | 4-methoxyphenyl | BF₄⁻ |
| A-58 | I | 2,4,6-trimethylphenyl | —O-C(=O)-CH₃ | PF₆⁻ |
| A-59 | I | 1-naphthyl | —OH | OH⁻ |
| A-60 | I | 2,3,4,5,6-pentafluorophenyl | —O-C(=O)-CF₃ | CF₃CO₂⁻ |
| A-61 | I | 2,3-(tetramethylene)-5-methylphenyl | —O-C(=O)-C₆H₅ | NO₃⁻ |
| A-62 | I | phenyl | —O-SO₂-C₆H₄-CH₃ | 4-methylbenzenesulfonate |
| A-63 | I | —CH₂CH₃ | —NH-C(=O)-CH₃ | SbF₆⁻ |
| A-64 | I | 4-methylphenyl | —OCH₃ | [(C₆F₅)₃B-C₆F₄-B(C₆F₅)₃]²⁻ |
| A-65 | Br | phenyl | phenyl | BF₄⁻ |

TABLE 4-continued
| Number | A¹ | —R¹¹ | —R¹² | Z$^{n-}$ |
|---|---|---|---|---|
| A-66 | Br | 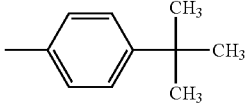 | 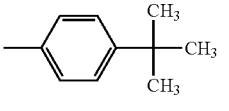 | PF$_6^-$ |
| A-67 | Br | 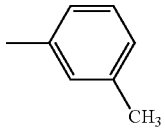 | 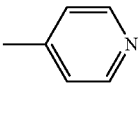 | Br$^-$ |
| A-68 | Br | 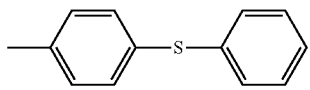 | 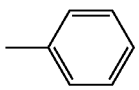 | CF$_3$CF$_2$SO$_3^-$ |
TABLE 5
| Number | A¹ | —R¹¹ | —R¹² | Z$^{n-}$ |
|---|---|---|---|---|
| A-69 | Br | 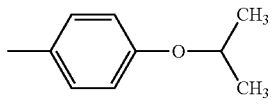 | 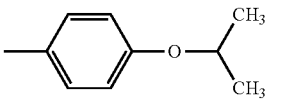 | 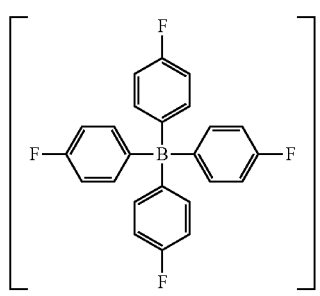 |
| A-70 | Br | 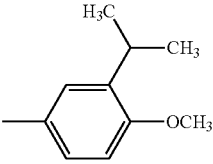 | 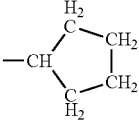 | ClO$_4^-$ |
| A-71 | Br | 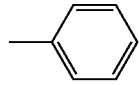 | —CH$_2$—CH=CH—CH$_3$ | GaF$_4^-$ |
| A-72 | Br | 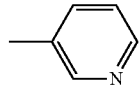 | —CF$_2$CF$_2$CF$_3$ | SO$_4^{2-}$ |
| A-73 | Br | 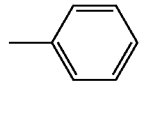 | 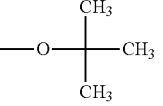 | CF$_3$CO$_2^-$ |
| A-74 | Br | —CH=CH$_2$ | 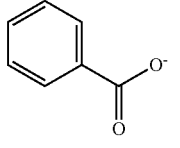 | 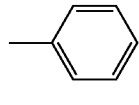 |
| A-75 | Cl | 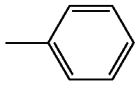 | | PF$_6^-$ |

TABLE 5-continued

| | | | | |
|---|---|---|---|---|
| A-76 | Cl | —CH$_2$CH$_3$ | pentafluorophenyl | Cl$^-$ |
| A-77 | Cl | phenyl | 4-methylphenyl | CF$_3$CO$_2^-$ |

$$(R^{11}-A^{1+}-R^{12})_{n_1}Z_1^{n_1-} \quad (1)$$

| Number | R$^{11}$—A$^{1+}$—R$^{12}$ | Z$^{n-}$ |
|---|---|---|
| A-79 | [fluorenyl cation]$^+$ | SO$_4^{2-}$ |
| A-80 | [fluorenyl cation]$^+$ | [tetrakis(pentafluorophenyl)borate]$^-$ |
| A-81 | [9-bromofluorenyl cation]$^+$ | BF$_4^-$ |
| A-82 | [3,6-dimethylfluorenyl cation]$^+$ | PF$_6^-$ |
| A-83 | [benzofuranone cation]$^+$ | CF$_3$CO$_2^-$ |
| A-84 | [isoindolinone cation]$^+$ | 4-methylbenzenesulfonate |

TABLE 6
$$\left( \begin{matrix} R^{21} \\ A^{2+} \\ R^{22} \end{matrix} R^{23} \right)_{n_2} Z_2^{n_2-} \quad (2)$$
| Number | A² | —R²¹ | —R²² | —R²³ | Z^{n-} |
|---|---|---|---|---|---|
| B-1 | S | 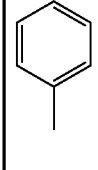 | 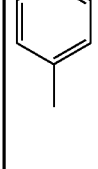 | 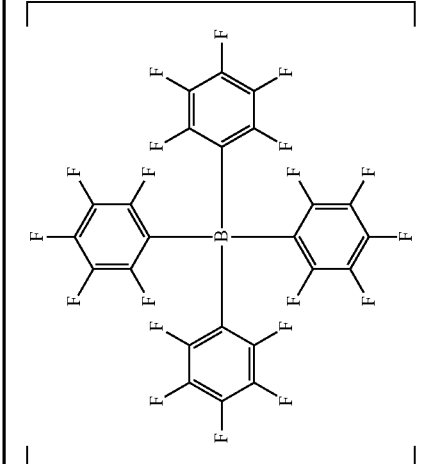 | 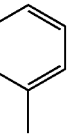 |
| B-2 | S | 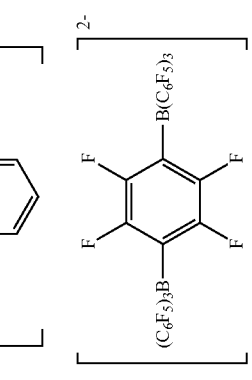 | 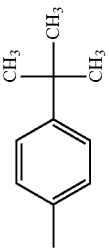 | 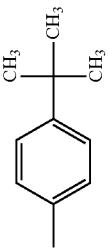 | 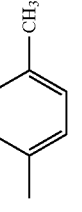 |
| B-3 | S | 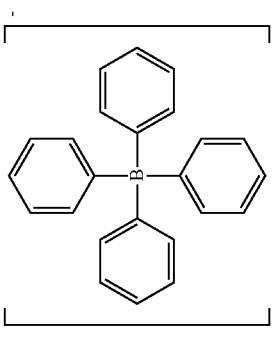 | 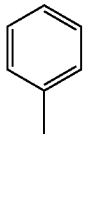 | 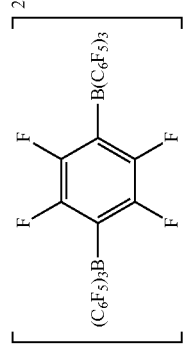 | |

TABLE 6-continued

| Number | $A^2$ | $-R^{21}$ | $-R^{22}$ | $-R^{23}$ | $Z^{n-}$ |
|---|---|---|---|---|---|
| B-4 | S | phenyl | 4-phenoxyphenyl | phenyl | $CF_3SO_3^-$ |
| B-5 | S | phenyl | phenyl | 2-naphthyl | $PF_6^-$ |
| B-6 | S | phenyl | 4-(methylthio)phenyl | $-CH_3$ | $CF_3SO_3^-$ |
| B-7 | S | 4-isopropylphenyl | phenyl | 4-methylphenyl | $BF_4^-$ |
| B-8 | S | phenyl | 1-naphthyl | phenyl | $ClO_4^-$ |
| B-9 | S | phenyl | phenyl | 4-(phenylthio)phenyl | $PF_6^-$ |

TABLE 6-continued
| Number | $A^2$ | $-R^{21}$ | $-R^{22}$ | $-R^{23}$ | $\left( \begin{array}{c} R^{21} \\ R^{22}-A^{2+}-R^{23} \end{array} \right)_{n_2} Z_2^{n_2^-}$ | $Z^{m-}$ |
|---|---|---|---|---|---|---|
| B-10 | S | 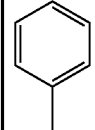 | 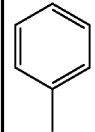 | 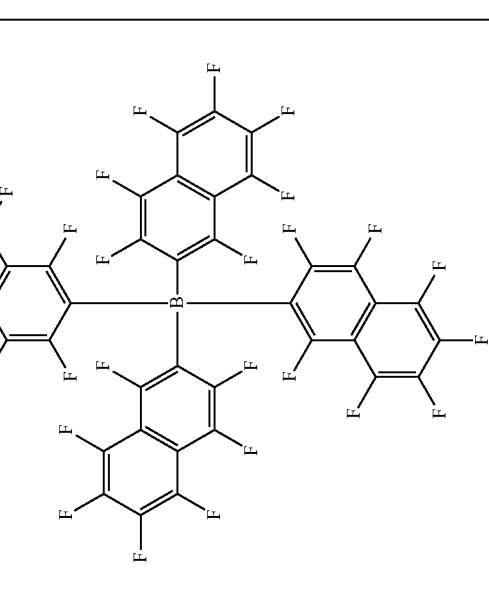 | | 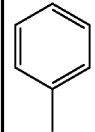 |
| B-11 | S | 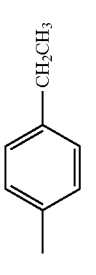 |  |  | | $CH_3CO_2^-$ |

TABLE 6-continued

| Number | $A^2$ | $-R^{21}$ | $-R^{22}$ | $-R^{23}$ | $Z^{n-}$ |
|---|---|---|---|---|---|
| B-12 | S | 4-bromophenyl | phenyl | phenyl | $AsF_6^-$ |
| B-13 | S | phenyl | phenyl | 2,4,6-trimethylphenyl | 4-methylbenzenesulfonate |
| B-14 | S | 2-methylphenyl | pentafluorophenyl | 2-methylphenyl | $NO_3^-$ |

TABLE 7
| Number | A² | —R²¹ | —R²² | —R²³ | Z$^{n-}$ |
|---|---|---|---|---|---|
| B-15 | S | 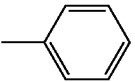 (—C₆H₄—CH₃) | —CH₂CH₂CH₂CH₃ | 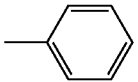 (—C₆H₅) | 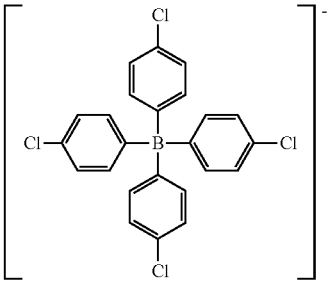 [B(C₆H₄Cl)₄]⁻ |
| B-16 | S | —CH₃ | —CH₃ | 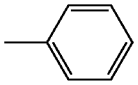 | PF₆⁻ |
| B-17 | S |  (—C₆H₄—Cl) | 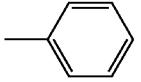 | 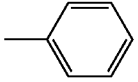 | Cl⁻ |
| B-18 | S | 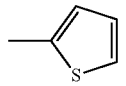 (2-thienyl) | 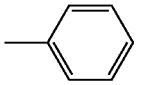 | 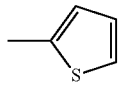 (2-thienyl) | 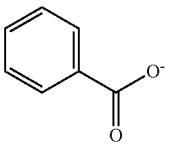 (PhCO₂⁻) |
| B-19 | S | 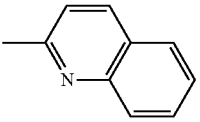 (2-quinolyl) | 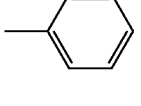 | 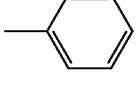 | GaF₄⁻ |
| B-20 | S |  (—C₆H₄—Cl) |  (—C₆H₄—Cl) | 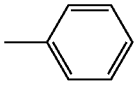 | NO₃⁻ |
| B-21 | S | 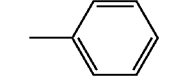 | —CH₂—CH=CH₂ | 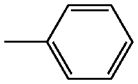 | CF₃CO₂⁻ |
| B-22 | S | 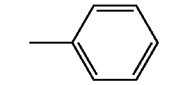 | 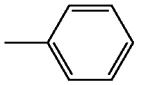 | —CH=CH₂ | Cl⁻ |
| B-23 | S | 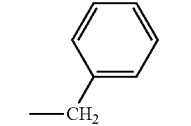 (—CH₂—C₆H₅) | 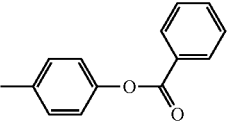 (—C₆H₄—O—CO—C₆H₅) | —CH₃ | SbF₆⁻ |
| B-24 | S | 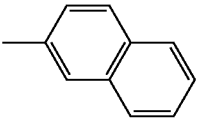 (2-naphthyl) | 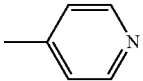 (4-pyridyl) | 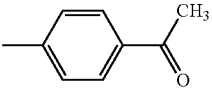 (—C₆H₄—COCH₃) | PF₆⁻ |
| B-25 | S | 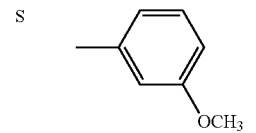 (3-OCH₃-C₆H₄—) | 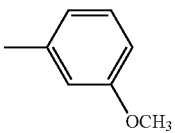 (3-OCH₃-C₆H₄—) | 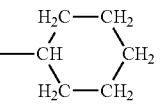 (cyclohexyl) | SO₄²⁻ |

TABLE 7-continued

| Number | A² | —R²¹ | —R²² | —R²³ | Zⁿ⁻ |
|---|---|---|---|---|---|
| B-26 | S | —CH₂CH₃ | 9H-fluoren-9-yl | —CH₂CH₃ | NO₃⁻ |
| B-27 | S | —C₆H₄—C(CH₃)₂—C₆H₅ | —CH(CH₃)₂ | —CH(CH₃)₂ | PF₆⁻ |
| B-28 | S | phenanthren-9-yl | —CH₂CH₂CH₂CH₃ | —CH₂CH₂CH₂CH₃ | BF₄⁻ |
| B-29 | S | —CH₃ | —CH₃ | —CH₂CH₂NH₂ | I⁻ |
| B-30 | S | —C₆H₅ | —C₆H₅ | —C₆H₅ | BF₄⁻ |
| B-31 | S | —C₆H₅ | —O—C(=O)—CF₃ | —C₆H₅ | CF₃CO₂⁻ |
| B-32 | Se | —C₆H₄—CH(CH₃)₂ | —C₆H₄—OCH₃ | —C₆H₄—OCH₃ | ClO₄⁻ |
| B-33 | Se | —C₆H₅ | —C₆H₅ | —C₆H₅ | PF₆⁻ |
| B-34 | Se | —C₆H₄—CH₃ | —CH₃ | —CH₃ | I⁻ |
| B-35 | Se | cyclohexyl | —C₆H₅ | cyclohexyl | CF₃CF₂SO₃⁻ |

TABLE 8

| Number | A² | —R²¹ | —R²² | —R²³ | Zⁿ⁻ |
|---|---|---|---|---|---|
| B-36 | Te | —C₆H₄—C₆H₅ (biphenyl) | —C₆H₅ | —C₆H₅ | PF₆⁻ |

TABLE 8-continued
| | | | | | |
|---|---|---|---|---|---|
| B-37 | Te | —CH$_3$ | 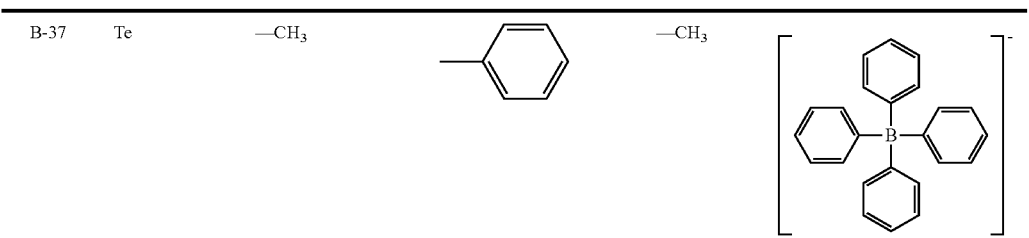 | —CH$_3$ | |
| B-38 | Te | 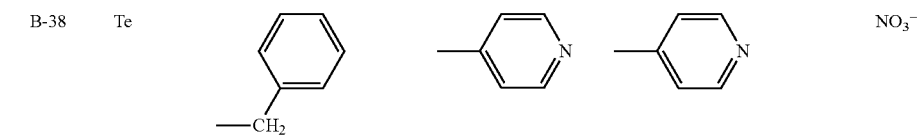 | | | NO$_3^-$ |
(2)
$$\left( R^{22} - \underset{R^{23}}{\overset{R^{21}}{\underset{|}{A^2}}}{}^+ \right)_{n_2} Z_2^{n_2-}$$
| Number | $R^{22}-\underset{R^{23}}{\overset{R^{21}}{\underset{|}{A^2}}}{}^+$ | $Z^{n-}$ |
|---|---|---|
| B-39 | 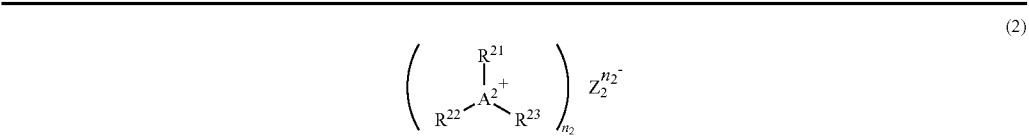 | |
| B-40 |  | |
| B-41 | 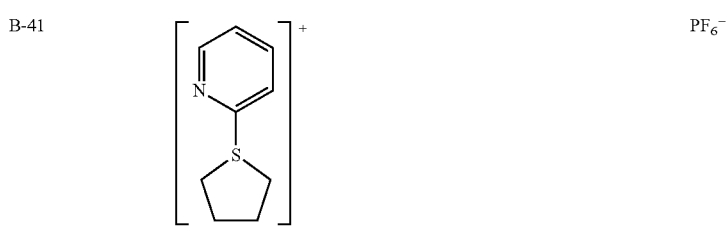 | PF$_6^-$ |
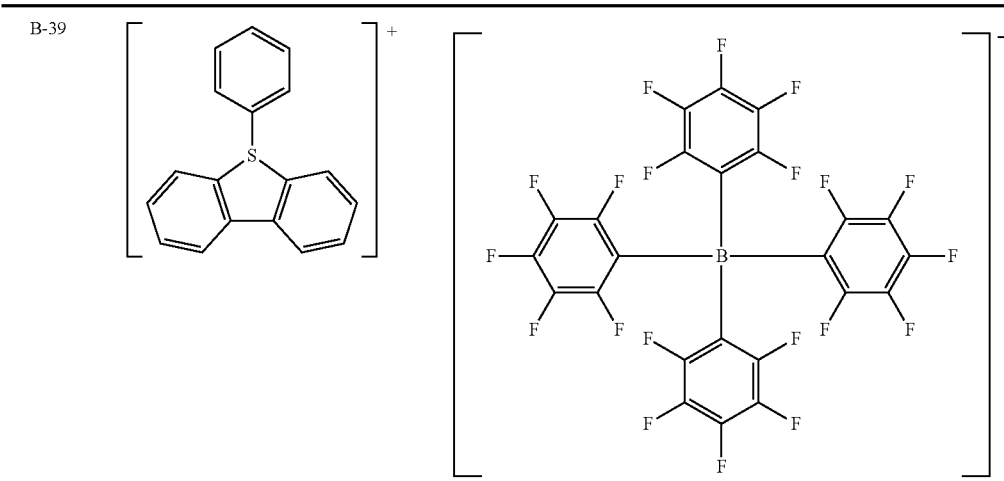
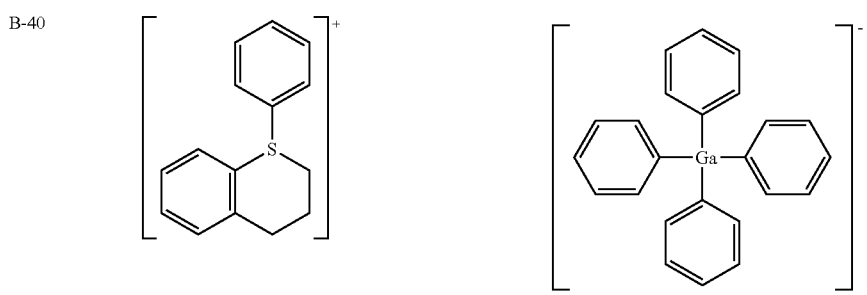

TABLE 8-continued
| B-42 | 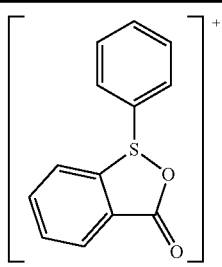 | $BF_4^-$ |
| B-43 | 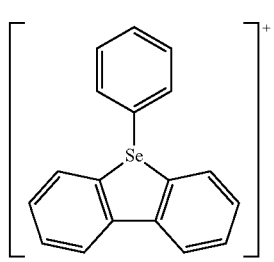 | $NO_3^-$ |

TABLE 9

(3)

$$\left( \begin{array}{c} R^{31} \\ R^{32}-A^3{-}^+R^{34} \\ R^{33} \end{array} \right)_{n_3} Z_3^{n_3-}$$

| Number | $A^3$ | $-R^{31}$ | $-R^{32}$ | $-R^{33}$ | $-R^{34}$ | $Z^{n-}$ |
|---|---|---|---|---|---|---|
| C-1 | P | phenyl | phenyl | phenyl | phenyl | tetrakis(pentafluorophenyl)borate |
| C-2 | P | 4-isopropylphenyl | 4-isopropylphenyl | 4-isopropylphenyl | 4-isopropylphenyl | $PF_6^-$ |
| C-3 | P | phenyl | phenyl | 2-methylnaphthyl | 2-methylnaphthyl | tetraphenylborate |

TABLE 9-continued (3)

$$R^{32}-\overset{R^{31}}{\underset{R^{33}}{A^3{}^+}}-R^{34} \Big)_{n_3} Z_3^{n_3{}^-}$$

| Number | A³ | —R³¹ | —R³² | —R³³ | —R³⁴ | Zⁿ⁻ |
|---|---|---|---|---|---|---|
| C-4 | P | phenyl | 4-methylphenylthio-phenyl | phenyl | 4-methylphenylthio-phenyl | CF₃SO₃⁻ |
| C-5 | P | —CH₃ | phenyl | phenyl | phenyl | BF₄⁻ |
| C-6 | P | phenyl | —CH₂—CH=CH₂ | phenyl | phenyl | ClO₄⁻ |
| C-7 | P | phenyl | phenyl | —CH₂—C≡CH | phenyl | PF₆⁻ |
| C-8 | P | phenyl | 1-naphthyl | phenyl | 1-naphthyl | AsF₆⁻ |
| C-9 | P | phenyl | phenyl | 4-methylphenylthio-phenyl | 4-methylphenylthio-phenyl | 4-methylbenzenesulfonate |

TABLE 9-continued
| Number | A³ | —R³¹ | —R³² | —R³³ | —R³⁴ | $Z^{n_3-}_3$ (3) |
|---|---|---|---|---|---|---|
| C-10 | P | 2-methylnaphthyl | phenyl | 2-methylnaphthyl | phenyl | 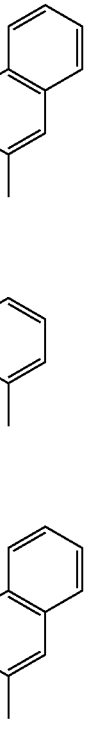 |
| C-11 | P | phenyl | phenyl | —C(=O)—CH₂—OCH₂CH₃ | phenyl | Cl⁻ |

TABLE 9-continued $$\left( R^{32}-\underset{R^{33}}{\overset{R^{31}}{\underset{|}{A^3}}}-R^{34}\right)_{n_3} Z_3^{n_3-} \quad (3)$$

| Number | $A^3$ | $-R^{31}$ | $-R^{32}$ | $-R^{33}$ | $-R^{34}$ | $Z^{n-}$ |
|---|---|---|---|---|---|---|
| C-12 | P | phenyl | phenyl | phenyl | benzyl | $AsF_6^-$ |
| C-13 | P | phenyl | $H_3C-N(CH_3)-CH_2-CH_2-$ (trimethylamino ethyl) | phenyl | phenyl | $Br^-$ |
| C-14 | P | 2-methylphenyl | pentafluorophenyl | 2-methylphenyl | 3,4,5-trimethylphenyl | $NO_3^-$ |

TABLE 10

| Number | A³ | —R³¹ | —R³² | —R³³ | —R³⁴ | Zⁿ⁻ |
|---|---|---|---|---|---|---|
| C-15 | P | Ph— | Ph— | Ph— | —CH=CH₂ | $CF_3CF_2SO_3^-$ |
| C-16 | P | —(CH₂)₅CH₃ | Ph— | Ph— | Ph— | $PF_6^-$ |
| C-17 | P | 4-Cl-C₆H₄— | Ph— | Ph— | —CH₂-(2-HO-C₆H₄) | $I^-$ |
| C-18 | P | —CH₃ | Ph— | Ph— | —CH₃ | $I^-$ |
| C-19 | P | Ph— | Ph— | 9H-fluoren-9-yl | Ph— | [B(4-F-C₆H₄)₄]⁻ |
| C-20 | P | —C(Ph)₃ | Ph— | Ph— | Ph— | $NO_3^-$ |
| C-21 | P | Ph— | Ph— | Ph— | Ph— | [BPh₄]⁻ |
| C-22 | P | Ph— | Ph— | —CH₂CH₃ | —CH₂CH₃ | $SO_4^{2-}$ |
| C-23 | P | Ph— | Ph— | Ph— | —N(CH₃)(Ph) | $PF_6^-$ |

TABLE 10-continued

| Number | A³ | —R³¹ | —R³² | —R³³ | —R³⁴ | Z$^{n-}$ |
|---|---|---|---|---|---|---|
| C-24 | P | phenyl | —O—C(CH₃)₃ (tert-butoxy) | phenyl | phenyl | ClO₄⁻ |
| C-25 | As | phenyl | phenyl | phenyl | phenyl | BF₄⁻ |
| C-26 | As | phenanthrenyl | phenyl | phenyl | phenyl | NO₃⁻ |
| C-27 | As | —CH(CH₃)₂ | phenyl | —CH(CH₃)₂ | phenyl | PF₆⁻ |
| C-28 | As | 4-pyridyl | 4-pyridyl | phenyl | phenyl | BF₄⁻ |
| C-29 | Sb | —CH₃ | —CH₃ | phenyl | phenyl | I⁻ |
| C-30 | Sb | phenyl | phenyl | phenyl | phenyl | BF₄⁻ |

TABLE 11

$$\left( \begin{array}{c} R^{31} \\ R^{32}-A^{3+}-R^{34} \\ R^{33} \end{array} \right)_{n_3} Z_3^{n_3-} \quad (3)$$

| Number | $\begin{array}{c} R^{31} \\ R^{32}-A^{3+}-R^{34} \\ R^{33} \end{array}$ | Z$^{n-}$ |
|---|---|---|
| C-31 | [9-phenyl-9-phosphafluorenyl diphenyl cation]⁺ | [B(C₆F₅)₄]⁻ |

TABLE 11-continued $$\left( \begin{array}{c} R^{31} \\ | \\ R^{32}-A^{3+}-R^{34} \\ | \\ R^{33} \end{array} \right)_{n_3} Z_3^{n_3-} \quad (3)$$

| Number | $R^{32}-\overset{R^{31}}{\underset{R^{33}}{A^{3+}}}-R^{34}$ | $Z^{n-}$ |
|---|---|---|
| C-32 | 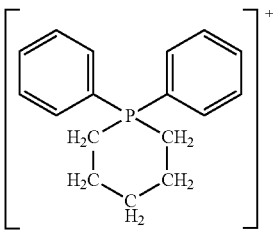 | $NO_3^-$ |
| C-33 | 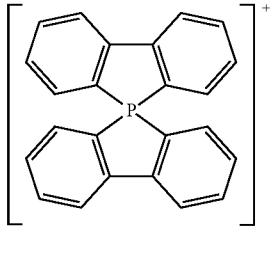 | 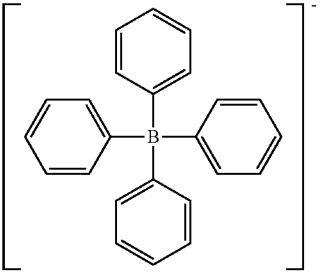 |
| C-34 | 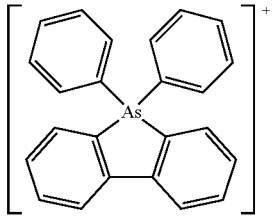 | $BF_4^-$ |

Of these examples, preferable from the standpoint of electron-accepting property, heat stability and solubility are such compounds as A-1 to A-48, A-54, A-55, A-60 to A-62, A-64 to A-75, A-79 to A-83, B-1 to B-20, B-24, B-25, B-27, B-30 to B-37, B-39 to B-43, C-1 to C-10, C-19 to C-21, C-25 to C-27, C-30 and C-31. More preferable are A-1 to A-9, A-12 to A-15, A-17, A-19, A-24, A-29, A-31 to A-33, A-36, A-37, A-65, A-66, A-69, A-80 to A-82, B-1-3, B-5, B-7 to B-10, B-16, B-30, B-33, B-39, C-1 to C-3, C-5, C-10, C-21, C-25 and C-31. Most preferable are A-1 to A-7 and A-80.

No particular limitation is imposed on the method of producing the above-mentioned electron-accepting ionic compounds. Various methods are available. As examples can be cited the methods described in Chem. Rev., Vol. 66, 243 (1966) and J. Org. Chem., Vol. 53, 5571 (1988).

A composition for a charge-transport film (A) of the present invention may contain any one kind of electron-accepting ionic compound described above or may contain two or more kinds of electron-accepting ionic compounds in any combination and in any ratio. In the case where it contains two or more kinds of electron-accepting ionic compounds, it may contain two or more kinds of such compounds belonging to any one of the general formulae (1)-(3), or it may contain two or more such compounds belonging to different formulae of the general formulae (1)-(3).

The content of electron-accepting ionic compound in a composition for a charge-transport film (A) of the present invention is usually 0.1 weight % or higher, preferably 1 weight % or higher, and usually 100 weight % or lower, preferably 40 weight % or lower, relative to hole-transporting compound described later. When the content of electron-accepting ionic compound is too low, the production of a free carrier (cation radical of hole-transporting compound) is insufficient. On the other hand, when the content of electron-accepting ionic compound is too high, charge transport capacity tends to decrease, which is not desirable either. When two or more kinds of electron-accepting ionic compounds are used together, their total content should fall within the range specified above.

[II-2. Hole Transporting Compound]

In the following, explanation will be given on the hole-transporting compound contained in the composition for a charge-transport film of the present invention (hereinafter referred to as hole-transporting compound of the present invention for short, as appropriate).

As the above hole-transporting compounds are preferable compounds having an ionization potential of between 4.5 eV and 5.5 eV, from the standpoint of hole transport capacity. The examples include aromatic amine compounds, phthalocyanine derivatives, porphyrine derivatives or oligothiophen derivatives. Particularly preferable are aromatic amine compounds, from the standpoint of amorphous nature, solubility in solvents and transmission of visible light.

Of aromatic amine compounds, aromatic tertiary amine compounds are particularly preferable in the present invention. Aromatic tertiary amine compounds in the present invention mean compounds possessing an aromatic tertiary amine structure and include compounds possessing a group derived from aromatic tertiary amines.

There is no special limitation on the kind of aromatic tertiary amine compound. However, from the standpoint of the smoothing effect on surface, macromolecular compounds having a weight-average molecular weight of 1000 or higher and 1000000 or lower are preferable.

As preferable macromolecular aromatic tertiary amine compound can be cited a macromolecular compound possessing a repetitive unit represented by the following formula (11).

[Chemical Formula 10]

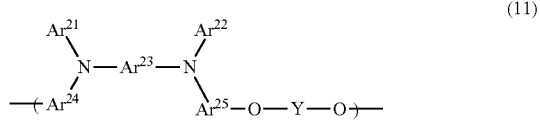

(11)

($Ar^{21}$ and $Ar^{22}$ in the formula (11) represent, independently of each other, an aromatic hydrocarbon group that may have substituents or an aromatic heterocyclic group that may have substituents.

$Ar^{23}$-$Ar^{25}$ represent, independently of each other, a bivalent aromatic hydrocarbon group that may have substituents or a bivalent aromatic heterocyclic group that may have substituents.

Y represents a connecting moiety selected from the following connecting group $Y^1$.)

[Chemical Formula 11]

Connecting group $Y^1$

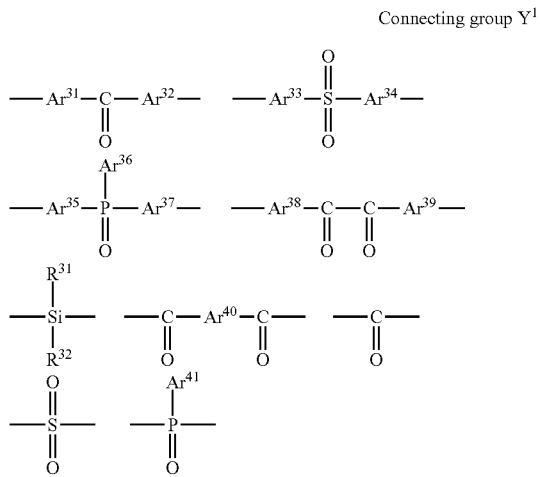

($Ar^{31}$-$Ar^{41}$ in the above formulae represent, independently of each other, a univalent group or bivalent group derived from an aromatic hydrocarbon ring that may have substituents or an aromatic heterocyclic ring that may have substituents.

$R^{31}$ and $R^{32}$ represent, independently of each other, a hydrogen atom or an arbitrary substituent.)

As $Ar^{21}$-$Ar^{25}$ and $Ar^{31}$-$Ar^{41}$, a univalent or bivalent group derived from an arbitrary aromatic hydrocarbon ring or aromatic heterocyclic ring can be applied. They may be one and the same group or may be different from one another. They may carry arbitrary substituents.

As aromatic hydrocarbon ring can be cited a 5- or 6-membered monocyclic ring or a ring structure having 2 to 5 condensed rings. Examples are various ring structures such as benzene, naphthalene, anthracene, phenanthrene, perylene, tetracene, pyrene, benzpyrene, chrysene, triphenylene, acenaphthene, fluoranthene, and fluorene rings.

As aromatic heterocyclic group can be cited a 5- or 6-membered monocyclic ring or a ring structure having 2 to 4 condensed rings. Examples of the ring structure include furan, benzofuran, thiophen, benzothiophen, pyrrole, pyrazole, imidazole, oxadiazole, indole, carbazole, pyrroloimidazole, pyrrolopyrazole, pyrrolopyrole, thienopyrrole, thienothiophen, furopyrrole, furofuran, thienofuran, benzoisoxazole, benzoisothiazole, benzimidazole, pyridine, pyrazine, pyridazine, pyrimidine, triazine, quinoline, isoquinoline, cinnoline, quinoxaline, phenanthridine, benzimidazole, perimidine, quinazoline, quinazolinone, and azulene rings.

Furthermore, as $Ar^{23}$-$Ar^{25}$, $Ar^{31}$-$Ar^{35}$ and $Ar^{37}$-$Ar^{40}$ can be used a group formed by linking two or more bivalent groups derived from one kind or more than one kind of aromatic hydrocarbon ring and/or aromatic heterocyclic ring.

An aromatic hydrocarbon ring and/or aromatic heterocyclic ring of $Ar^{21}$-$Ar^{41}$ may have additional substituents, insofar as it does not deviate from the scope of the present invention. The molecular weight of the substituent is usually 400 or lower, preferably 250 or lower. There is no special limitation on the kind of substituent. As example can be cited one or more substituents selected from the following substituent groups W.

[Substituent Groups W]

Alkyl group having usually one or more, and usually 10 or less, preferably 8 or less carbon atoms such as methyl group and ethyl group; alkenyl group having usually 2 or more, and usually 11 or less, preferably 5 or less carbon atoms such as vinyl group; alkinyl group having usually 2 or more, and usually 11 or less, preferably 5 or less carbon atoms such as ethynyl group; alkoxy group having usually one or more, and usually 10 or less, preferably 6 or less carbon atoms such as methoxy group and ethoxy group; aryloxy group having usually 4 or more, preferably 5 or more, and usually 25 or less, preferably 14 or less carbon atoms such as phenoxy group, naphthoxy group, and pyridyloxy group; alkoxycarbonyl group having usually 2 or more, and usually 11 or less, preferably 7 or less carbon atoms such as methoxycarbonyl group and ethoxycarbonyl group; dialkylamino group having usually 2 or more, and usually 20 or less, preferably 12 or less carbon atoms such dimethylamino group and diethylamino group; diarylamino group having usually 10 or more, preferably 12 or more, and usually 30 or less, preferably 22 or less carbon atoms such as diphenylamino group, ditolylamino group and N-carbazolyl group; arylalkylamino group having usually 6 or more, preferably 7 or more, and usually 25 or less, preferably 17 or less carbon atoms such as phenylmethylamino group; acyl group having usually 2 or more, and usually 10 or less, preferably 7 or less carbon atoms such as acetyl group and benzoyl group; halogen atom such as fluorine atom and chlorine atom; haloalkyl group having usually one or more, and usually 8 or less, preferably 4 or less carbon atoms such as trifluoromethyl group; alkylthio group having usually one or more, and usually 10 or less, preferably 6 or less carbon atoms such as methylthio group and ethylthio group; arylthio group having usually 4 or more, preferably 5 or more, and usually 25 or less, preferably 14 or less carbon atoms such as phenylthio group, naphthylthio group and pyridylthio group; silyl group having usually 2 or more, preferably 3 or more, and usually 33 or less, preferably 26 or less carbon atoms such as trimethylsilyl group and triphenylsilyl group; siloxy group having usually 2 or more, preferably 3 or more, and usually 33 or less, preferably 26 or less carbon atoms such as trimethylsiloxy group and triphenylsiloxy group; cyano group; aromatic hydrocarbon group having usually 6 or more, and usually 30 or less, preferably 18 or less carbon atoms such as phenyl group and naphthyl group; and aromatic heterocyclic group having usually 3 or more, preferably 4 or more, and usually 28 or less, preferably 17 or less carbon atoms such as thienyl group and pyridyl group.

Preferable as $Ar^{21}$ and $Ar^{22}$, from the standpoint of solubility, heat stability, and hole injection/transport property of a macromolecular compound, is a univalent group derived from a ring structure of benzene, naphthalene, phenanthrene, thiophene, and pyridine. Particularly preferable is phenyl group and naphthyl group.

Preferable as $Ar^{23}$-$Ar^{25}$, from the standpoint of heat stability and hole injection/transport property including oxidation/reduction potential, is a bivalent group derived from a ring structure of benzene, naphthalene, anthracene and phenanthrene. Particularly preferable is phenylene group, biphenylene group and naphthylene group.

A hydrogen atom or an arbitrary substituent can be applicable as $R^{31}$ and $R^{32}$. They can be one and the same substituent or can be different substituents. No particular limitation is imposed on the kind of the substituent insofar as they do not depart from the scope of the present invention. Examples of applicable substituent include an alkyl group, alkenyl group, alkinyl group, alkoxy group, silyl group, siloxy group, aromatic hydrocarbon group and aromatic heterocyclic group. Examples are various substituents exemplified in [Substituent group W].

Of macromolecular compounds having a repetitive unit shown in the formula (11), those compounds having a repetitive unit shown in formula (12) are preferable in particular, because they have excellent hole injection/transport property.

[Chemical Formula 12]

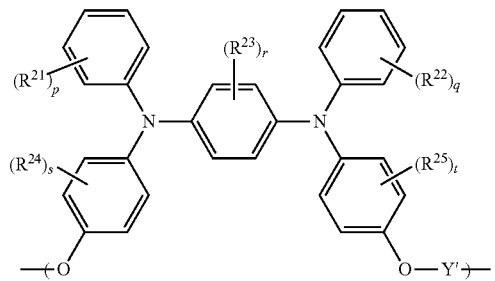

(12)

(In the formula (12),
$R^{21}$-$R^{25}$ represent, independently of each other, an arbitrary substituent, examples of substituents of $R^{21}$-$R^{25}$ being the same as described as possible substituents of $Ar^{21}$-$Ar^{25}$ in the formula (11) (namely, substituents described in [substituent group W]);

p and q represent, independently of each other, an integer which is 0 or larger and 5 or smaller; and r, s and t represent, independently of each other, an integer which is 0 or larger and 4 or smaller.

Y' represents a connecting moiety selected from the following connecting group $Y^2$.

[Chemical Formula 13]

Connecting group Y2

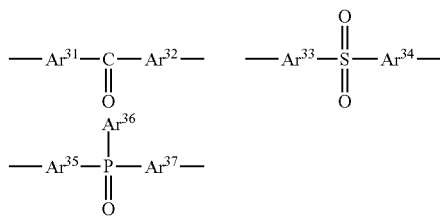

$Ar^-$-$Ar^{37}$ in the above formulae represent, independently of each other, a univalent or bivalent group derived from an aromatic hydrocarbon ring or aromatic heterocyclic ring that may have substituents. $Ar^{31}$-$Ar^{37}$ are the same as $Ar^{31}$-$Ar^{37}$ described above.

Preferable examples of a repetitive unit, which is represented by the formula (11) and can be applied in the present invention, will be explained below. The present invention is, though, not limited to these.

[Chemical Formula 14]

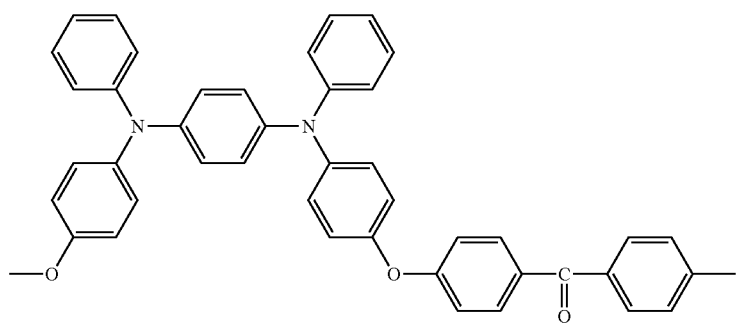

(P-1)

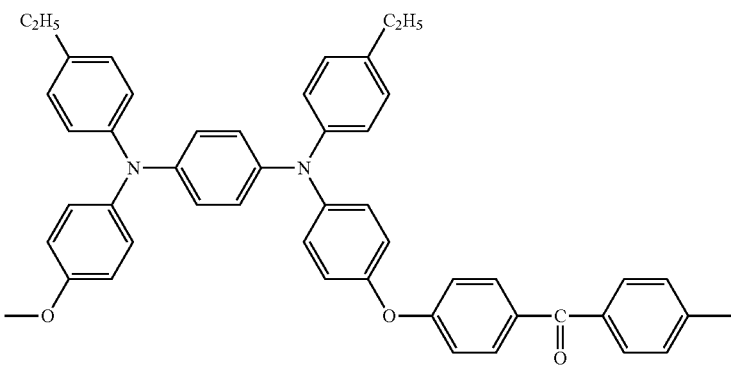
(P-2)
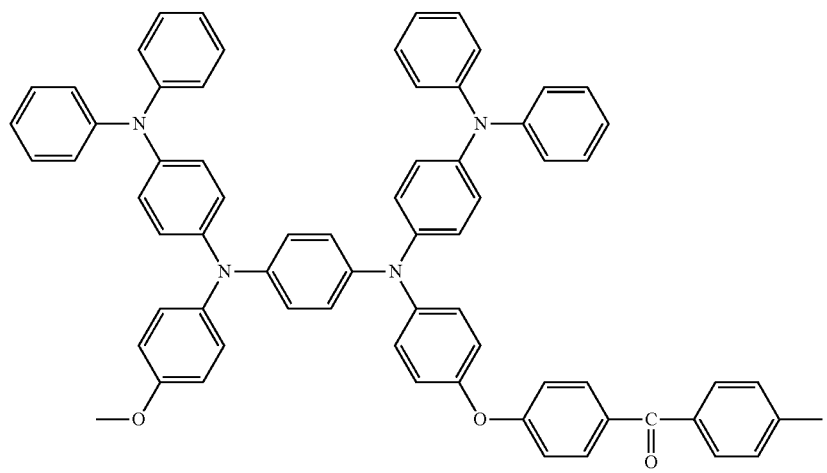
(P-3)
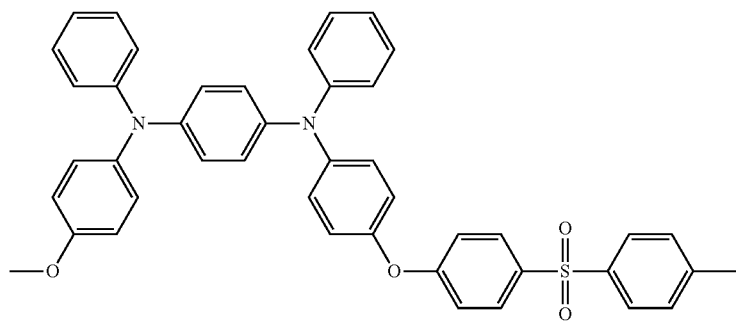
(P-4)
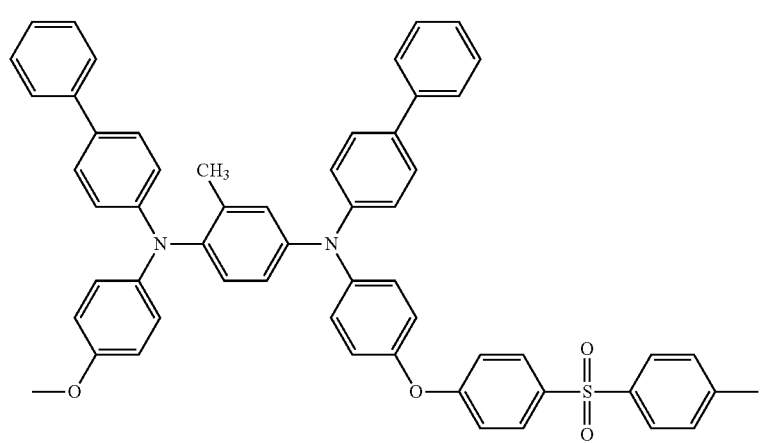
(P-5)

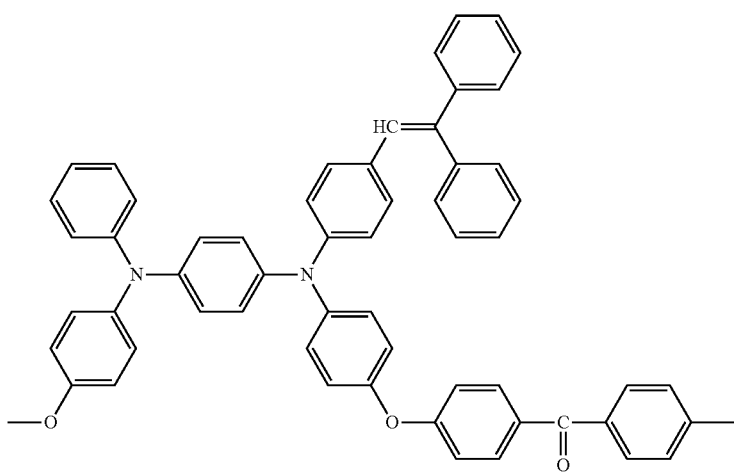
(P-6)
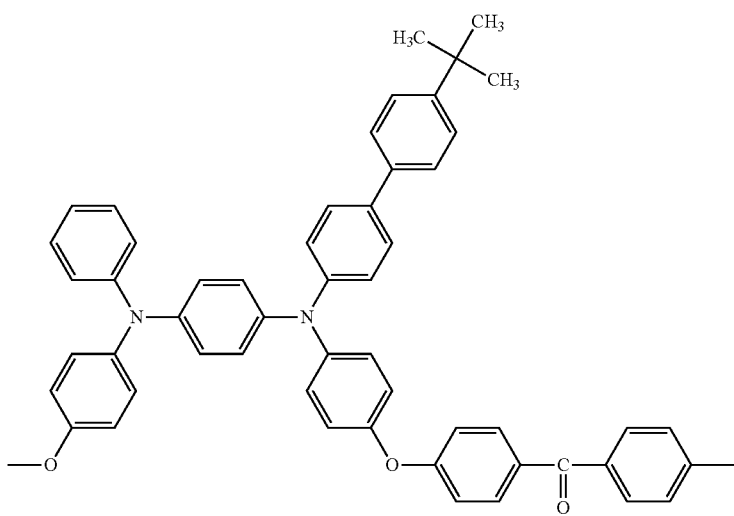
(P-7)
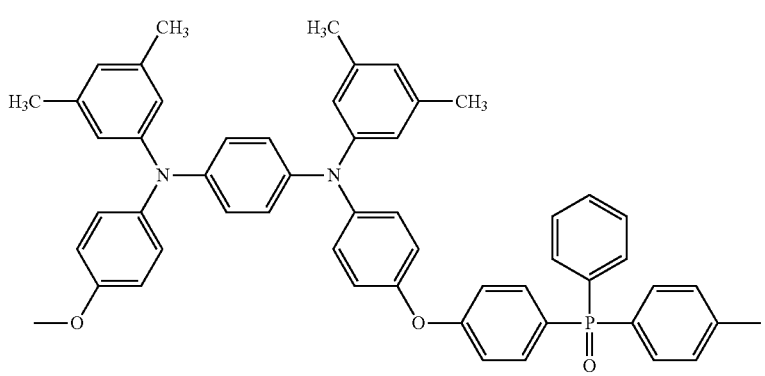
(P-8)

[Chemical Formula 15]
(P-9)
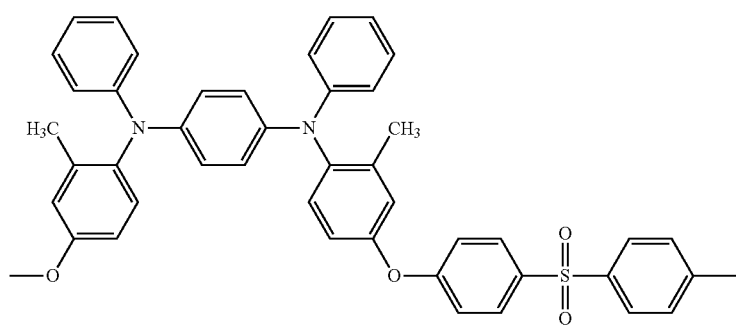
(P-10)
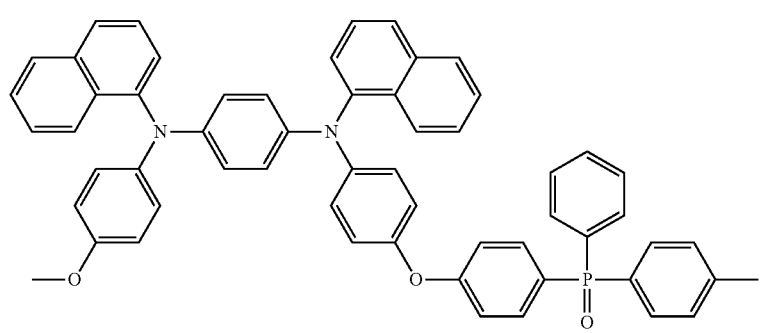
(P-11)
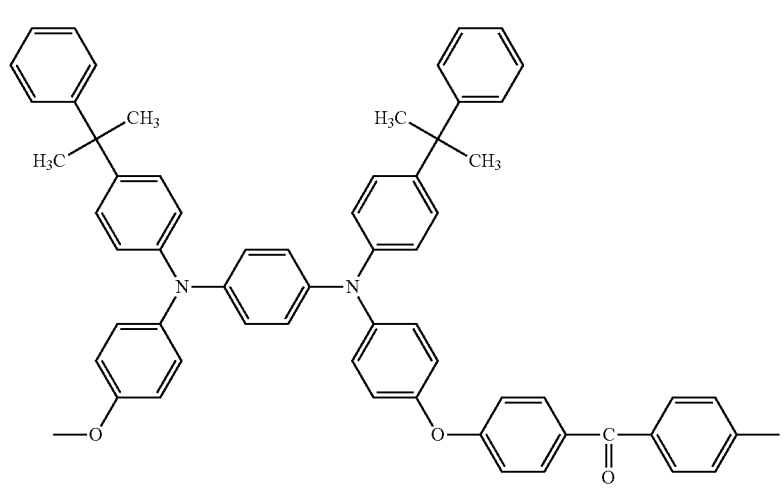
(P-12)
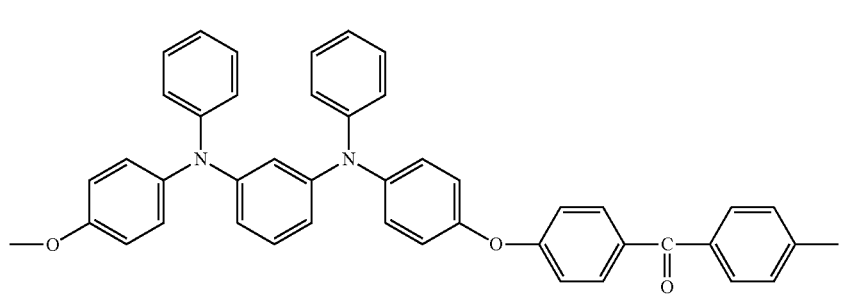

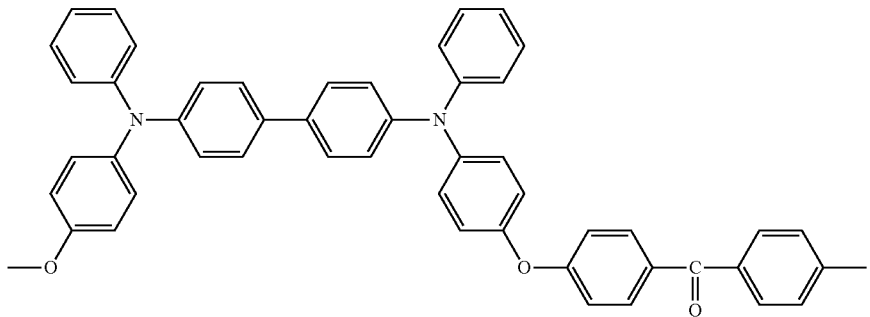
(P-13)
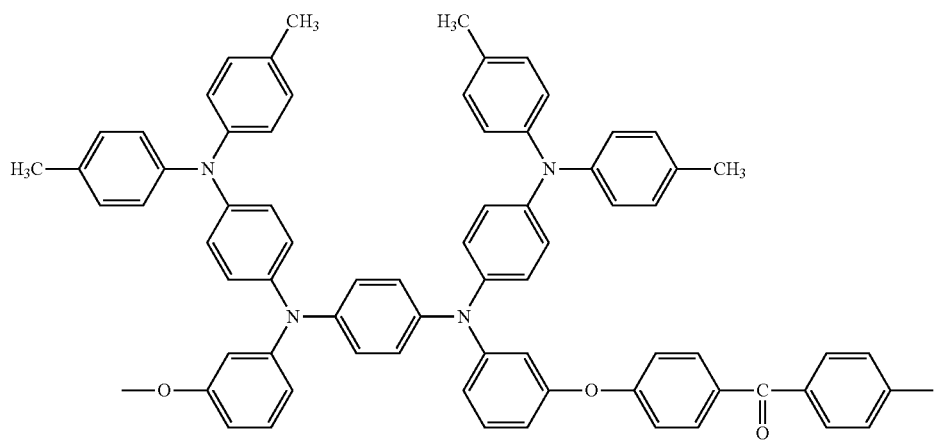
(P-14)
[Chemical Formula 16]
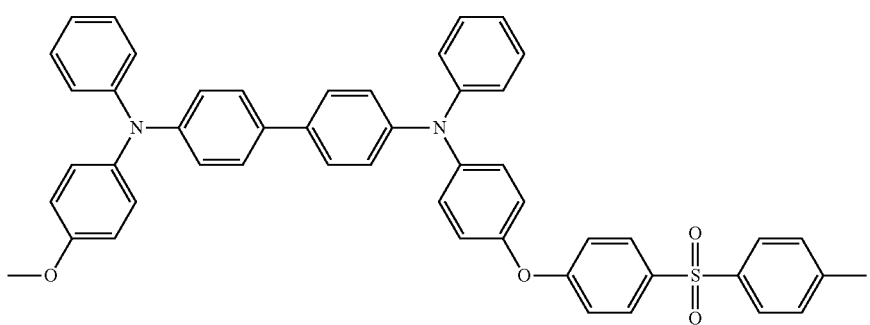
(P-15)

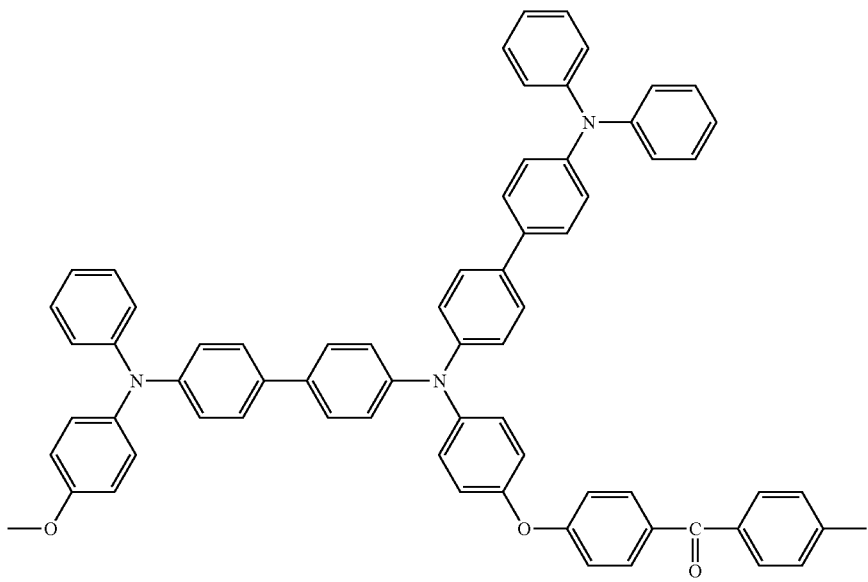
(P-16)
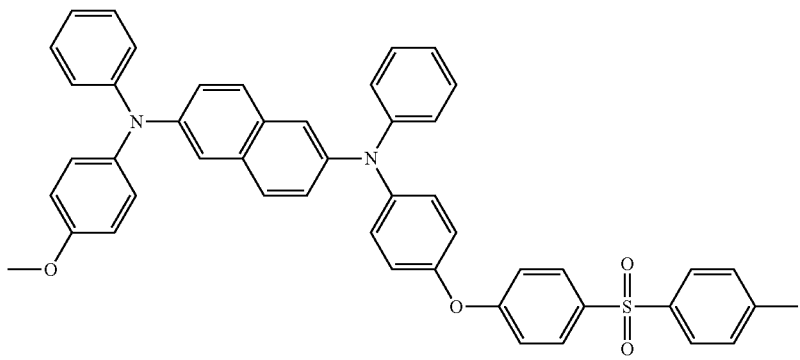
(P-17)
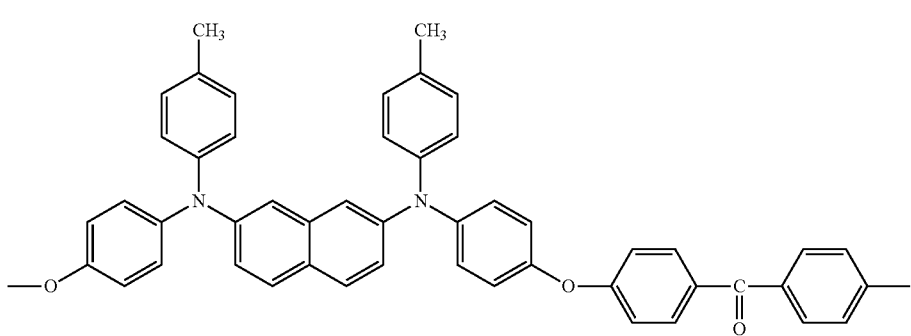
(P-18)
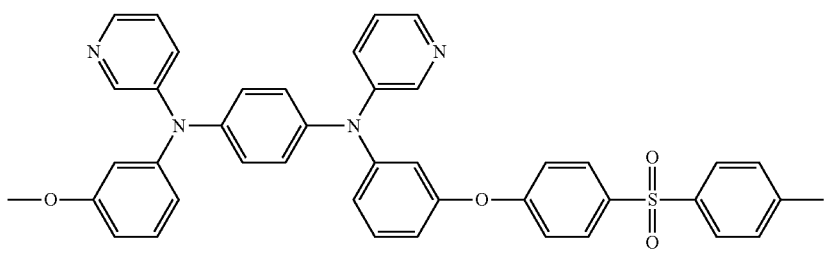
(P-19)

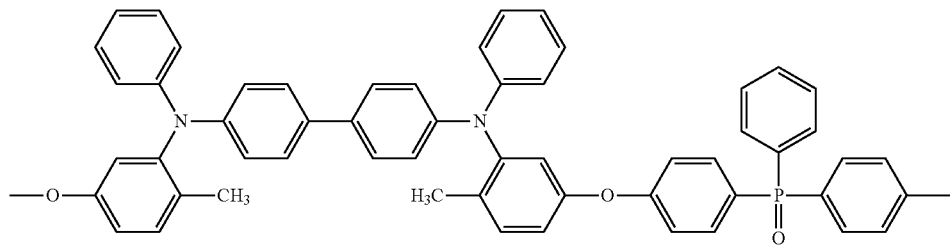
(P-20)
[Chemical Formula 17]
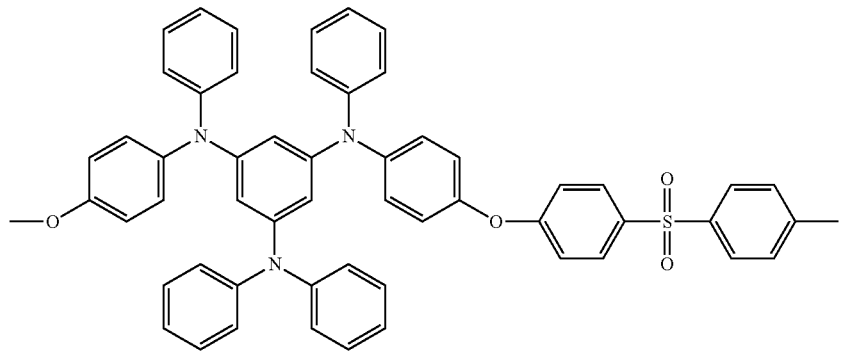
(P-21)
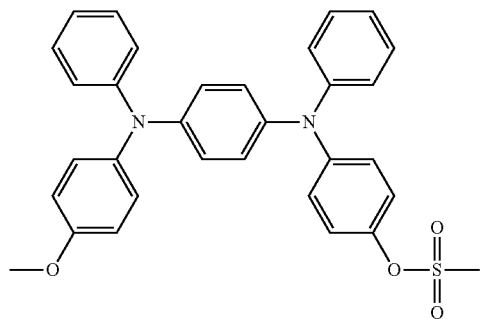
(P-22)
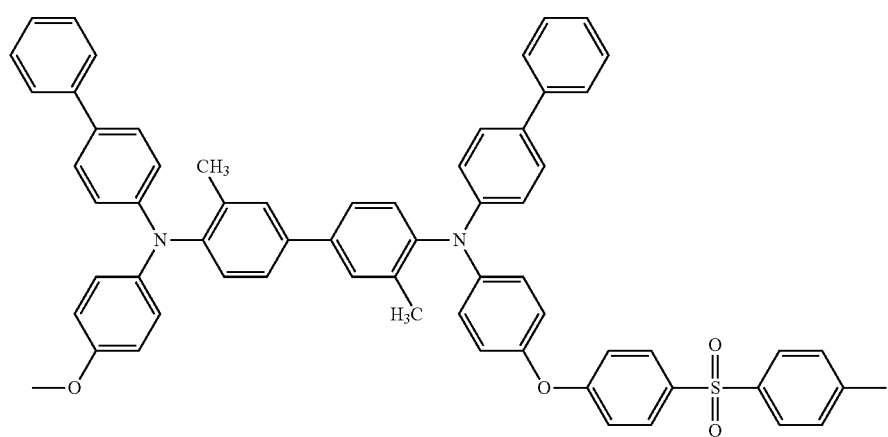
(P-23)

(P-24)

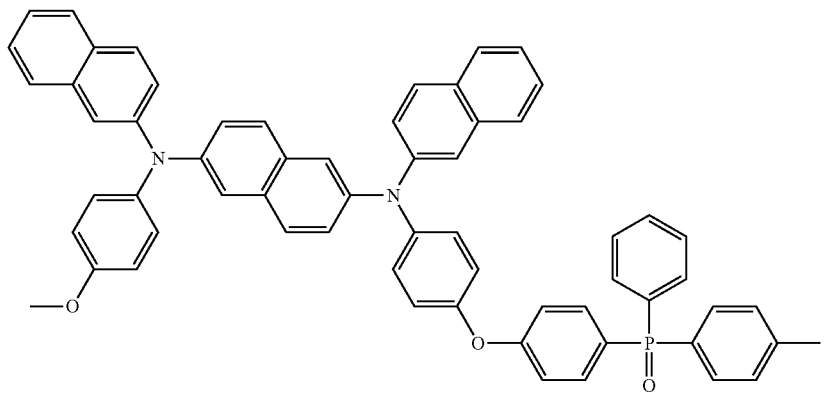

(P-25)

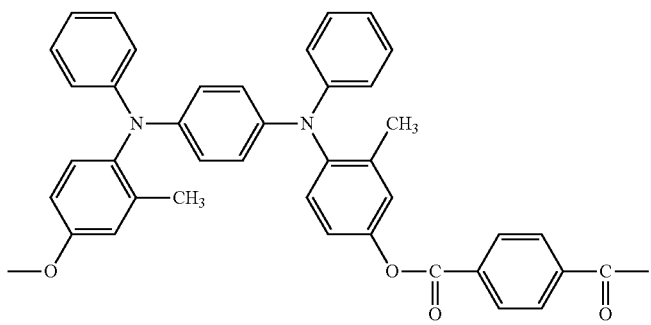

(P-26)

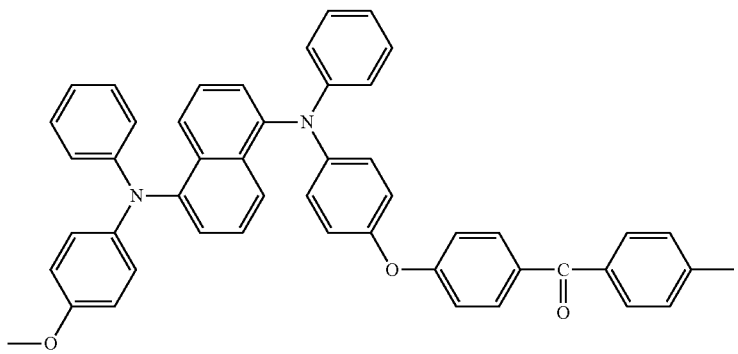

Of the above examples, more preferable from the standpoint of heat stability and charge transport capacity are repetitive units of P-1 to P-11, P-13 to P-18, P-20, P-21, P-23, P-25 and P-26. Still more preferable are repetitive units of P-1, P-3, P-4, P-6, P-9 and P-10.

As another preferable example of macromolecular aromatic tertiary amine compound can be cited a macromolecular compound containing a repetitive unit represented by the following formulae (13) and/or (14).

[Chemical Formula 18]

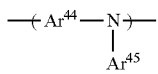

(13)

[Chemical Formula 19]

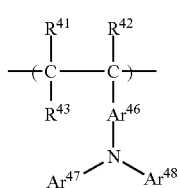

(14)

(In the formula (13) and (14), $Ar^{45}$, $Ar^{47}$ and $Ar^{48}$ represent, independently of each other, an aromatic hydrocarbon group that may have substituents or an aromatic heterocyclic group that may have substituents. $Ar^{44}$ and $Ar^{46}$ represent, independently of each other, a bivalent aromatic hydrocarbon group that may have substituents or a bivalent aromatic heterocyclic group that may have substituents. $R^{41}$-$R^{43}$ represent, independently of each other, a hydrogen atom or an arbitrary group.)

Concrete examples, preferable examples, examples of substituents which can be introduced and examples of preferable substituents of $Ar^{45}$, $Ar^{47}$, $Ar^{48}$ and $Ar^{44}$, $Ar^{46}$ are the same as those described for $Ar^{21}$, $Ar^{22}$ and $Ar^{23}$-$Ar^{25}$, respectively. Preferable as $R^{41}$-$R^{43}$ are a hydrogen atom or substituents described in [substituent group W]. More preferable are a hydrogen atom, alkyl group, alkoxy group, amino group, aromatic hydrocarbon group and aromatic hydrocarbon group.

Preferable examples of a repetitive unit, which is represented by the formulae (13) and (14) and can be applied in the present invention, will be explained below. These examples are presented as representative ones and are not intended to be restrictive.

[Chemical Formula 20]

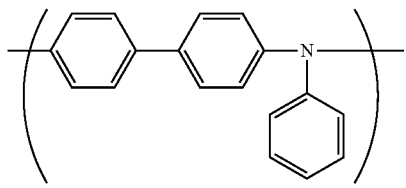

(P-31)

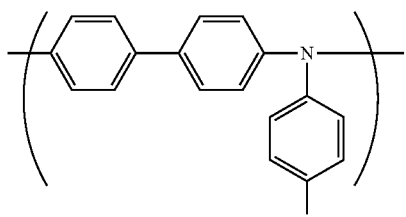

(P-32)

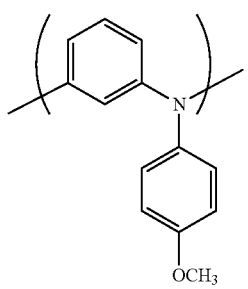

(P-33)

[Chemical Formula 21]

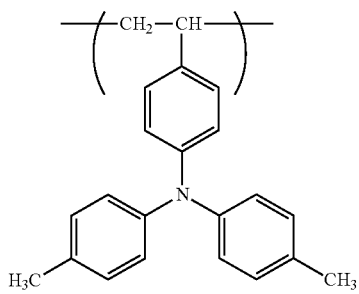

(P-34)

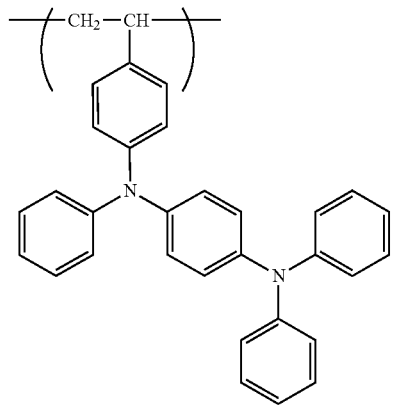

(P-35)

When a composition for a charge-transport film (A) of the present invention is used for film formation by the wet coating method, a hole-transporting compound which is easily soluble in various solvents is preferable. As aromatic tertiary amine compound, binaphthyl compounds represented by the following general formula (15), for example, are preferable. It is also possible to select, from among compounds previously used as hole-injection/transporting film formation material of an organic electroluminescence device, compounds which are easily soluble in various solvents, when appropriate.

[[Chemical Formula 22]]

(15)

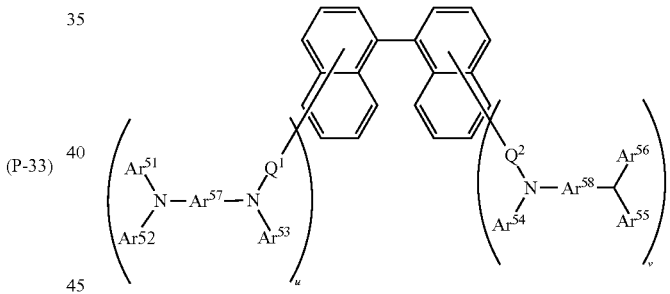

$Ar^{51}$-$Ar^{58}$ in the general formula (15) represent, independently of each other, an aromatic hydrocarbon group that may have substituents or an aromatic heterocyclic group that may have substituents. $Ar^{51}$ and $Ar^{52}$, as well as $Ar^{55}$ and $Ar^{56}$, may combine together to form a ring. Concrete examples, preferable examples, examples of substituents which can be introduced and examples of preferable substituents of $Ar^{51}$-$Ar^{58}$ are the same as those described for $Ar^{21}$-$Ar^{25}$.

Also, u and v each represent an integer which is 0 or larger, and 4 or smaller. They should satisfy the relation $u+v \geq 1$. Particularly preferable combination is u=1 and v=1.

$Q^1$ and $Q^2$ represent, independently of each other, directly connecting or bivalent connecting moiety.

The naphthalene ring in the general formula (15) may have arbitrary substituents in addition to substituents -($Q^1NAr^{53}Ar^{57}(NAr^{51}Ar^{52})$) and -($Q^2NAr^{54}Ar^{58}$ ($NAr^{55}Ar^{56}$)). Further, the substituents -($Q^1NAr^{53}Ar^{57}$ ($NAr^{51}Ar^{52}$)) and -($Q^2NAr^{54}Ar^{58}(NAr^{55}Ar^{56})$) may be at any position of the naphthalene ring. In particular, binaphthyl compounds having the substituents at positions C-4 and C-4' are more preferable.

It is preferable that the binaphthylene structure of a compound represented by the general formula (15) has substituents at C-2 and C-2'. As substituent at C-2 and C-2' can be cited an alkyl group that may have substituents, alkoxy group that may have substituents, alkenyl group that may have substituents and alkoxycarbonyl group that may have substituents.

The binaphthylene structure of a compound represented by the general formula (15) may have arbitrary substituents at positions other than C-2 and C-2'. As substituent can be cited the same substituents described above for C-2 and C-2'. It is considered likely that the two naphthalene rings in a compound represented by the general formula (15) assume a distorted configuration due to the substituents at positions C-2 and C-2', which will lead to increased solubility of the compound.

The molecular weight of the binaphthyl compounds, represented by the general formula (15), is usually 2000 or lower, preferably 1200 or lower, and usually 500 or higher, preferably 700 or higher.

Preferable examples of a binaphthyl compound, which is represented by the general formula (15) and can be applied in the present invention, will be explained below. The present invention is, though, not limited to these.

[Chemical Formula 23]

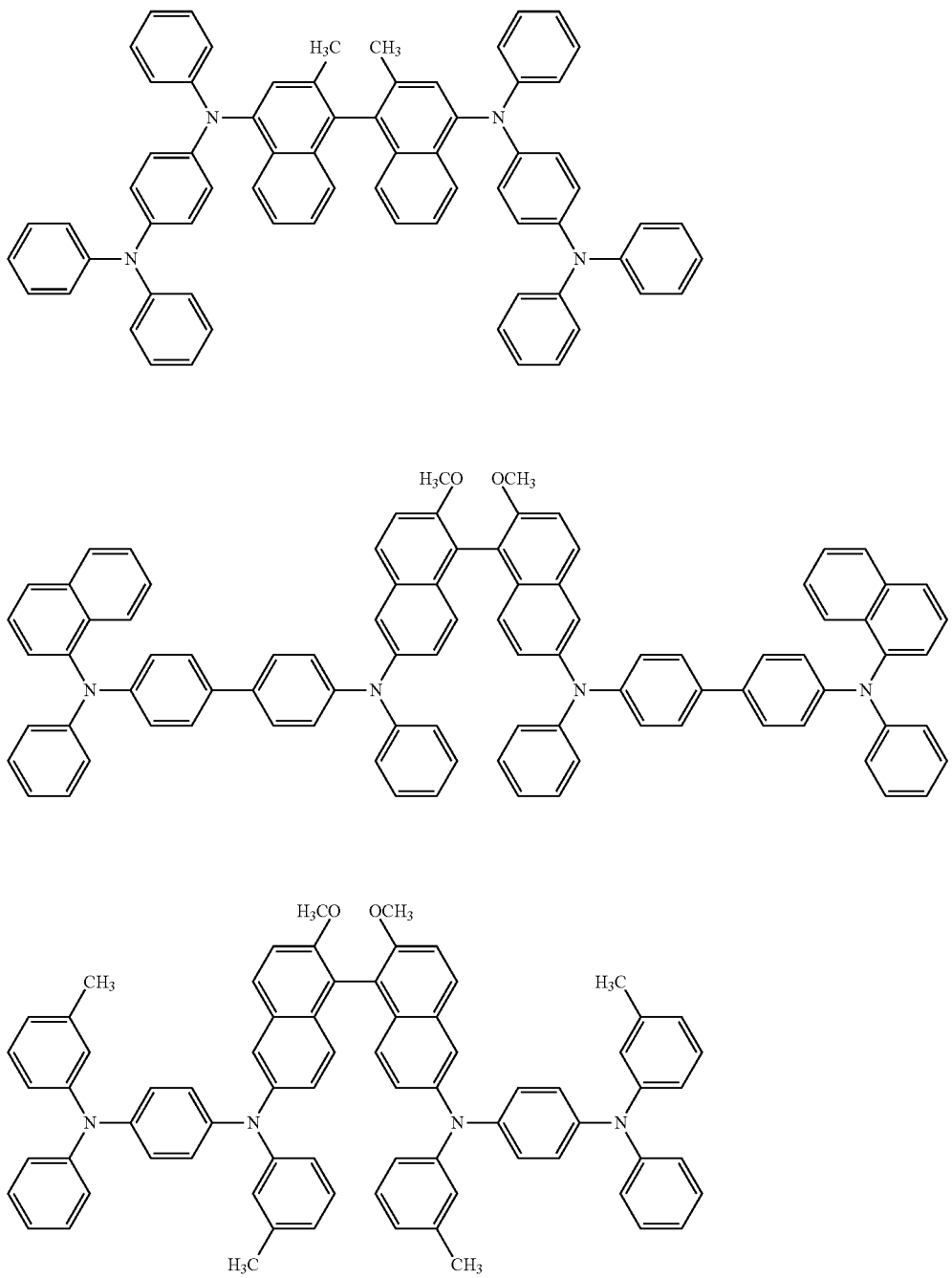

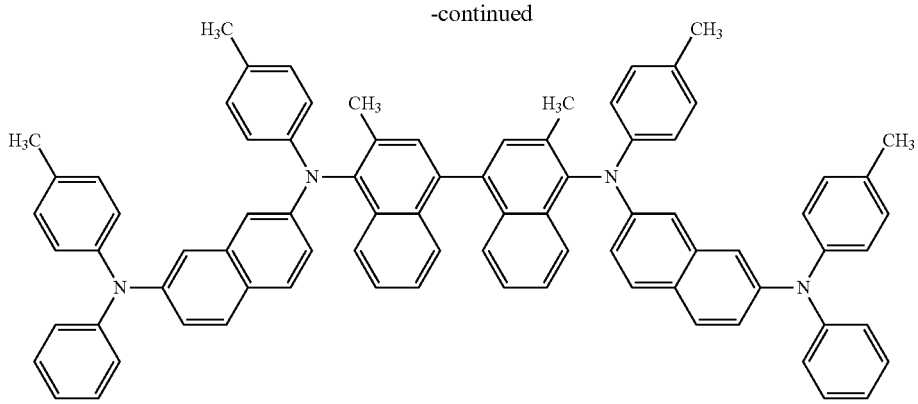

As other aromatic amine compounds applicable as hole-transporting compound of the present invention can be cited previously known compounds which have been used as hole-injection/transporting layer formation material of an organic electroluminescence device. Examples include: aromatic diamine compounds in which tertiary aromatic amine unit such as 1,1-bis(4-di-p-tolylaminophenyl)cyclohexane is linked (Japanese Patent Laid-Open Application No. SHO 59-194393); aromatic amines in which two or more tertiary amines, represented by 4,4'-bis[N-(1-naphthyl)-N-phenylamino]biphenyl, are contained and in which nitrogen has two or more condensed aromatic ring substituents (Japanese Patent Laid-Open Application No. HEI 5-234681); aromatic triamines of triphenylbenzene derivatives possessing a star-burst structure (U.S. Pat. No. 4,923,774); aromatic diamines such as N,N'-diphenyl-N,N'-bis(3-methylphenyl)biphenyl-4, 4-f-diamine (U.S. Pat. No. 4,764,625); α,α,α',α'-tetramethyl-α,α'-bis(4-di-p-tolylaminophenyl)-p-xylene (Japanese Patent Laid-Open Application No. HEI 3-269084); triphenyl amine derivatives each of which is sterically asymmetric as a whole molecule (Japanese Patent Laid-Open Application No. HEI 4-129271); compounds in which a pyrenyl group has more than one aromatic diamino groups (Japanese Patent Laid-Open Application No. HEI 4-175395); aromatic diamines in which tertiary aromatic amine units are linked by an ethylene group (Japanese Patent Laid-Open Application No. HEI 4-264189); aromatic diamines possessing styryl structure (Japanese Patent Laid-Open Application No. HEI 4-290851); compounds in which aromatic tertiary amine units are linked by thiophene group (Japanese Patent Laid-Open Application No. HEI 4-304466); aromatic triamines of star-burst structure (Japanese Patent Laid-Open Application No. HEI 4-308688); benzylphenyl compounds (Japanese Patent Laid-Open Application No. HEI 4-364153); compounds in which tertiary amines are linked by fluorene group (Japanese Patent Laid-Open Application No. HEI 5-25473); triamine compounds (Japanese Patent Laid-Open Application No. HEI 5-239455); bis-dipyridylamino-biphenyl (Japanese Patent Laid-Open Application No. HEI 5-320634); N,N, N-triphenyl amine derivatives (Japanese Patent Laid-Open Application No. HEI 6-1972); aromatic diamines possessing phenoxazine structure (Japanese Patent Laid-Open Application No. HEI 7-138562); diaminophenyl phenanthridine derivatives (Japanese Patent Laid-Open Application No. HEI 7-252474); hydrazone compounds (Japanese Patent Laid-Open Application No. HEI 2-311591); silazane compounds (U.S. Pat. No. 4,950,950); silanamine derivatives (Japanese Patent Laid-Open Application No. HEI 6-49079); phosphamine derivatives (Japanese Patent Laid-Open Application No. HEI 6-25659); and quinacridone compounds. These aromatic amine compounds may be used as a mixture of more than one compound, if necessary.

As another example of aromatic amine compounds applicable as hole-transporting compound of the present invention can be cited a metal complex of 8-hydroxyquinoline derivative containing diarylamino group. The above metal complex contains a central metal selected from the group consisting of alkali metals, alkali earth metals, Sc, Y, V, Cr, Mn, Fe, Co, Ni, Cu, Zn, Cd, Al, Ga, In, Si, Ge, Sn, Sm, Eu and Tb. The ligand 8-hydroxyquinoline carries one or more diarylamino group as substituent and may carry another arbitrary substituent other than diarylamino group.

Preferable examples of phthalocyanine derivatives or porphyrine derivatives applicable as hole-transporting compound of the present invention include: porphyrine, 5,10,15, 20-tetraphenyl-21H,23H-porphyrine, 5,10,15,20-tetraphenyl-21H,23H-porphyrine cobalt(II), 5,10,15,20-tetraphenyl-21H,23H-porphyrine copper(II), 5,10,15,20-tetraphenyl-21H,23H-porphyrine zinc(II), 5,10,15,20-tetraphenyl-21H,23H-porphyrine vanadium (IV) oxide, 5,10, 15,20-tetra(4-pyridyl)-21H,23H-porphyrine, 29H,31H-phthalocyanine copper (II), phthalocyanine zinc (II), phthalocyanine titanium, phthalocyanine oxide magnesium, phthalocyanine lead, phthalocyanine copper (II), and 4,4',4", 4'''-tetraaza-29H,31H-phthalocyanine.

Preferable examples of oligothiophen derivatives applicable as hole-transporting compound of the present invention include α-sexithiophen.

The molecular weight of these hole-transporting compounds, except macromolecular compounds containing specific repetitive units described above, is usually 5000 or lower, preferably 3000 or lower, more preferably 2000 or lower, still more preferably 1700 or lower, most preferably 1400 or lower, and usually 200 or higher, preferably 400 or higher, more preferably 600 or higher. When the molecular weight of the hole-transporting compound is too high, its synthesis and purification are difficult, which is not desirable. On the other hand, when the molecular weight is too low, it tends to be less heat-resistant, which is not desirable either.

A composition for a charge-transport film (A) of the present invention may contain any one kind of hole-transporting compound described above or may contain two or more kinds of hole-transporting compound. In the case where it contains two or more kinds of hole-transporting compound, its combination is arbitrary. However, it is preferable that one or more kinds of macromolecular aromatic tertiary amine compounds and one or more kinds of other hole-transporting compounds are used in combination. As hole-transporting compound which is used in combination with macromolecular compounds described above, aromatic amine compounds are preferable.

The content of the hole-transporting compound in a composition for a charge-transport film (A) of the present invention should be in the range of ratio specified previously for ionic compounds. In the case where two or more kinds of a composition for a charge-transport film are used in combination, the total content should be within the above range.

[II-3. Ionic Compound (Ion Radical Compound)]

A composition for a charge-transport film (B) of the present invention may contain any one kind of ionic compound (ion radical compound) described previously, or may contain two or more kinds of ionic compound (ion radical compound). It is preferable that it contains one kind of ionic compound (ion radical compound) singly.

It is preferable that a composition for a charge-transport film (B) of the present invention contains a hole-transporting compound, described in [I-2. hole-transporting compound], in addition to ionic compound (ion radical compound). The content of the hole-transporting compound in a composition for a charge-transport film (B) of the present invention is preferably 10 weight % or higher, more preferably 100 weight % or higher, and preferably 10000 weight % or lower, relative to the ionic compound (ion radical compound).

A charge-transport film, formed from a composition for a charge-transport film (B) of the present invention through positive charge transfer from an ionic compound (ion radical compound) to a nearby neutral hole-transporting compound, exhibits high hole-injection/transporting capability. Therefore, it is preferable that both of the ionic compound (ion radical compound) and the neutral hole-transporting compound are present and their ratio is in the range of approx. 1:100-100:1. It is more preferable that both compounds are present at a ratio of approx. 1:20-20:1.

As will be described later in [II-5. Others], in a composition for a charge-transport film (A) of the present invention, which contains an electron-accepting ionic compound, represented by the general formulae (1)-(3) and a hole-transporting compound, there occurs electron transfer from a hole-transporting compound to an electron-accepting ionic compound and there is formed an ionic compound consisting of a cation radical of a hole-transporting compound and a counter anion.

[II-4. Solvents and Others]

In addition to the above electron-accepting ionic compound and hole-transporting compound, a composition for a charge-transport film (A) of the present invention may contain other components when needed, for example, solvents or various kinds of additives. Particularly when a charge-transport film is formed by the wet coating method, using the composition for a charge-transport film of the present invention, it is preferable to maintain the above-described electron-accepting ionic compound and hole-transporting compound in a solubilized state using solvents.

An ion radical compound of the present invention is produced by mixing an electron-accepting ionic compound, which has an anion described previously in [I-1. Counter Anion] as a counter anion, with a hole-transporting compound described previously in [II-2. Hole-Transporting Compound]. In other words, the ion radical compound is a compound derived from an electron-accepting ionic compound and a hole-transporting compound. Therefore, a composition for a charge-transport film (B) of the present invention, which contains an ion radical compound, may contain additional components similarly to a composition for a charge-transport film (A), and when a charge-transport film is formed by the wet coating method, it is preferable to maintain an ion radical compound of the present invention in a solubilized state using solvents.

Regarding the solvent contained in a composition for a charge-transport film (A) of the present invention, there is no special limitation on its kind insofar as the solvent can dissolve both the electron-accepting ionic compound described previously and the hole-transporting compound described previously. Regarding the solvent contained in a composition for a charge-transport film (B) of the present invention, there is no special limitation on its kind insofar as the solvent can dissolve an ion radical compound of the present invention. In this context, the solvent which can dissolve an electron-accepting ionic compound and hole-transporting compound, as described previously, means a solvent which can dissolve the hole-transporting compound to an extent of usually 0.005 weight % or higher, preferably 0.5 weight % or higher, more preferably 1 weight % & or more, and a solvent which can dissolve the ionic compound to an extent of usually 0.001 weight % or higher, preferably 0.1 weight % or higher, more preferably 0.2 weight % or higher. Ionic compounds of the present invention described previously have high solubility and, therefore, various solvents are applicable. The solvent which can dissolve an ion radical compound of the present invention means a solvent which can dissolve the ion radical compound of the present invention to an extent of usually 0.001 weight % or higher, preferably 0.1 weight % or higher, more preferably 0.2 weight % or higher.

As solvent contained in a composition for a charge-transport film (A) of the present invention, it is preferable to use those solvents which do not contain compounds which are likely to inactivate electron-accepting ionic compounds, hole-transporting compounds and free carriers arising from their mixing (cation radical), or those solvents which do not contain compounds likely to produce inactivating compounds. Similarly, as solvent contained in a composition for a charge-transport film (B) of the present invention, it is preferable to use those solvents which do not contain compounds which are likely to inactivate ion radical compounds of the present invention or those solvents which do not contain compounds likely to produce inactivating compounds.

Electron-accepting ionic compounds and hole-transporting compounds of the present invention, free carriers resulting from mixing the two (cation radical) and ion radical compounds of the present invention are stable compounds thermodynamically and electrochemically. Therefore, various solvents can be used. As preferable solvent can be cited, for example, ether type solvents and ester type solvents. Examples of ether type solvents include: aliphatic ethers such as ethylene glycol dimethylether, ethylene glycol diethylether, propylene glycol-1-monomethylether acetate (PG-MEA); and aromatic ethers such as 1,2-dimethoxybenzene, 1,3-dimethoxybenzene, anisole, phenethol, 2-methoxytoluene, 3-methoxytoluene, 4-methoxytoluene, 2,3-dimethylanisole, 2,4-dimethylanisole. Ester type solvent includes, for example, aliphatic esters such as ethyl acetate, n-butyl acetate, ethyl lactate, n-butyl lactate; and aromatic esters such as phenyl acetate, phenyl propionate, methyl benzoate, ethyl benzoate, propyl benzoate, and n-butyl benzoate. These can be used either singly or as an arbitrary combination of two or more kinds in arbitrary ratio.

As applicable solvent in addition to the above ether type solvent and ester type solvent can be cited, for example, aromatic hydrocarbon solvent such as benzene, toluene and xylene, amide type solvent such as N,N-dimethylformamide and N,N-dimethylacetamide, and dimethylsulfoxide. These can be used either singly or as an arbitrary combination of two or more kinds in arbitrary ratio. It is also possible that one or more kinds of these solvents are used in combination with one or more kinds of the above ether type solvent and ester type solvent. As aromatic hydrocarbon solvent such as benzene, toluene and xylene are poor in their capability to dissolve electron-accepting compounds and free carriers (cation radical), it is preferable to combine them with ether type solvent and ester type solvent.

It is to be noted that halogen-containing solvents are not desirable because of their heavy burden on the environment. As solvent containing compounds which are likely to inactivate previously mentioned ionic compounds, hole-transporting compounds, free carriers (cation radical), and ion radical compounds of the present invention, or as solvent containing compounds likely to produce inactivating compounds, can be cited aldehyde type solvent such as benzaldehyde, and ketone type solvent possessing a hydrogen atom at position a such as methylethylketone, cyclohexanone and acetophenone. These aldehyde type solvents and ketone type solvents are not preferable because of possible condensation reaction among solvent molecules or production of impurities due to their reaction with free carriers (cation radical).

In the case where solvents are used, the concentration of the solvent, relative to a composition for a charge-transport film (A), (B) of the present invention, is usually 10 weight % or higher, preferably 30 weight % or higher, more preferably 50 weight % or higher, and usually 99.999 weight % or lower, preferably 99.99 weight % or lower, more preferably 99.9 weight % or lower. In the case where two or more kinds of solvents are mixed and used, the total content of the solvents should fall within the above range.

An organic electroluminescence device is constructed by stacking layers containing many organic compounds. When a composition for a charge-transport film (A) or (B) is used for constructing an organic electroluminescence device, each layer is thus required to be homogeneous. When layers are formed by the wet coating method, and water is present in a solution for thin film formation (composition for a charge-transport film), water contaminates the film formed, which impairs the homogeneity of the film. Therefore, it is preferable to keep the water content of the solution to the lowest possible level. Furthermore, an organic electroluminescence device, in general, depends on materials which deteriorate badly in the presence of water, such as cathode. Consequently, the presence of water is not desirable from the standpoint of preventing the deterioration of the device.

Concretely, it is preferable that water content of a composition for a charge-transport film (A), (B) of the present invention is held to a level of usually 1 weight % or lower, preferably 0.1 weight % or lower, more preferably 0.05 weight % or less.

The methods to reduce the water content of the composition include, for example: sealing with nitrogen gas, the use of a desiccant, prior dehydration of solvents, and the use of a solvent in which solubility of water is low. In particular, it is preferable to use a solvent in which solubility of water is low, from the standpoint of preventing the phenomenon of whitening due to absorption of moisture in the air by a film of coated solution during the coating process.

It is preferable that a composition for a charge-transport film (A), (B) of the present invention, when used for film formation by the wet coating method, contains solvents in which solubility of water is low. More specifically, it is preferable to use solvents in which solubility of water at 25° C. is 1 weight % or lower, preferably 0.1 weight % or lower. The content of the solvent in the whole composition is usually 10 weight % or higher, preferably 30 weight % or higher, more preferably 50 weight % or higher.

Other components which a composition for a charge-transport film (A), (B) of the present invention may contain include binder resin, coating ameliorator and the like. The kinds and contents of these components can be selected depending on the applications of the composition for a charge-transport film.

[II-5. Others]

The charge-transport film formed from a composition for a charge-transport film (A) of the present invention has excellent heat stability and high hole-injection/transporting capability. The reason for these excellent properties will be explained below.

A composition for a charge-transport film (A) of the present invention contains an electron-accepting ionic compound represented by the general formulae (1)-(3) and a hole-transporting compound. The cation of the electron-accepting ionic compound of the general formulae (1)-(3) has a hypervalent central atom, and its positive charge is widely delocalized. Therefore, it has a high electron-accepting capacity. This causes electron transfer from the hole-transporting compound to the cation of the electron-accepting ionic compound, leading to the formation of an ion radical compound consisting of a cation radical of the hole-transporting compound and a counter anion. This cation radical of the hole-transporting compound works as a carrier of electrical charge and enhances the electroconductivity of the charge-transport film.

For example, when electron transfer occurs from a hole-transporting compound represented by formula (16) below to an electron-accepting ionic compound represented by formula (1') below, an ion radical compound consisting of a hole transporting cation radical and a counter anion, represented by formula (17), is formed.

[Chemical Formula 24]

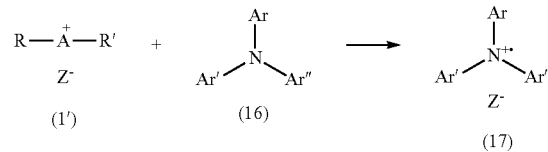

An electron-accepting ionic compound of the general formulae (1)-(3), described previously, is characterized in that it produces effectively an ion radical compound consisting of a cation radical of a hole-transporting compound and a counter anion, without being sublimed or decomposed easily. Through these characteristics, an electron-accepting ionic compound of the general formulae (1)-(3) and an ionic compound consisting of a cation radical of a hole-transporting compound and a counter anion exhibit excellent heat stability and electrochemical durability. Consequently, heat stability and electrochemical durability of the composition for a charge-transport film is improved.

Furthermore, a composition for a charge-transport film (B) of the present invention contains an ion radical compound which has excellent heat stability and electrochemical durability. As a result, the composition for a charge-transport film (B) has excellent heat stability and electrochemical durability.

Thus, a charge-transport film formed from a composition for a charge-transport film (A), (B) of the present invention, and a charge-transport film containing an ionic compound of the present invention have excellent heat stability and high hole-injection/transporting capability. Therefore, they can be advantageously used in various areas such as organic electroluminescence device, electrophotographic photoreceptor, photoelectric conversion device, organic solar battery or organic rectifying device. In particular, it is preferable to use them as material for an organic electroluminescence device. It is highly preferable to use them to form a charge-transport layer of an electroluminescence device. Furthermore, through the formation of an intermediate layer present between a anode and an emitting layer, especially a hole-injection layer, of an organic electroluminescence device, electrical communication between a anode and a hole-transport layer or an emitting layer is improved, resulting in lowering of driving voltage and increased stability at the time of continuous operation.

When a charge-transport film formed from a composition for a charge-transport film (A), (B) of the present invention, or a charge-transport film containing an ionic compound of the present invention, is for various purposes, it is preferable that it is molded into a film form. There is no special limitation on the method of film formation. As electron-accepting ionic compounds and ion radical compounds have excellent solubility in solvents, they can be conveniently used for film formation by the wet coating method.

Furthermore, when a charge-transport film is formed using a composition for a charge-transport film (A), (B) of the present invention, heating/drying at a high temperature is applicable at the time of film formation. This contributes to the simplification of the manufacturing process and enhancement of the stability of device characteristics. The advantage as a method of reducing the water content of the coated film is marked especially when a hole-injection layer of an organic electroluminescence device is formed by the wet coating method. Application of heating/drying at a high temperature then can reduce the content of water and residual solvent, which can be a cause of marked deterioration of the device. Furthermore, a charge-transport film formed from a composition for a charge-transport film (A), (B) of the present invention has excellent heat stability and, therefore, heat stability of the organic electroluminescence device produced can be greatly improved.

As electron-accepting ionic compounds of the present invention have excellent heat stability and appropriate sublimation propensity as well as high electron-accepting property, they can be used for film formation by the vacuum deposition method besides the above-mentioned wet coating method. Planning of an organic electroluminescence device can be more versatile and flexible.

[III. Organic Electroluminescence Device]

Figure 1B:
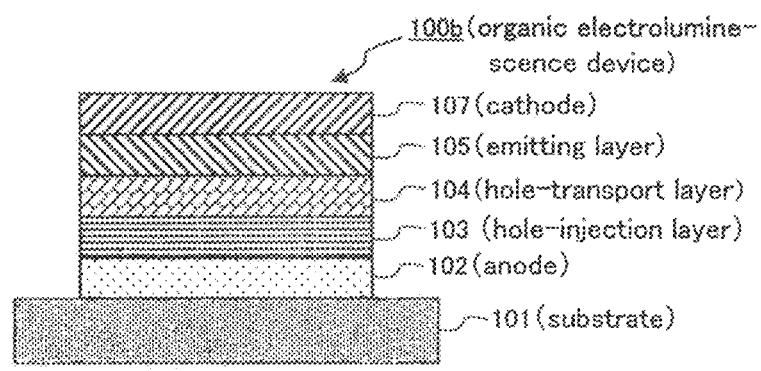
Figure 1C:
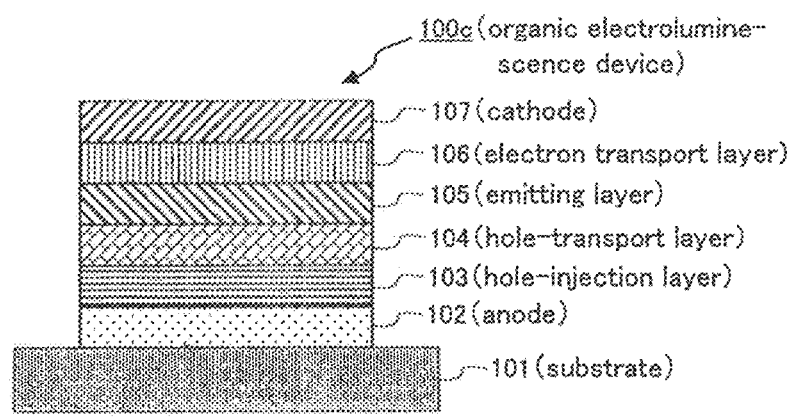

In the following, explanation will be given on the organic electroluminescence device of the present invention referring to FIGS. 1(a)-1(c). FIGS. 1(a)-1(c) are schematic cross-sectional views illustrating examples of the structure of an organic electroluminescence device of one embodiment of the present invention.

The organic electroluminescence device 100a shown in FIG. 1(a) comprises substrate 101, on which are stacked with anode 102, hole-injection layer 103, emitting layer 105 and cathode 107 into layers in this sequence.

Substrate 101 is a support of organic electroluminescence device 100a. As materials used for forming substrate 101 can be cited quartz plate, glass plate, metal plate, metal foil, plastic film, plastic sheet or the like. Of these, preferable are glass plate and transparent plastic sheet such as polyester, polymethacrylate, polycarbonate, polysulphone or the like. In the case where plastics are used for forming substrate 101, it is preferable to install dense-textured film, such as silicon dioxide film or the like, on either one or both sides of substrate 101 for the sake of enhancing gas barrier property.

Anode 102, which is installed atop substrate 101, has a function of hole injecting into hole-injection layer 103. As materials used for forming anode 102 can be cited: metals such as aluminum, gold, silver, nickel, palladium, platinum or the like; electroconductive metal oxide such as oxide of indium and/or tin; halogenated metal such as copper iodide; carbon black; and electroconductive macromolecule such as poly(3-methylthiophene), polypirrole, polyaniline or the like. As production method of anode 102 can be cited usually: sputtering, vacuum deposition or the like on substrate 101; method of applying metal particulate like silver, particulate like copper iodide, carbon black, particulate of electroconductive metal oxide or particulate of electroconductive macromolecule which are dissipated in appropriate binder resin solution on substrate 101; method of forming electroconductive polymer thin film directly on substrate 101 by the electrolytic polymerization; method of applying electroconductive macromolecule solution on substrate 101 or the like. The transmission of visible light of anode 102 is usually 60% or higher, particularly preferably 80% or higher. The thickness of anode 102 is usually 1000 nm or smaller, preferably 500 nm or smaller, and usually 5 nm or larger, preferably 10 nm or larger.

Hole-injection layer 103 is formed on anode 102.

Hole-injection layer 103 is preferably a layer comprising an electron-accepting ionic compound described in above-mentioned [II-1. electron-accepting ionic compound] and a hole-transporting compound described in above-mentioned [II-2. hole-transporting compound]. In this case, the content of the electron-accepting ionic compound in hole-injection layer 103 is in the range of usually 0.1 weight % or higher, preferably 1 weight % or higher, and usually 50 weight % or lower, preferably 25 weight % or lower. When the content of electron-accepting ionic compound is too high, charge transport capacity tends to decrease. On the other hand, when the content is too low, the production of a free carrier (cation radical) is insufficient, which is not desirable either. It should be noted that the content range of electron-accepting ionic compound, specified here, is the same as in the case of a layer, containing electron-accepting ionic compound, which is provided as not a hole-injection layer in the device.

Hole-injection layer 103 is formed on the above-mentioned anode 102, by the wet coating method or vacuum deposition method when the electron-accepting ionic compound and hole-transporting compound are low molecular compounds, and formed by the wet coating method when those compounds are macromolecule compounds.

Otherwise, hole-injection layer 103 is preferably a layer comprising an ion radical compound described in above-mentioned [I. Ionic Compound (Ion Radical Compound)]. In this case, the content of the ion radical compound, of the present invention, in hole-injection layer 103, is in the range of usually 0.1 weight % or higher, preferably 1 weight % or higher, and usually 99 weight % or lower, preferably 95 weight % or lower. As hole-injection layer 103 exhibits high hole-injection/transporting capability through positive charge transfer from the ion radical compound to a nearby electrically neutral compound, it is not preferable if the content of the ion radical compound is too high as well as if it is too low. It should be noted that the content range of ion radical compound, specified here, is the same as in the case of a layer, containing ion radical compound, which is provided as not a hole-injection layer in the device.

Hole-injection layer 103 is formed on the above-mentioned anode 102, either by the wet coating method or vacuum deposition method, when the ion radical compound is a low molecular compound, or by the wet coating method when the compound is a macromolecule compound.

As the ion radical compound and electron-accepting ionic compound of the present invention have, as mentioned earlier, excellent heat-resistant property, high electron-accepting property, appropriate sublimation propensity and excellent solubility in solvents, they can be used for film formation by both the vacuum deposition method and wet coating method.

When a layer is formed by the vacuum deposition method, an electron-accepting ionic compound and a hole-transporting compound are put in separate crucibles placed in a vacuum instrument and evacuation is performed with an appropriate vacuum pump until vacuum reaches approx. $10^{-4}$ Pa. Then, the electron-accepting ionic compound and hole-transporting compound are evaporated, independently controlling their evaporation amounts, through heating of each crucible. Consequently, hole-injection layer 103 is formed on anode 102 of the substrate placed facing the crucibles.

Otherwise, an ion radical compound is put in a crucible placed in a vacuum instrument and evacuation was performed with an appropriate vacuum pump until vacuum reaches approx. $10^{-4}$ Pa. Then, the ion radical compound is evaporated, controlling its evaporation amount, through heating of the crucible, Consequently, hole-injection layer 103 is formed on anode 102 of the substrate placed facing the crucible. It is preferable that a hole-transporting compound is put in a different crucible from the one for the ion radical compound and evaporated, controlling the evaporation amount, followed by the formation of hole-injection layer 103 consisting of the ion radical compound and the hole-transporting compound on anode 102.

When a layer is formed by the wet coating method, coating solution, namely composition for a charge-transport film (A) is prepared using the predetermined amount of electron-accepting ionic compound and hole-transporting compound, by adding, if necessary, binder resin or coating ameliorator which do not function as traps for electric charge. Then, the solution is coated on anode 102 by the wet coating method such as spin coating, dip coating or the like, followed by drying, to form hole-injection layer 103.

Otherwise, coating solution, namely composition for a charge-transport film (B) is prepared using the predetermined amount of ion radical compound, by adding, if necessary, hole-transporting compound, binder resin or coating ameliorator which does not function as traps for electric charge. Then, the solution is coated on anode 102 by the wet coating method such as spin coating, dip coating or the like, followed by drying, to form hole-injection layer 103.

When hole-injection layer 103 having free carrier (cation radical) is formed on anode 102, it is preferable that the hole-injection layer 103 is formed by the wet coating method using compositions for a charge-transport film (A) or (B) of the present invention, so as to smooth the roughness on the surface of the anode as described above. The film thickness of hole-injection layer 103, formed in this procedure, is in the range of usually 5 nm or larger, preferably 10 nm or larger, and usually 1000 nm or smaller, preferably 500 nm or smaller.

Emitting layer 105 is installed atop hole-injection layer 103 and is formed from materials which can reunion efficiently electrons injected from cathode 107 and holes transported from hole-injection layer 103 between electrodes which are given with electric field and can emit light efficiently by the reunion. Examples of materials used for forming emitting layer 105 are: low molecule luminescent materials such as metal complex like aluminum complex of 8-hydroxyquinoline, metal complex of 10-hydroxybenzo[h]quinoline, bisstyrylbenzene derivatives, bisstyrylarylene derivatives, metal complex of (2-hydroxyphenyl)benzothiazole, silole derivatives; systems consisting of a luminescent material and an electron transfer material mixed with a macromolecule compound such as poly(p-phenylenevinylene), poly[2-methoxy-5-(2-ethylhexyloxi)-1,4-phenylenevinylene], poly(3-alkylthiophene), polyvinyl carbazole; or the like.

It is possible to enhance the luminescence characteristics of devices, especially the driving stability, by using a metal complex, such as aluminum complex of 8-hydroxyquinoline, as a host material and doping the host material with a compound such as a condensed polycyclic aromatic ring, e.g., naphthacene derivatives such as rubrene, quinacridone derivatives, perylene or the like, in an amount of usually 0.1 weight % or higher and 10 weight % or lower relative to the host material.

These materials are formed into thin film on hole-injection layer 103 by coating them on hole-injection layer 103 through the vacuum deposition method or wet coating method. The film thickness of emitting layer 105, formed in this procedure, is in the range of usually 10 nm or larger, preferably 30 nm or larger, and usually 200 nm or smaller, preferably 100 nm or smaller.

Cathode 107 has a function of injecting electrons to emitting layer 105. As material used for forming cathode 107, metals having low work function are preferable. For example, tin, magnesium, indium, calcium, aluminum, silver or other appropriate metals, or alloys of them may be used. Examples include: electrodes formed from alloys having low work functions such as magnesium-silver alloy, magnesium-indium alloy, and aluminum-lithium alloy. The film thickness of cathode 107 is usually in the range similar to that of anode 102. It is effective, for the purpose of protecting cathode 107 having low work function, a metallic layer having high work function and thus having high stability against atmosphere is stacked over the cathode 107, from the standpoint of increasing the stability of the device. For this purpose, metals like aluminum, silver, copper, nickel, chromium, gold, platinum or the like may be used. Furthermore, inserting extremely thin insulating film (with 0.1-5 nm of film thickness), formed from LiF, $MgF_2$, $Li_2O$ or the like, into the boundary between cathode 107 and emitting layer 105 can enhance the efficiency of the device.

FIG. 1(*b*) illustrates a function-separated-type of luminescence device. In organic electroluminescence device 100*b* shown in FIG. 1(*b*), hole-transport layer 104 is provided between hole-injection layer 103 and emitting layer 105, in order to enhance the luminescence characteristics of the device. The other layers are the same as those in organic electroluminescence device 100*a* shown in FIG. 1(*a*). As material for hole-transport layer 104, it is necessary to select one that can keep the hole injecting efficiency from hole-injection layer 103 to be high and can transport holes injected efficiently. To meet these requirements, the material should have appropriate ionization potential, high hole mobility, excellent chemical stability, and is not liable to generate impurities which function as traps at the time of production and use. In addition, as it is a layer which contacts directly to emitting layer 105, it does preferably not contain materials which quench luminescence.

As materials used for forming hole-transport layer 104 can be cited the same compounds as those exemplified as hole-transporting compounds contained in composition for a charge-transport film and organic electroluminescence device of the present invention. Hole-transport layer 104 is formed by coating these hole-transporting compounds on hole-injection layer 103 through the wet coating method or vacuum deposition method, The film thickness of hole-transport layer 104, formed in this procedure, is in the range of usually 10 nm or larger, preferably 30 nm or larger, and usually 300 nm or smaller, preferably 100 nm or smaller.

FIG. 1(c) illustrates another embodiment of a function-separated-type luminescence device. In organic electroluminescence device 100c shown in FIG. 1(c), electron transport layer 106 is provided between emitting layer 105 and cathode 107. The other layers are the same as those in organic electroluminescence device 100b shown in FIG. 1(b). As compound used for electron transport layer 106, it is necessary to select one through which electron can be injected easily from cathode 107 and having further large electron transportation capability. As such electron transport material can be cited, for example: aluminum complex of 8-hydroxyquinoline, oxadiazole derivatives or system dissipated with them in resins like polymethylmethacrylate (PMMA), phenanthroline derivatives, 2-t-butyl-9,10-N,N'-dicyanoanthraquinonediimine, n-type amorphous hydrogenated silicon carbide, n-type zinc sulfide, n-type zinc selenide, or the like. The film thickness of electron transport layer 106 is in the range of usually 5 nm or larger, preferably 10 nm or larger, and usually 200 nm or smaller, preferably 100 nm or smaller.

Organic electroluminescence devices 100a-100c, shown in FIGS. 1(a)-1(c), are not limited to these examples shown in these figures. For example, the organic electroluminescence device may have reversed structure of FIGS. 1(a)-1(c). In other words, it may be formed in a manner that it has a cathode 107, emitting layer 105, hole-injection layer 103 and anode 102, which are stacked into layers in this sequence on the substrate 101. In addition, any other appropriate layers may be provided between each layer shown in FIGS. 1(a)-1(c), or any two or more layers may be provided integrally, insofar as those modifications are not apart from the scope of the present invention. As another example, the organic electroluminescence device may be installed between two substrates, at least one of which is high in transparency.

The layer containing an ionic compound of the present invention is not necessarily hole-injection layer 103, which is in contact with anode 102, but may be any one or more layers provided between anode 102 and cathode 107. It is preferable, though, that it is one or more layers located between anode 102 and emitting layer 105, i.e., hole-injection layer 103 or hole-transport layer 104. More preferably, it is hole-injection layer 103.

More specified explanation on the production method for organic electroluminescence devices 100a-100c having thin layers formed by the wet coating method using compositions for a charge-transport film of the present invention. To produce organic electroluminescence devices 100a-100c, anode 102 is formed on substrate 101 by the sputtering, vacuum deposition or the like. Atop anode 102 formed, at least one of hole-injection layer 103 and hole-transport layer 104 is then formed by the wet coating method using compositions for a charge-transport film of the present invention. Then, emitting layer 105 is formed on the hole-injection layer 103 and/or hole-transport layer 104 by the vacuum deposition method or wet coating method. Electron transport layer 106 is then formed, if necessary, on the emitting layer 105 formed by the vacuum deposition method or wet coating method. Cathode 107 is then formed on the electron transport layer 106.

When at least one layer of hole-injection layer 103 and hole-transport layer 104 is formed by the wet coating method, coating solution, namely composition for a charge-transport film is prepared usually using the predetermined amount of an ionic compound and a hole-transporting compound, and adding, if necessary, binder resin or coating ameliorator and dissolving them into the solution, which do not function as traps for electric charge. Then, the solution is coated on anode 102 by the wet coating method such as spin coating, dip coating or the like, followed by drying, to form at least one layer of hole-injection layer 103 and hole-transport layer 104.

From the standpoint of the hole mobility, the content of binder resin, relative to each of these layers, is usually preferably 50 weight % or lower, more preferably 30 weight % or lower, and most preferably it is substantially zero.

The structure of thin film, formed from compositions for a charge-transport film (A) or (B) of the present invention, can reach very high level of thermostability by means of heat processing, in addition to and after drying, because heat processing activates migration of molecules contained in the film obtained. This leads to very preferable results of enhanced smoothness of the film surface and decrease in the amount of water, which may cause the deterioration of the device.

More concretely, heat processing at temperature of usually 60° C. or higher, preferably 90° C. or higher, more preferably 120° C. or higher, further more preferably 150° C. or higher, and usually 350° C. or lower is carried out preferably, after film formation by the wet coating method and drying, for the sake of sufficient effect of smoothing surface and dehydration. However, in the case where the composition contains the hole-transporting compound and the hole-transporting compound has high crystalline property, the heat processing is preferably carried out at temperature lower than the glass transition temperature Tg of the hole-transporting compound, preferably by 10 or more degree, to prevent the possibilities of crystallization due to heat, which may cause decrease in smoothness of film surface. On the contrary, in the case where the hole-transporting compound contained in the composition has high amorphous property, the heat processing is preferably carried out at temperature higher than the glass transition temperature Tg of the hole-transporting compound for the sake of enhancing the smoothness of film surface, because the migration of molecules of hole-transporting compound is considered to be activated in such situation.

In the present invention, that hole-transporting compound has "high crystalline property" means that crystallization temperature Tc can be observed in DSC measurement in the temperature range of glass transition temperature Tg or higher and 350° C. or lower, or that glass transition temperature Tg cannot be observed clearly in DSC measurement in the temperature range of 350° C. or lower. On the contrary, that it has "high amorphous property" means that crystallization temperature Tc cannot be observed in DSC measurement in the temperature range of glass transition temperature Tg or higher and 350° C. or lower.

Heat time is in the range of usually 1 minute or longer, preferably 5 minutes or longer, more preferably 10 minutes or longer, and usually 8 hours or shorter, preferably 3 hours or shorter, more preferably 90 minutes or shorter.

Accordingly, because the surface of the layer, formed from composition for a charge-transport film (A), (B) of the present invention by the wet coating method, is smooth, the problem of short circuit, while the production of the device, due to the surface roughness of anode 102 formed from ITO or the like can be resolved.

In addition, the present invention also relates to an electron-accepting compound to be contained in a charge-transport film together with a charge-transporting compound, wherein a resistivity $RR_1$ [Ωcm] of a charge-transport film 1, which is composed of the electron-accepting compound and a charge-transporting compound, and resistivity $RR_0$ [Ωcm] of a charge-transport film 2, which is composed of a charge-transporting compound, meet the following relation $$RR_1/RR_0 < 8 \times 10^{-2}.$$

(On the conditions, a same compound is used as the charge-transporting compounds contained in the charge-transport film 1 and the charge-transport film 2; and the resistivity mentioned above is the value of {field intensity [V/cm]/current density [A/cm$^2$]} where the {field intensity [V/cm]/current density [A/cm$^2$]} is obtained from a field intensity to be applied when a charge-transport film having a film thickness of between 100-200 nm and a current-carrying area of 0.04 cm$^2$ carries an electric current corresponding to a current density of between 4-6 mA/cm$^2$ while being sandwiched between an anode and a cathode.)

Here, the electron-accepting compound may be any compound that can oxidize the charge-transporting compound. Specifically, it may be any compound as long as it meets the above relationship, examples of which compounds are ionic compounds (an electron-accepting ionic compound and an ion radical compound) of the present invention, Lewis acid, and the likes. It is preferably an ionic compound of the present invention.

The resistivity mentioned above is measured by the following method.

First, charge-transport film 1 containing an electron-accepting compound and a charge-transporting compound is prepared by the following method. Charge-transport film is sandwiched between an anode and a cathode for the measurement.

The anode is prepared by subjecting a glass substrate, on which is deposited a transparent electricity conducting film of indium tin oxide (ITO) with a thickness of 120 nm, to usual photolithography technique and hydrogen chloride etching, leading to a stripe pattern formation of 2 mm in width.

This ITO substrate with pattern formation is washed, successively, with a detergent solution using ultrasonic, with extrapure water, with extrapure water using ultrasonic and again with extrapure water, followed by drying with compressed air and, finally, ultraviolet ray-ozone cleaning was conducted.

After that, a composition is prepared which consists of the electron-accepting compound, the charge-transporting compound and a solvent. The composition contains 1.0 weight % of the electron-accepting compound and 5.0 weight % of the charge-transporting compound. Anisole is usually used as the solvent. If anisole does not dissolve either the electron-accepting compound or the charge-transporting compound in an amount of 1 weight % or higher, another appropriate solvent is used that can dissolve them in an amount of 1 weight % or higher.

This composition is spin-coated on the above mentioned ITO substrate, forming a homogeneous thin film of 100-200 nm in thickness.

Spin coating is carried out usually in the air, under the environmental conditions of 23° C. and 40% relative humidity. The spinner is run at a rotation speed of 1500 ppm for a rotation time of 30 seconds.

After being formed, the charge-transport film is dried by heating on a hot plate at 50-100° C. for one minute, then dried by heating in an oven at 80-250° C. for 15 minutes.

After drying, a stripe-shaped shadow mask of 2 mm in width is used as a mask for cathode vapor deposition, contacted with the device at the right angle to the ITO stripe of the anode, and placed in a vacuum vapor deposition instrument, from which air is evacuated until the vacuum reaches $3 \times 10^{-4}$ Pa or lower. A layer of aluminum of 80 nm in thickness is formed at a deposition speed of 0.2-1.0 nm/sec and a vacuum of $5 \times 10^{-4}$ Pa by heating a molybdenum boat to form the cathode. While the above cathode is being formed by vapor deposition, the substrate temperature is maintained at room temperature. Through this procedure, non-luminescent device 1, which consists of the charge-transport film sandwiched between the ITO cathode and ITO anode, with a current-carrying area of 0.04 cm$^2$ (2 mm×2 mm) is obtained.

Charge-transport film 2 containing charge-transporting compound is produced in a similar procedure. In other words, non-luminescent device 2 is produced in a similar procedure to the above mentioned charge-transport film 1, except that a composition containing only the charge-transporting compound and the solvent is used and is spin-coated on the ITO substrate to form a charge-transport film. Here, the charge-transporting compound and the solvent used for producing charge-transport film 2 are the same as the compound and solvent used in the production procedure of the charge-transport film 1, respectively.

The resistivities of the non-luminescent device 1 and the non-luminescent device 2 are decided from the measurements when electric current is passed through each device.

The voltage is measured when electric current corresponding to a current density of 5-6 mA/cm$^2$ is passed through the non-luminescent devices. According to the measurement, too low current density leads to large measurement errors, while too high current density brings about problems such as short circuits in the measurement element. It is therefore very important to carry on the measurements in a current density of 5-6 mA/cm$^2$. The field intensity [V/cm] is decided from the measurement of voltage V and film thickness of charge-transport film. The resistivity is calculated as (field intensity [V/cm]/current density [A/cm$^2$]).

The value of $RR_1/RR_0$ is preferably below $8 \times 10^{-2}$, more preferably below $1 \times 10^{-2}$, particularly preferably below $3 \times 10^{-3}$. Here, it can be known that, when the value of $RR_1/RR_0$ is smaller, the effect of adding the electron-accepting compounds is larger, relative to the charge transport characteristics of the charge-transport film.

An electron-accepting compound which meets the relation of $$RR_1/RR_0 < 8 \times 10^{-2},$$

can yield a charge-transport film having low resistivity. Therefore, the charge-transport film containing the electron-accepting compound and the charge-transporting compound, when it is used as an organic electroluminescence device, realizes a device that can function with low driving voltage. As a result, the electron-accepting compound is preferably used for an organic electroluminescence device.

Also similarly to the former description, as a preferable charge-transporting compound which can be used for a charge-transport film containing the electron-accepting compound and the charge-transporting compound can be cited: compounds exemplified previously as a hole-transporting compound. The film may contain components other than electron-accepting compound or charge-transporting compound if necessary. As this charge-transport film is low in resistivity, it is preferable to use it for an organic electroluminescence device. However, it can be used in various other areas such as electrophotographic photoreceptor, photoelectric conversion device, organic solar battery, organic rectifying device or the like.

It is preferable that the charge-transport film is usually formed by the wet coating method using a composition for a charge-transport film containing the electron-accepting compound and charge-transporting compound. A charge-transporting compound contained in the composition is the same as one described earlier. When the composition is used for the wet coating method, it usually includes a solvent. Examples of the solvent are the same as listed for the composition for a charge-transport film containing the previously mentioned ionic compound. The composition may also contain other ingredients in addition to the electron-accepting compound, the charge-transporting compound, and the solvent.

EXAMPLES

Hereinafter, the present invention will be explained in further detail with reference to examples. It is to be understood that these examples are presented for the purpose of detailed explanation and are by no means restrictive. They can be modified unless they depart from the scope of the present invention. In the examples below, [ᵗBu] indicates a tertiary butyl group.

[Synthesis of Compound 1]

[Chemical Formula 25]

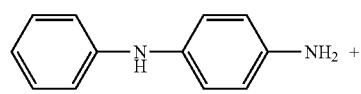

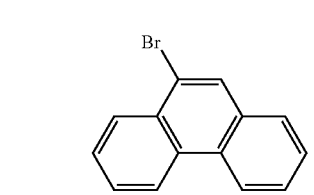

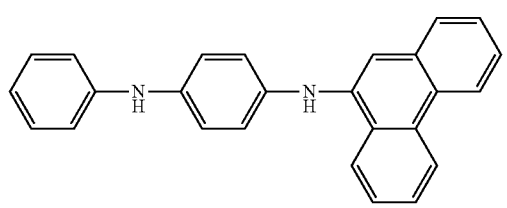

Compound 1

Under a nitrogen atmosphere, a mixture of N-phenyl-1,4-phenylenediamine (23.3 g), 9-bromophenanthrene (25.0 g), t-butoxy sodium (13.1 g), and toluene (190 ml) was heated to 60° C. and combined with a solution of tris(dibenzylidene acetone)dipalladium(0) chloroform complex (0.25 g), and 1,1'-bis(diphenylphosphino)ferrocene (0.40 g) in toluene (10 ml), which solution had been prepared by heating at 60° C. for 10 min while being stirred under a nitrogen atmosphere. The reaction mixture was stirred at 85° C. for 4 hours and then allowed to cool to room temperature. Toluene (200 ml) and activated earth (60 g) was then added to the mixture, which was heated under reflux for 10 minutes with being stirred. After cooled to room temperature, filtered from the activated earth was filtered off from the mixture, which was combined with other activated earth (20 g) and stirred at room temperature for 20 minutes. After the activated earth was removed by filtration, the filtrate was concentrated using an evaporator, and then combined with hexane (150 ml). Crystals that precipitated were filtered and dried under reduced pressure to give compound 1 (31.6 g, yield 90%) as pale yellow powder.

[Synthesis of Compound 2]

[Chemical Formula 26]

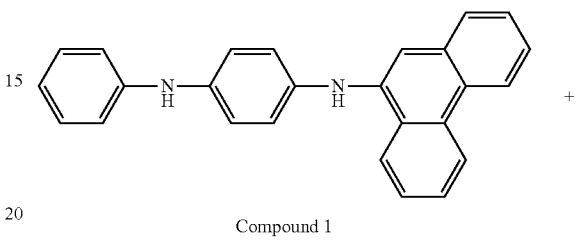

Compound 1

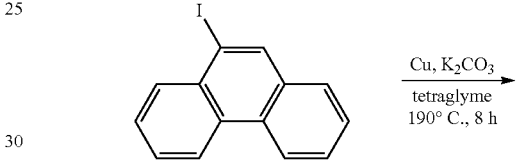

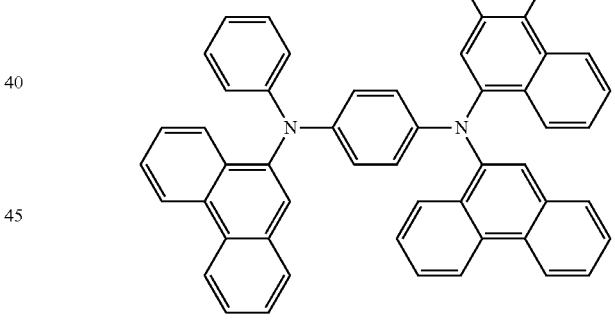

Compound 2

Under a nitrogen atmosphere, object compound (10.2 g), 9-iodophenanthrene (23.2 g), copper powder (5.01 g), potassium carbonate (15.6 g) and tetraglyme (50 ml) were heated at 190° C. for 8 hours while being stirred. After the reaction, the reaction mixture was allowed to cool to room temperature. Ethyl acetate was added to the reaction mixture, from which insoluble matter was filtered off. The ethyl acetate was distilled off from the filtrate in vacuo, and methanol was added to the residue. The precipitate was suspened and washed at 50° C. and recovered by filtration. Further purification was carried out using silica gel column chromatography (n-hexane/toluene-2/1). After being washed with a mixture of methylene chloride and methanol, the eluate was evaporated in vacuo to give compound 2 (12.8 g, yield 65%) as yellow powder.

[Synthesis of Compound 3]

[Chemical Formula 27]

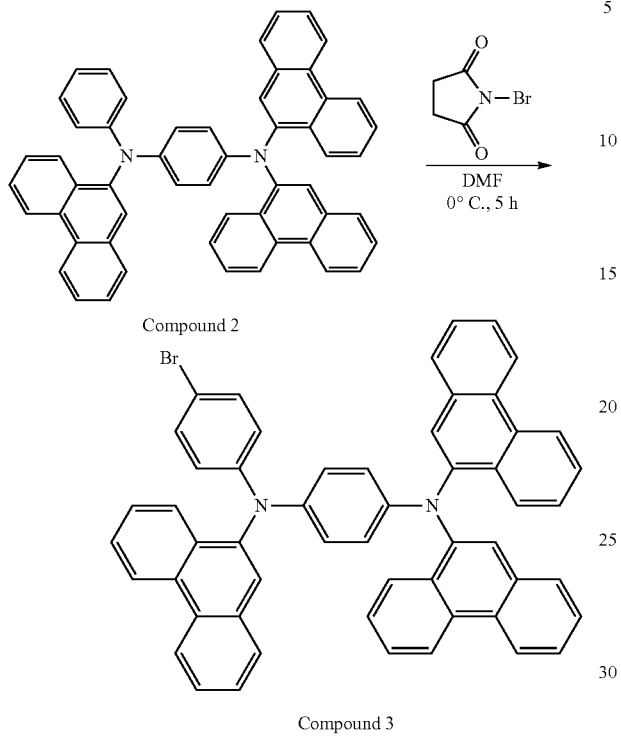

Under a nitrogen atmosphere, into a DMF solution (60 ml) of compound 3 (10.0 g) kept at 0° C., a DMF solution (17 ml) of N-bromosuccinimide (2.50 g) was dropped for one hour, after which the reaction mixture was stirred at 0° C. for four hours. The reaction mixture was combined with water (900 ml) and then extracted with toluene (250 ml). The organic layer was washed with water (100 ml) and concentrated using an evaporator. The concentrate was purified by silica gel column chromatography (n-heptane/toluene=2/1). After being washed with a mixture of methylene chloride and methanol, the eluate was evaporated in vacuo to give compound 3 (10.5 g, yield 95%) as yellow powder.

[Synthesis of Compound 4]

[Chemical Formula 28]

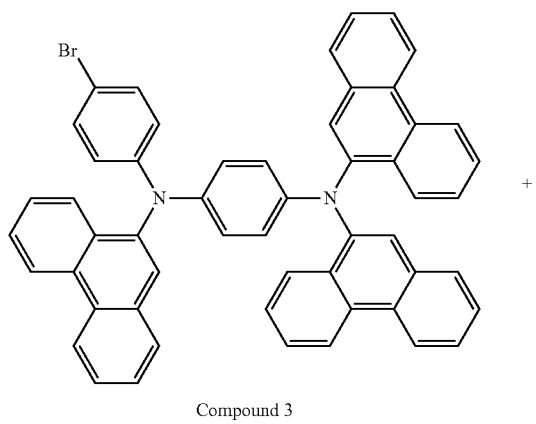

Compound 3

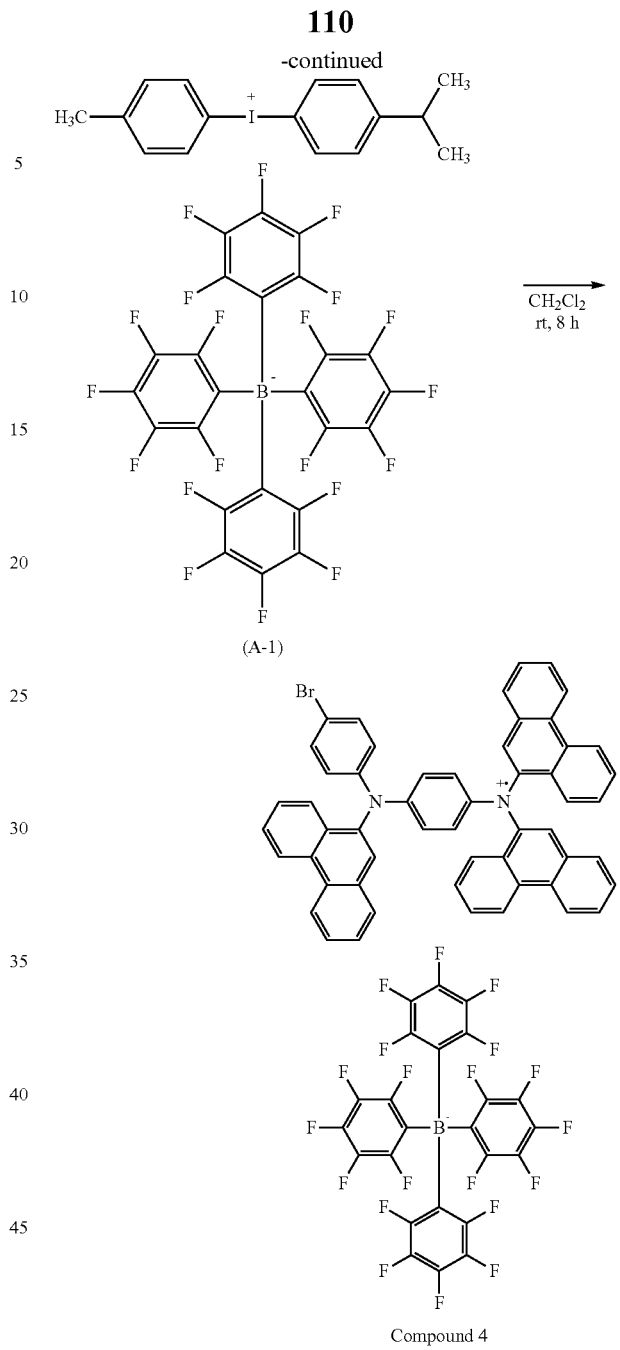

Under a nitrogen atmosphere, compound 3 (0.500 g), compound (A-1) (0.670 g), which was mentioned above as an example (4-isopropyl-4'-methyl diphenyl iodonium tetrakis (pentafluorophenyl) borate), and methylene chloride (50 ml) were stirred at room temperature for 5 hours. The methylene chloride was distilled off in vacuo using an evaporator and the residue was washed with hexane and recovered by filtration. After vacuum drying, compound 4 was obtained as dark green powder (0.846 g, yield 91%).

Figure 2:
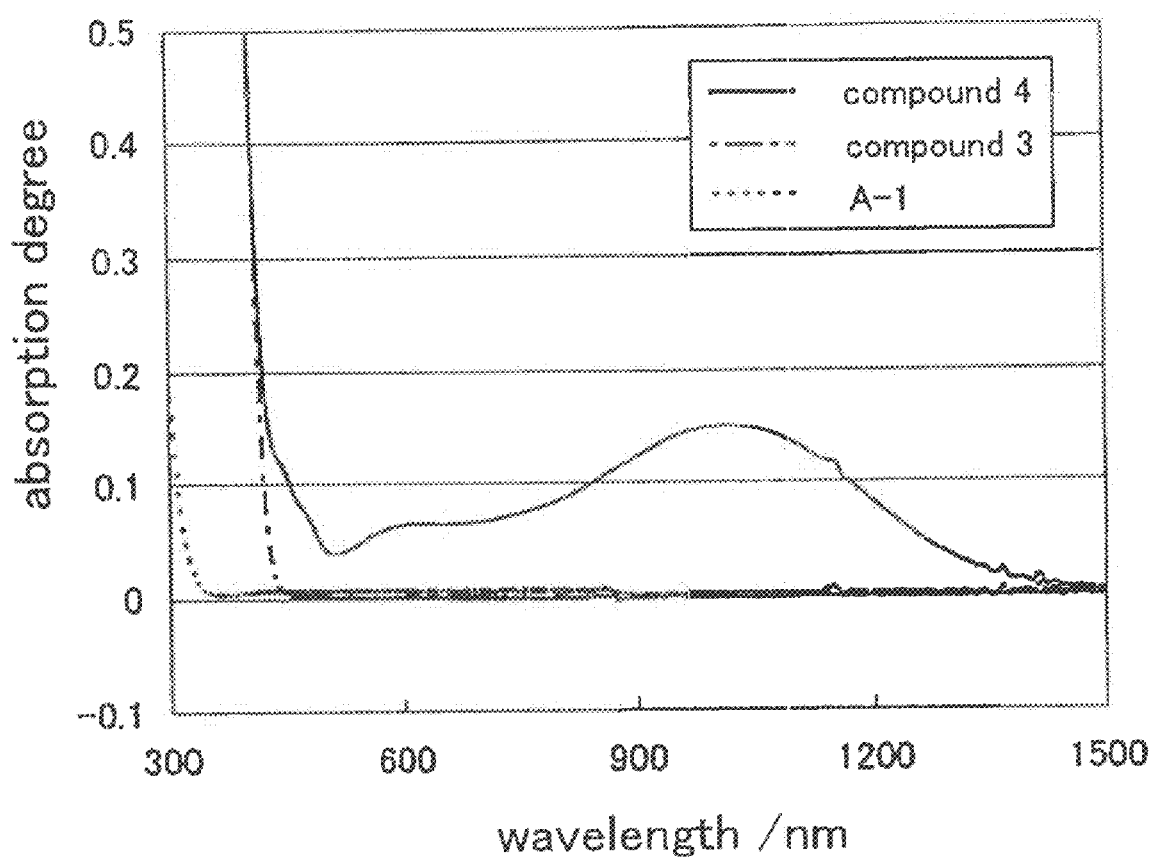
FIG. 2 Absorption spectra of compound 3, illustrated compound (A-1), and compound 4 in $1 \times 10^{-4}$ M methylene chloride solution.

Absorption spectra of compound 3, compound (A-1) and compound 4 in a $1 \times 10^{-4}$ M methylene chloride solution are shown in FIG. 2. As is shown in FIG. 2, a broad absorption band, which is not seen in compound 3 and compound (A-1) and has its absorption maximum at around 700-1200 nm characteristic of aminium cation radical, was observed in compound 4. This indicated that compound 4 has an ionic compound structure, as expected.

In the mass spectral analysis of compound 4 (MALDI-TOF-MS method), an ion of m/z 790 (M+) was observed in the positive ion measurement as expected, and an ion of m/z 679 (M−) was observed in the negative ion measurement as expected.

Example 1

An organic electroluminescence device having a layer composition similar to that of organic electroluminescence device 100b, shown in FIG. 1(b), was prepared by the below-mentioned method.

A glass substrate, on which was deposited a transparent electricity conducting film of indium tin oxide (ITO) at a thickness of 120 nm (spatter film formation, Sanyo Vacuum Co.), was subjected to usual photolithography technique and hydrogen chloride etching, leading to a stripe pattern formation of 2 mm in width, so that an anode was prepared. This ITO substrate with pattern formation was washed, successively, with a detergent solution using ultrasonic, with extrapure water, with extrapure water using ultrasonic and again with extrapure water, followed by drying with compressed air and, finally, ultraviolet ray-ozone cleaning was conducted.

A composite mixture, comprising an ionic compound having a structure (A-1) shown in Table. 1, a charge transporting macromolecule compound (weight-average molecular weight 29600; glass transition temperature 177° C.) having repeated structural units (P-1) described previously and a hole-transporting compound (glass transition temperature 147° C.) shown as the structural formula (H-2) below, was spin-coated on the above glass substrate under the conditions shown in Table 12, forming a homogeneous thin film of 30 nm thickness. Spin coating was carried out in air under the conditions of 23° C. room temperature and 40% relative humidity.

TABLE 12

| Solvent | Ethyl Benzoate | |
|---|---|---|
| Concentration of Coating Solution | Ionic Compound (A-1) | 0.20 Weight % |
| | Charge Transporting Macromolecule Compound (P-1) | 0.33 Weight % |
| | Hole-Transporting Compound (H-2) | 1.67 Weight % |
| Revolution of Spinner | 1500 rpm | |
| Time of Revolution of Spinner | 30 Seconds | |
| Drying Condition | 200° C., 60 Minites in Oven after 80° C., 1 Minites on Hot Plate | |

Next, a substrate onto which a hole-injection layer was formed by application was placed in a vacuum vapor deposition instrument and first evacuation was performed with an oil-sealed rotary pump, followed by final evacuation by an oil diffusion pump with a liquid nitrogen trap until vacuum reached $2 \times 10^{-6}$ Torr (approx. $2.7 \times 10^{-4}$ Pa). Then, vapor deposition was performed by heating an aromatic amine compound 4,4'-bis[N-(9-phenanthryl)-N-phenylamino]biphenyl, shown in the following structural formula (H-1) and placed in a ceramic crucible in the instrument. The vacuum at the time of vapor deposition was $1.3 \times 10^{-6}$ Torr (approx. $1.7 \times 10^{-4}$ Pa) and the deposition rate was 0.2 nm/seconds. By this procedure, a hole-transport layer was formed by layering a film of 45 nm in thickness on the hole-injection layer.

[Chemical Formula 29]

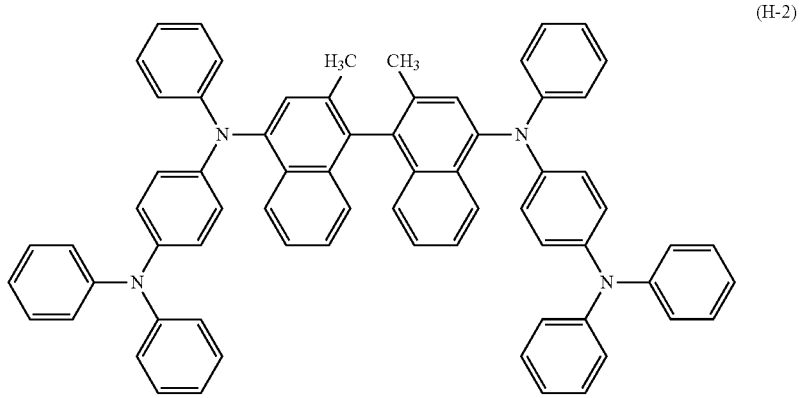

(H-2)

[Chemical Formula 30]

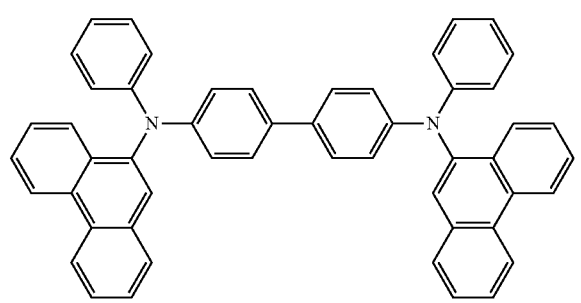

(H-1)

Subsequently, as material of an emitting layer, aluminum complex of 8-hydroxyquinoline, $Al(C_9H_6NO)_3$, with the following structure (E-1) was placed in a crucible and vapor deposition was performed by heating. The vacuum at the time of vapor deposition was $1.3\times10^{-6}$ Torr (approx. $1.7\times10^{-4}$ Pa) and the rate of deposition was 0.2 nm/seconds. A film of 60 nm in thickness was layered over the hole-transport layer to form a hole-transport layer.

[Chemical Formula 31]

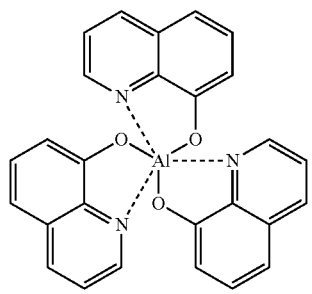

(E-1)

The substrate temperature at the time of vapor deposition of the hole-transport layer and the emitting layer was maintained at room temperature. The device processed up to this vapor deposition stage of the emitting layer was taken out into the air after the vacuum was released. As a mask for cathode vapor deposition, a stripe-shaped shadow mask of 2 mm in width was contacted with the device at right angles to ITO stripe of the anode, placed in another vacuum vapor deposition instrument and air was evacuated until the vacuum reached $2\times10^{-6}$ Torr (approx. $2.7\times10^{-4}$ Pa) or lower. As a cathode, a film of lithium fluoride (LiF) was first formed at a thickness of 0.5 nm on the emitting layer at a deposition speed of 0.01 nm/sec and vacuum of $7.0\times10^{-6}$ Torr (approx. $9.3\times10^{-4}$ Pa) using a molybdenum boat. Subsequently, a film of aluminum was formed thereon at a thickness of 80 nm at a deposition speed of 0.5 nm/sec and vacuum of $1\times10^{-6}$ Torr (approx. $1.3\times10^{-4}$ Pa) by heating aluminum in a molybdenum boat in a similar manner, to form a cathode. While the above two-layer cathode was being prepared by vapor deposition, the substrate temperature was maintained at room temperature. By this procedure, an organic electroluminescence device with a luminescence area of 2 mm×2 mm was obtained, whose luminescence characteristics are shown in Table. 15 below.

As is shown in Table 15, when a hole-injection layer containing ionic compound (A-1) was formed by heating at 200° C. for 60 minutes, it was possible to obtain a device capable of being luminescent at a low voltage. This is thought to be because electrons were transferred from charge transporting macromolecule compound (P-1) and hole-transporting compound (H-2) to ionic compound (A-1) and cation radical (free carrier) was produced, leading to the formation of a hole-injection layer with excellent charge transporting property (hole-injection/transporting property).

Example 2

The same procedure as in Example 1 was followed except that compound (B-30) shown in the above-mentioned table was added at 0.2 weight % instead of ionic compound (A-1) as an ionic compound, and an organic electroluminescence device was prepared. The luminescence characteristics of the device obtained are shown in Table 15. It was possible to obtain a luminescence device functioning at a low voltage even at a heating/drying temperature of 200° C.

Comparative Example 1

The same procedure as in Example 1 was followed to obtain an organic electroluminescence device except that a hole-injection layer was prepared under the conditions shown in Table 13 below.

TABLE 13

| Solvent | Ethyl Benzoate | |
| --- | --- | --- |
| Concentration of Coating Solution | Tris(Pentafluoro-Phenyl)Borane (PPB: Compound whose Structure is Shown Below) | 0.20 Weight % |
|  | Charge Transporting Macromolecule Compound (P-1) | 0.33 Weight % |
|  | Hole-Transporting Compound (H-2) | 1.67 Weight % |
| Revolution of Spinner | 1500 rpm | |
| Time of Revolution of Spinner | 30 Seconds | |
| Drying Condition | 200° C., 60 Minutes in Oven after 80° C., 1 Minute on Hot Plate | |

[Chemical Formula 32]

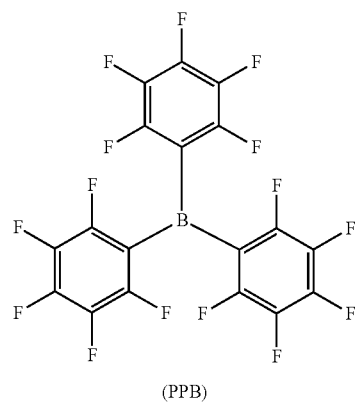

(PPB)

The luminescence characteristics of the device obtained are shown in Table 15 below. As is shown in the Table 15, when the hole-injection layer containing tris(pentafluorophenyl)borane (PPB) was formed by heat-drying at 200° C. for 60 minutes, the driving voltage was very high. This will be due to poor heat-resistant property of PPB.

Comparative Example 2

The same procedure as in Example 1 was followed to obtain an organic electroluminescence device except that a hole-injection layer was prepared under the conditions shown in Table 14 below.

TABLE 14

| Solvent | Ethyl Benzoate | |
|---|---|---|
| Concentration of Coating Solution | Tris(PentafluoroPhenyl) Borane (PPB) | 0.20 Weight % |
| | Charge Transporting Macromolecule Compound (P-1) | 0.33 Weight % |
| | Hole-Transporting Compound (H-2) | 1.67 Weight % |
| Revolution of Spinner | 1500 rpm | |
| Time of Revolution of Spinner | 30 Seconds | |
| Drying Condition | 100° C., 60 Minutes in Oven after 80° C., 1 Minute on Hot Plate | |

The luminescence characteristics of the device obtained are shown in Table 15 below. As is apparent from the results in Table 15, when the hole-injection layer containing tris(pentafluorophenyl) borane (PPB) was heat-dried at 100° C. for 60 minutes, the driving voltage of the obtained device was high. This is thought to be because heating temperature at the time of the formation of the hole-injection layer was low and electron-accepting property of PPB was weaker (in comparison with ionic compound (A-1) of Example 1), this leading to the deterioration of the device characteristics.

TABLE 15

| | Heating/ Drying Temperature [° C.] | Driving Voltage to Give Luminance of 100 cd/m² [V] | Driving Voltage to Give Luminance of 1000 cd/m² [V] |
|---|---|---|---|
| Example 1 (A-1) | 200 | 3.5 | 5.1 |
| Example 2 (B-30) | 200 | 6.8 | 9.7 |
| Comparative Example 1 (PPB) | 200 | 8.2 | 11.1 |
| Comparative Example 2 (PPB) | 100 | 4.2 | 6.3 |

Example 3

The same procedure as in Example 1 was followed to obtain an organic electroluminescence device except that a hole-injection layer was prepared under the conditions shown below.

TABLE 16

| Solvent | Ethyl Benzoate | |
|---|---|---|
| Concentration of Coating Solution | Ionic Compound (compound (A-1) mentioned above as an example) | 0.40 Weight % |
| | Charge Transporting Macromolecule Compound (compound (P-1) mentioned above as an example) | 0.33 Weight % |
| | Charge Transporting Compound (compound (H-2) mentioned above as an example) | 1.67 Weight % |
| Revolution of Spinner | 1500 rpm | |
| Time of Revolution of Spinner | 30 Seconds | |
| Drying Condition | 230° C., 15 Minutes in Oven after 80° C., 1 Minute on Hot Plate | |

The luminescence characteristics of the device obtained are shown in Table 20. As is apparent from the results in Table 20, it was possible to obtain a luminescence device functioning at a low voltage under heating/drying conditions of 230° C. for 15 minutes.

Example 4

The same procedure as in Example 1 was followed to obtain an organic electroluminescence device except that a hole-injection layer was prepared under the conditions shown below.

TABLE 17

| Solvent | Ethyl Benzoate | |
|---|---|---|
| Concentration of Coating Solution | Ionic Compound (Compound 4) | 0.40 Weight % |
| | Charge Transporting Macromolecule Compound (compound (P-1) mentioned above as an example) | 0.33 Weight % |
| | Charge Transporting Compound (compound (H-2) mentioned above as an example) | 1.67 Weight % |
| Revolution of Spinner | 1500 rpm | |
| Time of Revolution of Spinner | 30 Seconds | |
| Drying Condition | 230° C., 15 Minutes in Oven after 80° C., 1 Minute on Hot Plate | |

The luminescence characteristics of the device obtained are shown in Table 20. As is apparent from the results in Table 20, it was possible to obtain a luminescence device functioning at a low voltage under heating/drying conditions of 230° C. for 15 minutes.

Example 5

The same procedure as in Example 1 was followed to obtain an organic electroluminescence device except that a hole-injection layer was prepared under the conditions shown below.

TABLE 18

| | Solvent | Ethyl Benzoate |
|---|---|---|
| Concentration of Coating Solution | Ionic Compound (Compound 4) | 0.80 Weight % |
| | Charge Transporting Macromolecule Compound (compound (P-1) mentioned above as an example) | 0.33 Weight % |
| | Charge Transporting Compound (compound (H-2) mentioned above as an example) | 1.67 Weight % |
| Revolution of Spinner | | 1500 rpm |
| Time of Revolution of Spinner | | 30 Seconds |
| Drying Condition | | 230° C., 15 Minutes in Oven after 80° C., 1 Minute on Hot Plate |

The luminescence characteristics of the device obtained are shown in Table 20. As is apparent from the results in Table 20, it was possible to obtain a luminescence device functioning at a low voltage under heating/drying conditions of 230° C. for 15 minutes.

Comparative Example 3

The same procedure as in Example 1 was followed to obtain an organic electroluminescence device except that a hole-injection layer was prepared under the conditions shown below.

TABLE 19

| | Solvent | Ethyl Benzoate |
|---|---|---|
| Concentration of Coating Solution | TBPAH (Tris(4-Bromophenyl)Aminium Hexachloroantimonate) | 0.40 Weight % |
| | Charge Transporting Macromolecule Compound (compound (P-1) mentioned above as an example) | 0.33 Weight % |
| | Charge Transporting Compound (compound (H-2) mentioned above as an example) | 1.67 Weight % |
| Revolution of Spinner | | 1500 rpm |
| Time of Revolution of Spinner | | 30 Seconds |
| Drying Condition | | 230° C., 15 Minutes in Oven after 80° C., 1 Minute on Hot Plate |

[Chemical Formula 33]

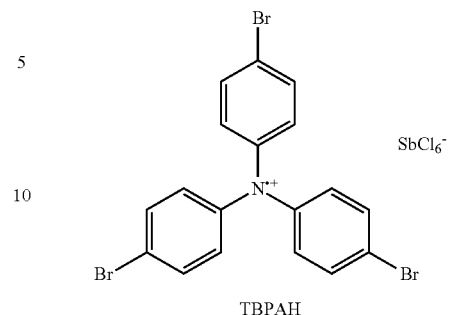

TBPAH

The luminescence characteristics of the device obtained are shown in Table 20. As is apparent from the results in Table 20, when the hole-injection layer coated with a composition containing TBPAH was heat-dried at 230° C. for 15 minutes, the driving voltage of the device was high. This is thought to be because hexachloroantimonate, which is an anion, interacted strongly with radical cation of the hole-transporting compound and transfer of positive charge was inhibited, this leading to insufficiently low driving voltage.

TABLE 20

| | Concentration of Electron-Accepting Compound in Coating Solution [Weight %] | Heating/Drying Temperature [° C.] | Driving Voltage to Give Luminance of 100 Cd/M² [V] | Driving Voltage to Give Luminance Of 1000 Cd/M² [V] |
|---|---|---|---|---|
| Example 3 (A-1) | 0.40 | 230 | 4.0 | 5.6 |
| Example 4 (Compound 4) | 0.40 | 230 | 4.0 | 5.8 |
| Example 5 (Compound 4) | 0.80 | 230 | 4.0 | 5.7 |
| Comparative Example 3 (TBPAH) | 0.40 | 230 | 8.3 | 11.2 |

Example 6

A device was prepared by the method described in Example 3 and the device obtained was subjected to the following sealing treatment to prevent the deterioration of the device due to moisture in the air during storage.

In a glove box filled with nitrogen gas, light-hardening resin of approx. 1 mm in width was coated on the peripheral part of a glass plate (20 mm×60 mm) and a desiccant sheet (Getter Drier manufactured by SAES Getters Co.) was placed on the central area. A substrate, whose vapor deposition of the cathode had been completed in the manner shown in Example 1, was placed onto the glass plate so that the surface of the vapor deposition faces the desiccant sheet and the light-hardening resin area was hardened by irradiation with UV light.

After the sealing treatment, the substrate was taken out of the dry box, made to be luminous by passing a forward current of 7.5 mA/cm² and the voltage was measured. Thereafter, the substrate was stored for 500 hours in a thermostatic chamber, maintained at 100° C., in air. The device was taken out after storage, made to be luminous by passing a forward current of 7.5 mA/cm² and the voltage was measured. The voltages before and after the storage are shown in Table 21. The device comprising a hole-injection layer containing compound (A-1) had its driving voltage only slightly elevated after storage at 100° C. for 500 hours.

Comparative Example 4

A device was prepared by the same method as described for Example 6, except that TBPAH was used in place of compound (A-1) and its concentration in the composite was adjusted to 0.40 weight %. The voltage was measured before and after storage at 100° C. The results are shown in Table 21. The device comprising a hole-injection layer containing TBPAH showed a high voltage immediately after preparation and the increase in voltage after storage at 100° C. for 500 hours was also high.

TABLE 21

| | Concentration of Electron-Accepting Compound in Coating Solution [Weight %] | Device Voltage [V] When Forward Current of 7.5 ma/Cm² Was Passed | | |
|---|---|---|---|---|
| | | Device immediately after Preparation | Device Stored at 100° C. for 500 Hours | Difference before and after Storage |
| Example 6 (A-1) | 0.40 | 4.2 | 4.7 | 0.5 |
| Comparative Example 4 (TBPAH) | 0.40 | 4.4 | 5.3 | 0.9 |

Example 7

To the device prepared by the same method as described for Example 6 was passed a constant current of 21 mA/cm² continuously at room temperature (24° C.) and the driving voltage of the device was measured at the same time. The device voltages at the time of starting current application and after current application for 1000 hours are presented in Table 22. The device having a hole-injection layer made from a coating solution containing 0.40 weight % of compound (A-1) had its driving voltage increased only slightly at the time of constant current application.

Example 8

To the device prepared by the same method as described for Example 6, except that the film of a hole-injection layer was made from a coating solution containing 0.20 weight % of compound (A-1) in place of 0.40 weight %, was passed constant current of 21 mA/cm² continuously at room temperature (24° C.) and the driving voltage of the device was measured at the same time. The device voltages at the time of starting current application and after current application for 1000 hours are presented in Table 22. The device having a hole-injection layer made from a coating solution containing 0.20 weight % of compound (A-1) had its driving voltage increased only slightly at the time of constant current application.

Example 9

To the device prepared by the same method as described for Example 6, except that the film of a hole-injection layer was made from a coating solution containing 0.60 weight % of compound (A-1) in place of 0.40 weight %, was passed a constant current of 21 mA/cm² continuously at room temperature (24° C.) and the driving voltage of the device was measured at the same time. The device voltages at the time of starting current application and after current application for 1000 hours are presented in Table 22. The device having a hole-injection layer made from a coating solution containing 0.60 weight % of compound (A-1) also had its driving voltage increased only slightly at the time of constant current application.

Example 10

To the device prepared by the same method as described for Example 6, except that the film of a hole-injection layer was made from a coating solution containing 0.80 weight % of compound (A-1) in place of 0.40 weight %, was passed a constant current of 21 mA/cm² continuously at room temperature (24° C.) and the driving voltage of the device was measured at the same time. The device voltages at the time of starting current application and after current application for 1000 hours are presented in Table 22. The device having a hole-injection layer made from a coating solution containing 0.80 weight % of compound (A-1) also had its driving voltage increased only slightly at the time of constant current application.

Comparative Example 5

To the device prepared by the same method as described for Example 6, except that the film of a hole-injection layer was made from a coating solution containing 0.80 weight % of TBPAH in place of 0.40 weight % of compound A-1, was passed a constant current of 21 mA/cm² continuously at room temperature (24° C.) and the driving voltage of the device was measured at the same time. The device voltages at the time of starting current application and after current application for 1000 hours are presented in Table 22. The device having a hole-injection layer made from a coating solution containing 0.80 weight % of TBPAH showed a high device voltage at the time of starting current application and an increase at time of continuous current application was also high.

Comparative Example 6

To the device prepared by the same method as described for Example 6, except that the film of a hole-injection layer was made from a coating solution containing 0.20 weight % of TBPAH in place of 0.40 weight % of compound A-1, was passed a constant current of 21 mA/cm² continuously at room temperature (24° C.) and the driving voltage of the device was measured at the same time. The device voltages at the time of starting current application and after current application for 1000 hours are presented in Table 22. The device having a hole-injection layer made from a coating solution containing 0.20 weight % of TBPAH showed a higher voltage at the time of starting current application than the device having a hole-injection layer made from a coating solution containing 0.80 weight % of TBPAH and an increase at time of continuous current application was also high.

TABLE 22

| | Concentration of Electron-Accepting Compound in Coating Solution [Weight %] | Device Voltage [V] When Forward Current of 21 Ma/Cm² Was Continuously Applied | | Difference between Voltages before and after Current Application for 100 Hours |
|---|---|---|---|---|
| | | At Start of Current Application | After Current Application for 1000 Hours | |
| Example 7 (A-1) | 0.40 | 4.5 | 5.2 | 0.7 |
| Example 8 (A-1) | 0.20 | 4.5 | 5.1 | 0.6 |
| Example 9 (A-1) | 0.60 | 4.4 | 5.0 | 0.6 |
| Example 10 (A-1) | 0.80 | 4.4 | 5.1 | 0.7 |
| Comparative Example 5 (TBPAH) | 0.80 | 4.7 | 5.7 | 1.0 |
| Comparative Example 6 (TBPAH) | 0.20 | 5.2 | 6.4 | 1.2 |

Example 11

Charge-Transport Film 1 and Non-Luminescent Device 1

A composition comprising electron-accepting compounds (compound (A-1) and charge-transporting compound P-1 (weight-average molecular weight 29,600; glass transition temperature 177° C.)) and a solvent was spin-coated on an ITO substrate, which had been subjected to a series of washing procedure following anode patterning, to form a charge-transport film 1, which was a homogeneous thin film having a thickness of 200 nm. Spin coating was carried out in air at a temperature of 23° C. and a relative humidity of 40%.

TABLE 23

| Solvent | Anisole | |
|---|---|---|
| Concentration of Coating Solution | Ionic Compound (compound (A-1) mentioned above as an example) | 1.0 Weight % |
| | Charge Transporting Macromolecule Compound (compound (P-1) mentioned above as an example) | 5.0 weight % |
| Revolution of Spinner | 1500 rpm | |
| Time of Revolution of Spinner | 30 Seconds | |
| Drying Condition | 230° C., 15 Minutes in Oven after 80° C., 1 Minute on Hot Plate | |

After drying, as a mask for cathode vapor deposition, a stripe-shaped shadow mask of 2 mm in width was contacted with the device at right angles to ITO stripe of the anode, which was then placed in a vacuum vapor deposition instrument, from which air was evacuated until the vacuum reached $3 \times 10^{-4}$ Pa or lower. As a cathode, an aluminum layer was formed at a thickness of 80 nm at a deposition speed of 0.5 nm/sec and vacuum of $5 \times 10^{-4}$ Pa by heating aluminum using a molybdenum boat. The substrate temperature at the time of the above vapor deposition was maintained at room temperature. The procedure thus produced a non-luminescent device 1 having a current-carrying area of 2 mm×2 mm and a charge-transport film 1 sandwiched between ITO anode and cathode.

The current density, when voltage of 0.6 v was applied to this device corresponding to field intensity of $3.0 \times 10^4$ [V/cm] as calculated by the formula (voltage applied/charge-transport film thickness), was $5.7 \times 10^{-3}$ [A/cm²].

The resistivity, as calculated by the formula (field intensity [V/cm]/current density [A/cm²]), was $5.3 \times 10^7$ [Ωcm].

(Charge-Transport Film 2 and Non-Luminescent Device 2)

Charge-transport film 2 was prepared by the same method as described for charge-transport film 1, and non-luminescent device 2 was prepared by the same method as described for non-luminescent device 1, except that the condition of charge-transport film formation was as described below. The thickness of the charge-transport film 2 was 180 nm.

TABLE 24

| Solvent | Anisole | |
|---|---|---|
| Concentration Of Coating Solution | Charge Transporting Macromolecule Compound (compound (P-1) mentioned above as an example) | 5.0 Weight % |
| Revolution of Spinner | 1500 rpm | |
| Time of Revolution of Spinner | 30 Seconds | |
| Drying Condition | 230° C., 15 Minutes in Oven after 80° C., 1 Minute on Hot Plate | |

The current density, when voltage of 24 v was applied to this device corresponding to field intensity of $1.3 \times 10^6$ [V/cm] as calculated by the formula (voltage applied/charge-transport film thickness), was $5.4 \times 10^{-3}$ [A/cm²].

The resistivity, as calculated by the formula (field intensity [V/cm]/current density [A/cm²]), was $2.4 \times 10^{10}$ [Ωcm].

The values of resistivity of the charge-transport film 1 and the charge-transport film 2, together with their ratio, are shown in Table 27.

Comparative Example 7

Charge-Transport Film 1' and Non-Luminescent Device 1')

Charge-transport film 1' was prepared by the same method as described for charge-transport film 1 of Example 11 and non-luminescent device 1' was prepared by the same method as described for non-luminescent device 1, except that the condition of charge-transport film formation was as described below. The thickness of the charge-transport film 1' was 120 nm.

TABLE 25

| Solvent | Anisole | |
|---|---|---|
| Concentration of Coating Solution | PPB (Tris(Pentafluoro-Phenyl)Borane) | 1.0 weight % |
| | Charge Transporting Compound (compound (H-2) mentioned above as an example) | 5.0 weight % |
| Revolution of Spinner | 1500 rpm | |
| Time of Revolution of Spinner | 30 Seconds | |
| Drying Condition | 100° C., 1 Hour in Oven after 80° C., 1 minute on Hot Plate | |

The current density, when voltage of 1.1 v was applied to this device corresponding to field intensity of $9.5 \times 10^4$ [V/cm] as calculated by the formula (voltage applied/charge-transport film thickness), was $5.4 \times 10^{-3}$ [A/cm$^2$].

The resistivity, as calculated by the formula (field intensity [V/cm]/current density [A/cm$^2$]), was $1.8 \times 10^7$ [Ωcm].

(Charge-Transport Film 2' and Non-Luminescent Device 2')

Charge-transport film 2' was prepared by the same method as described for charge-transport film 1' and non-luminescent device 2' was prepared by the same method as described for non-luminescent device 1', except that the condition of charge-transport film formation was as described below. The thickness of the charge-transport film 2' was 100 nm.

TABLE 26

| Solvent | Anisole | |
|---|---|---|
| Concentration of Coating Solution | Charge Transporting Compound (compound (H-2) mentioned above as an example) | 5.0 Weight % |
| Revolution of Spinner | 1500 rpm | |
| Time of Revolution of Spinner | 30 Seconds | |
| Drying Condition | 230° C., 15 Minutes in Oven after 80° C., 1 Minute on Hot Plate | |

The current density, when voltage of 10 v was applied to this device corresponding to field intensity of $1.0 \times 10^6$ [V/cm] as calculated by the formula (voltage applied/charge-transport film thickness), was $4.8 \times 10^{-3}$ [A/cm$^2$].

The resistivity, as calculated by the formula (field intensity [V/cm]/current density [A/cm$^2$]), was $2.1 \times 10^8$ [Ωcm].

The values of resistivity of charge-transport film 1' and charge-transport film 2', together with their ratio, are shown in Table 27.

TABLE 27

| | | Charge-Transporting Compound | Electron-Accepting Compound | Resistivity along Film Thickness [ΩCm] | Relative Ratio of Resistivity [1] |
|---|---|---|---|---|---|
| Example 11 | Charge-Transport Film 1 | Compound (P-1) mentioned above as an example | Compound (A-1) mentioned above as an example | $5.3 \times 10^7$ | $2.2 \times 10^{-3}$ |
| | Charge-Transport Film 2 | Compound (P-1) mentioned above as an example | — | $2.4 \times 10^{10}$ | 1.0 |
| Comparative Example 7 | Charge-Transport Film 1' | Compound (H-2) mentioned above as an example | PPB | $1.8 \times 10^7$ | $8.5 \times 10^{-2}$ |
| | Charge-Transport Film 2' | Compound (H-2) mentioned above as an example | — | $2.1 \times 10^8$ | 1.0 |

[1] The ratio of the resistivity of a charge-transport film made from a composition containing an electron-accepting compound on the condition that the resistivity of a charge-transport film made from the same composition except for not containing the electron-accepting compound be 1.

As is evident from Example 11 and Comparative Example 7, it was found possible to obtain a film of low electric resistivity by using electron-accepting compounds of the present invention. Therefore, an organic electroluminescence device based on the charge-transport film comprising electron-accepting compounds of the present invention is expected to be a device with low driving voltage.

The present invention has been explained in detail above with reference to specific examples. However, it is evident to those skilled in the art that various modifications can be added thereto without departing from the intention and the scope of the present invention.

The present application is based on the descriptions of Japanese Patent Application No. 2004-68958, which was filed Mar. 11, 2004, Japanese Patent Application No. 2005-21983, which was filed Jan. 28, 2005, and Japanese Patent Application No. 2005-62541, which was filed Mar. 7, 2005, and their entireties are incorporated herewith by reference.

INDUSTRIAL APPLICABILITY

A composition for a charge-transport film of the present invention contains a heat stable ionic compound and a heat stable free carrier which is produced by electron transfer to the ionic compound. As a result, the composition is heat-resistant and excellent in charge transport capacity (hole injection/transport capacity). Therefore, the composition can be advantageously used as charge transport material in various areas such as organic electroluminescence device, electrophotographic photoreceptor, photoelectric conversion device, organic solar battery or organic rectifying device.

Further, an organic electroluminescence device of the present invention contains an above-mentioned ionic compound in a layer present between an anode and a cathode or emitting layer. This contributes to excellent heat stability and makes possible operation at a low voltage. Therefore, it will be possible to apply this device to flat-panel displays (for example, OA computers and wall-hanging TV sets), light sources taking advantage of surface emitting (for example, light sources of copying machines, backlight sources for liquid crystal displays, and other instruments), display boards and beacon lights. Particularly valuable will be its use as in-vehicle display device, for which excessively severe heat stability is required.

The invention claimed is:

1. A composition for a charge-transport film, comprising at least:
   a charge-transporting compound having an ionization potential of between 4.5 and 5.5 eV; and
   an ionic compound selected from the group consisting of the compounds of formulae (1)-(3),

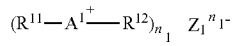

(1)

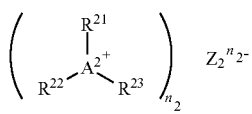

(2)

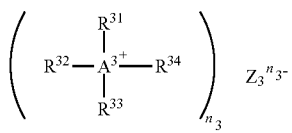

(3)

wherein:
$R^{11}$, $R^{21}$ and $R^{31}$ represent, independently of each other, an organic group bound to $A^1$-$A^3$, respectively, via a carbon atom;
$R^{12}$, $R^{22}$, $R^{23}$ and $R^{32}$-$R^{34}$ represent, independently of each other, an arbitrary group; wherein two or more neighboring groups of $R^{11}$-$R^{34}$ may combine together to form a ring;
$A^1$-$A^3$ each represent an element belonging to the third and subsequent periods in the periodic table;
$A^1$ represents an element belonging to group 17 of the long form periodic table;
$A^2$ represents an element belonging to group 16 of the long form periodic table;
$A^3$ represents an element belonging to group 15 of the long form periodic table;
$Z_1^{n1-}$-$Z_3^{n3-}$ represent, independently of each other, a counter anion; and
n1-n3 represent, independently of each other, an ionic valency of the counter anion.

2. The composition for a charge-transport film as defined in claim 1, wherein $R^{11}$, $R^{21}$, $R^{31}$ represent, an optionally substituted alkyl group, an optionally substituted alkenyl group, an optionally substituted alkynyl group, an optionally substituted aromatic hydrocarbon group or an optionally substituted aromatic heterocyclic group.

3. The composition for a charge-transport film as defined in claim 1, wherein $R^{12}$, $R^{22}$, $R^{23}$ and $R^{32}$-$R^{34}$ are each independently an optionally substituted alkyl group, an optionally substituted alkenyl group, an optionally substituted alkynyl group, an optionally substituted aromatic hydrocarbon group or an optionally substituted aromatic heterocyclic group.

4. The composition for a charge-transport film as defined in claim 1, wherein $R^{11}$-$R^{34}$ are each independently an optionally substituted aromatic hydrocarbon group or an optionally substituted aromatic heterocyclic group.

5. The composition for a charge-transport film as defined in claim 1, wherein
   the ionic compound is of formula (1) and $A^1$ is a bromine atom or an iodine atom, or
   the ionic compound is of formula (2) and $A^2$ is a selenium atom or a sulfur atom.

6. The composition for a charge-transport film as defined in claim 1, wherein the ionic compound is of formula (1) and, $A^1$ is an iodine atom.

7. The composition for a charge-transport film as defined in claim 1, wherein
$Z_1^{n1-}$-$Z_3^{n3-}$ are one of formulae (4)-(6), $$E^1 X_4^- \qquad (4)$$

$$E^2 X_6^- \qquad (5)$$

$$Ar^2 - \underset{\underset{Ar^3}{|}}{\overset{\overset{Ar^1}{|}}{E^3{}^-}} - Ar^4 \qquad (6)$$

wherein
$E^1$ and $E^3$ are each independently an element of group 13 of the long form periodic table;
$E^2$ is an element of group 15 of the long form periodic table;
X is a halogen atom; and
$Ar^1$-$Ar^4$ are each independently an optionally substituted aromatic hydrocarbon group or an optionally substituted aromatic heterocyclic group.

8. The composition for a charge-transport film as defined in claim 7, wherein
$Z_1^{n1-}$-$Z_3^{n3-}$ are independently of each other, of formulae (4')-(6'), $$BX'_4{}^- \qquad (4')$$

$$PX'_6{}^- \qquad (5')$$

$$Ar^{12} - \underset{\underset{Ar^{13}}{|}}{\overset{\overset{Ar^{11}}{|}}{B^-}} - Ar^{14} \qquad (6')$$

wherein
X' is a fluorine atom or a chlorine atom;

$A^{11}$-$Ar^{14}$ are each independently an optionally substituted aromatic hydrocarbon group or an optionally substituted aromatic heterocyclic group; and at least one of $Ar^{11}$-$Ar^{14}$ comprises at least one fluorine atom or chlorine atom as a substituent.

9. The composition for a charge-transport film as defined in claim 1, wherein the charge-transporting compound is an aromatic tertiary amine compound.

10. The composition for a charge-transport film as defined in claim 9, wherein the aromatic tertiary amine compound is a macromolecule compound having a weight-average molecular weight of 1000 or larger and 1000000 or smaller.

11. The composition for a charge-transport film as defined in claim 1, further comprising a solvent that dissolves the charge-transporting compound and the ionic compound, wherein the solvent is an ether, an ester or a mixture thereof.

12. An organic electroluminescence device comprising a charge-transport layer obtained from the composition for a charge-transport film as defined in claim 1.

13. An organic electroluminescence device, comprising:
a substrate;
an anode and cathode formed on said substrate;
an emitting layer disposed between said anode and said cathode; and
a layer formed between said anode and said emitting layer using a composition for a charge-transport film as defined in claim 1.

14. The organic electroluminescence device as defined in claim 13, wherein in said layer formed between said anode and said emitting layer, using said composition for a charge-transport film, the content of said ionic compound is 0.1 weight % or higher and 50 weight % or lower.

15. The organic electroluminescence device as defined in claim 13, further comprising a hole-injection layer and/or a hole-transport layer between said anode and said emitting layer, wherein said hole-injection layer and/or said hole-transport layer is formed using a composition for a charge-transport film as defined in claim 1.

16. The organic electroluminescence device as defined in claim 13, wherein said layer using said composition for a charge-transport film is formed by a wet coating method.

17. A method of producing an organic electroluminescence device as defined in claim 13, comprising:
drying said composition for a charge-transport film by heating at a higher temperature than the glass transition temperature of said charge-transporting compound.

18. A method of producing a charge-transport film by wet coating method using a composition for a charge-transport film as defined in claim 1, comprising: drying said composition for a charge-transport film by heating at a higher temperature than the glass transition temperature of said charge-transporting compound.

* * * * *